(12) United States Patent
Goepfert et al.

(10) Patent No.: US 11,332,797 B2
(45) Date of Patent: May 17, 2022

(54) METHOD FOR THE SELECTION OF A LONG-TERM PRODUCING CELL USING HISTONE ACYLATION AS MARKERS

(71) Applicant: Hoffmann-La Roche Inc., Little Falls, NJ (US)

(72) Inventors: Ulrich Goepfert, Penzberg (DE); Peter Becker, Groebenzell (DE); Benjamin Moritz, Munich (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/311,460

(22) PCT Filed: May 13, 2015

(86) PCT No.: PCT/EP2015/060593
§ 371 (c)(1),
(2) Date: Nov. 15, 2016

(87) PCT Pub. No.: WO2015/177022
PCT Pub. Date: Nov. 26, 2015

(65) Prior Publication Data
US 2017/0081732 A1    Mar. 23, 2017

(30) Foreign Application Priority Data
May 19, 2014  (EP) .................................... 14168896

(51) Int. Cl.
*C12Q 1/6888*     (2018.01)
*C12N 15/67*      (2006.01)

(52) U.S. Cl.
CPC ........... *C12Q 1/6888* (2013.01); *C12N 15/67* (2013.01); *C12Q 2537/164* (2013.01); *C12Q 2600/154* (2013.01)

(58) Field of Classification Search
None
See application file for complete search history.

(56) References Cited

FOREIGN PATENT DOCUMENTS

| JP | 2004016018 A | 2/2004 |
|----|--------------|--------|
| JP | 2008167678 A | 7/2008 |
| RU | 2425882 C1   | 10/2009 |
| WO | 2004/056986 A2 | 7/2004 |
| WO | 2011/128377 A1 | 10/2011 |

OTHER PUBLICATIONS

Urbanucci et al. (The Prostate, 2012. vol. 72, pp. 1223-1232).*
Allfrey et al., "Acetylation and methylation of histones and their possible role in the regulation of RNA synthesis" Proc. Nall. Acad. Sci. USA 51:786-794 ( 1964).
Anderson et al., "Normalization of Real-Time Quantitative Reverse Transcription-PCR Data: A Model-Based Variance Estimation Approach to Identify Genes Suited for Normalization, Applied to Bladder and Colon Cancer Data Sets" Cancer Res 64:5245-5250 ( 2004).
Arents et al., "The nucleosomal core histone octamer at 3.1 A resolution: A tripartite protein assembly and a left-handed superhelix" Proc. Nati. Acad. Sci. USA 88:10148-10152 ( 1991).
Arents et al., "Topography of the histone octamer surface: Repeating structural motifs utilized in the docking of nucleosomal DNA" Proc. Natl. Acad. Sci. USA 90:10489-10493 ( 1993).
Bailey et al., "Determination of Chinese Hamster Ovary Cell Line Stability and Recombinant Antibody Expression During Long-Term Culture" Biotechnol. Bioeng. 109:2093-2103 ( 2012).
Barnes et al., "Characterization of the Stability of Recombinant Protein Production in the GS-NS0 Expression System" Biotechnol. Bioeng. 73:261-270 ( 2001).
Barnes et al., "Molecular Definition of Predictive Indicators of Stable Protein Expression in Recombinant NS0 Myeloma Cells" Biotechnol. Bioeng. 85:115-121 ( 2004).
Barnes et al., "Stability of Protein Production From Recombinant Mammalian Cells" Biotechnol. Bioeng. 81:631-639 ( 2003).
Beneke et al., "Chromatin Composition is Changed by Poly(ADPribosyl)ation during Chromatin Immunoprecipitation" PloS One 7:e32914 ( 2012).
Boshart et al., "A Very Strong Enhancer is Located Upstream of an Immediate Early Gene of Human Cytomegalovirus" Cell 41:521-530 ( 1985).
Brooks, A.R. et al., "Transcriptional silencing is associated with extensive methylation of the CMV promoter following adenoviral gene delivery to muscle" the Journal of Gene Medicine 6:395-404 ( 2004).
Bustin et al., "The MIQE Guidelines: Minimum Information for Publication of Quantitative Real-Time PCR Experiments" Clin. Chem. 55:611-622 ( 2009).
Cedar et al., "Linking DNA methylation and histone modification: patterns and paradigms" Nat. Rev. Genet. 10:295-304 ( 2009).
Chapman et al., "Effect of intron A from human cytomegalovirus (Towne) immediate-early gene on heterologous expression in mammalian cells" Nucleic Acids Research 19:3979-3986 ( 1991).
Chen et al., "Chromatin modifiers and remodellers: regulators of cellular differentiation" Nat. Rev. Genet. 15:93-106 ( 2014).
Cheung et al., "Signaling to Chromatin through Histone Modifications" Cell 103:263-271 ( 2000).
Chusainow et al., "A Study of Monoclonal Antibody-Producing CHO Cell Lines: What Makes a Stable High Producer?" Biotechnol. Bioeng. 102:1182-1196 ( 2009).
Creyghton et al., "Histone H3K27ac separates active from poised enhancers and predicts developmental state" Proc. Nall. Acad. Sci. USA 107:21931-21936 ( 2010).
Dawson et al., "Cancer Epigenetics: From Mechanism to Therapy" Cell:12-17 ( 2012).

(Continued)

Primary Examiner — Nancy J Leith
(74) Attorney, Agent, or Firm — Nicole Fortune

(57) ABSTRACT

Herein is reported a method for determining methylation of a promoter nucleic acid operably linked to a nucleic acid encoding a polypeptide and thereby determining the long-term productivity of a cell. Also an aspect is a method for selecting a cell for producing a polypeptide by determining the methylation of the promoter nucleic acid operably linked to the structural gene encoding the polypeptide.

15 Claims, 36 Drawing Sheets

Specification includes a Sequence Listing.

(56) References Cited

OTHER PUBLICATIONS

Eden et al., "DNA methylation models histone acetylation" Nature 394:842-843 ( 1998).
Escher, et al., "Demethylation using the epigenetic modifier, 5-azacytidine, increases the efficiency of transient transfection of macrophages" Journal of Lipid Research 46:356-365 ( 2005).
Feller et al., "Global and Specific Responses of the Histone Acetylome to Systematic Perturbation" Cell 57:599-571 ( 2015).
Foecking & Hofstetter, "Powerful and versatile enhancer-promoter unit for mammalian expression vectors" Gene 45:101-105 ( 1986).
Frommer et al., "A genomic sequencing protocol that yields a positive display of 5-methylcytosine residues in individual DNA strands" Proc. Nati. Acad. Sci. USA 89:1827-1831 ( 1992).
Garrick et al., "Repeat-induced gene silencing in mammals" Nature Genetics 18(1):56-59 (Jan. 1, 1998).
Grigg et al., "Sequencing 5-methylcytosine residues by the bisulphite method" DNA Sequence 6:189-198 ( 1996).
Grigg et al., "Sequencing 5-methylcytosine residues in genomic DNA" BioEssays 16( Suppl 431-436).
Hashimshony et al., "The role of DNA methylation in setting up chromatin structure during development" Nat. Ganet. 34:187-192 ( 2003).
He et al., "Transgene Copy Number Distribution Profiles in Recombinant CHO Cell Lines Revealed by Single Cell Analyses" Biotechnol. Bioeng. 109:1713-1722 ( 2012).
ISR for PCT/EP2015/060593.
Kaufman et al., "Evolution of Chromosomal Regions Containing Transfected and Amplified Dihydrofolate Reductase Sequences" Mol. Cell. Biol.:699-711 ( 1983).
Kaufman et al., "Homogeneity and persistence of transgene expression by omitting antibiotic selection in cell line isolation" Nucleic Acids Research 36( Suppl 17):e111 ( 2008).
Kim et al., "Stability of Protein Production From Recombinant Mammalian Cells" Biotechnol. Bioeng. 108:2434-2446 ( 2011).
Koch et al., "The landscape of histone modifications across 1% of the human genome in five human cell lines" Genome Research 17:691-707 ( 2007).
Kong et al., "Transgene Expression is Associated with Copy Number and Cytomegalovirus Promoter Methylation in Transgenic Pigs" PloS One 4:e6679 ( 2009).
Kouzarides et al., "Chromatin Modifications and Their Function" Cell 128:693-705 ( 2007).
Krishnan, et al., "Effects of epigenetic modulation on reporter gene expression: implications for stem cell imaging" the FASEB Journal ( 2006).
Lattenmayer et al., "Identification of transgene integration loci of different highly expressing recombinant CHO cell lines by FISH" Cytotechnology 51:171-182 ( 2006).
Livak & Schmittgen, "Analysis of Relative Gene Expression Data Using Real-Time Quantitative PCR and the 2-$^{\Delta\Delta C}{}_T$ Method" Methods 25:402-408 (Dec. 2001).
Martin et al., "The vagaries of variegating transgenes" BioEssays 18:919-923 ( 1996).

McBurney et al., "Evidence for Repeat-Induced Gene Silencing in Cultured Mammalian Cells: Inactivation of Tandem Repeats of Transfected Genes" Exp. Cell Res. 274:1-8 ( 2002).
Mehta et al., "Epigenetic regulation of cytomegalovirus major immediate-early promoter activity in transgenic mice" Gene 428:20-24 ( 2009).
Migliaccio et al., "Stable and unstable transgene integration sites in the human genome: extinction of the Green Fluorescent Protein transgene in K562 cells" Gene 256:197-214 ( 2000).
Miller et al., "Taking It Off: Regulation of H3 K56 Acetylation by Hst3 and Hst4" Cell Cycle 5:2561-2565 ( 2006).
Mutskov & Felsenfeld, "Silencing of transgene transcription precedes methylation of promoter DNA and histone H3 lysine 9" the EMBO Journal 23:138-149 ( 2004).
Osterlehner et al., "Promoter Methylation and Transgene Copy Numbers Predict Unstable Protein Production in Recombinant Chinese Hamster Ovary Cell Lines" Biotechnol. Bioeng. 108:2670-2681 ( 2011).
Paredes et al., "Unstable expression of recombinant antibody during long-term culture of CHO cells is accompanied by histone H3 hypoacetylation" Biotechnol Lett 35:987-993 ( 2013).
Phillips et al., "The Presence of Acetyl Groups in Histones" Biochem. J. 87:258-263 ( 1963).
Strutzenberger, et al., "Changes during subclone development and ageing of human antibody-producing recombinant CHO cells" J. Biotechnol. 69:215-226 ( 1999).
Thomas et al., "An octamer of histones in chromatin and free in solution" Proc. Nat. Acad. Sci. USA 72:2626-2630 ( 1975).
Turner et al., "Cellular Memory Review and the Histone Code" Cell 111:285-291 ( 2002).
Wang et al., "Combinatorial patterns of histone acetylations and methylations in the human genome" Nat. Ganet. 40:897-903 ( 2008).
Wright et al., "Diverse Plasmid DNA Vectors by Directed Molecular Evolution of Cytomegalovirus Promoters" Human Gene Therapy 16:881-892 ( 2005).
Yang et al., "DNA methylation contributes to loss in productivity of monoclonal antibody-producing CHO cell lines" J. Biotechnol. 147:180-185 ( 2010).
Yin et al., "Position effect variegation and epigenetic modification of a transgene in a pig model" Genet. Mol. Res. 11:355-369 ( 2012).
Zentner & Henikoff, "Regulation of nucleosome dynamics by histone modifications" Nat. Struct. Mol. Biol. 20:259-266 ( 2013).
Graessmann et al. DNA Methylation: Molecular Biology and Biological Significance Basel, Switzerland, Birkhauser Verlag, (1993).
Egger et al., "Epigeneties in human disease and prospects for epigenetie therapy" Nature 429:457-463 ( 2004).
Meilinger et al., "Np95 interacts with de novo DNA methyltransferases, Dnmt3a and Dnmt3b, and mediated epigenetic silencing of the viral CMV promoter in embryonic stem cells" EMBO Reports 10(11):1259-1264 ( 2009).
Moritz et al., "High Levels of Histone H3 Acetylation at the CMV Promoter are Predictive of Stable Expression in Chinese Hamster Ovary Cells" Biotechnology Prog. 32(3):776-786 ( 2016).
Rivera et al., "Epigenetics in humans: an overview" Current Opinion in Endocrinology, Diabetes & Obesity 17:493-499 ( 2010).
Thrall et al. Brenner's Encyclopedia of Genetics "Promoters" 2nd edition, ( 2013).

* cited by examiner

Fig. 17
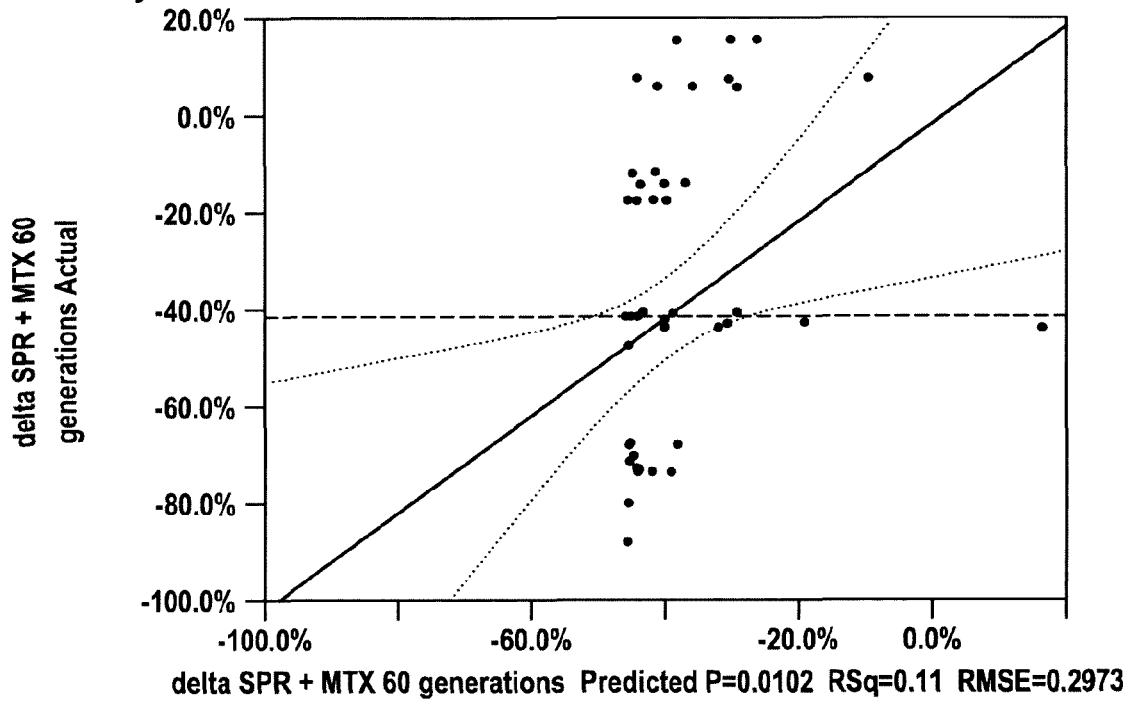
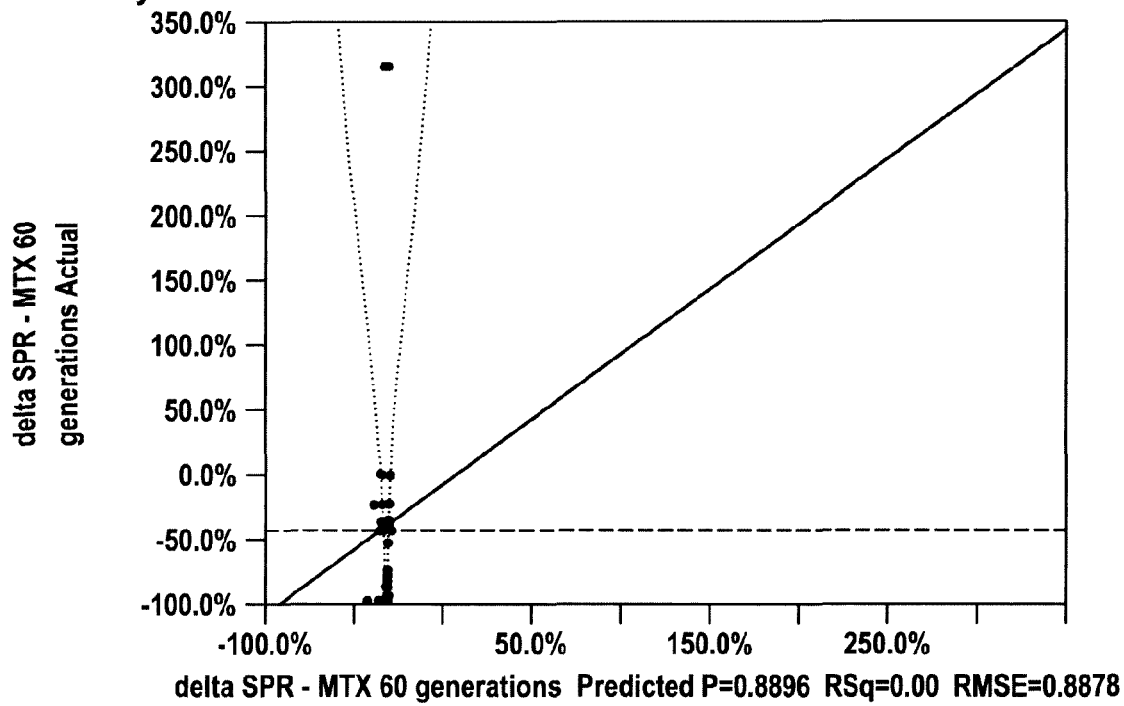

Fig. 18
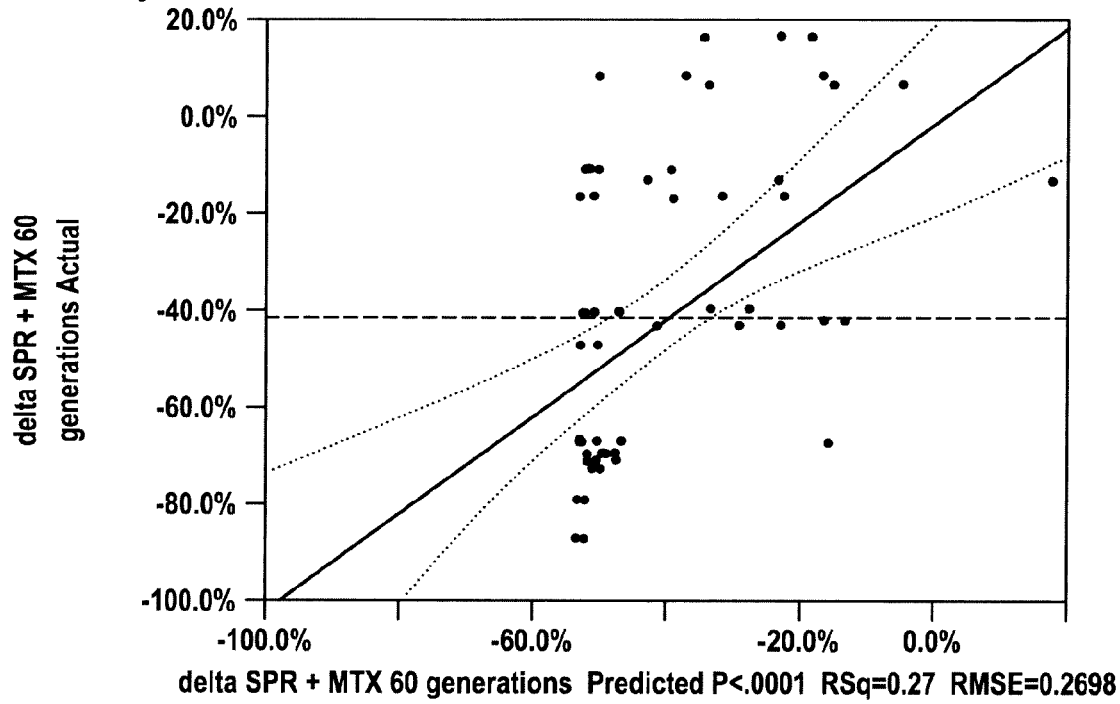
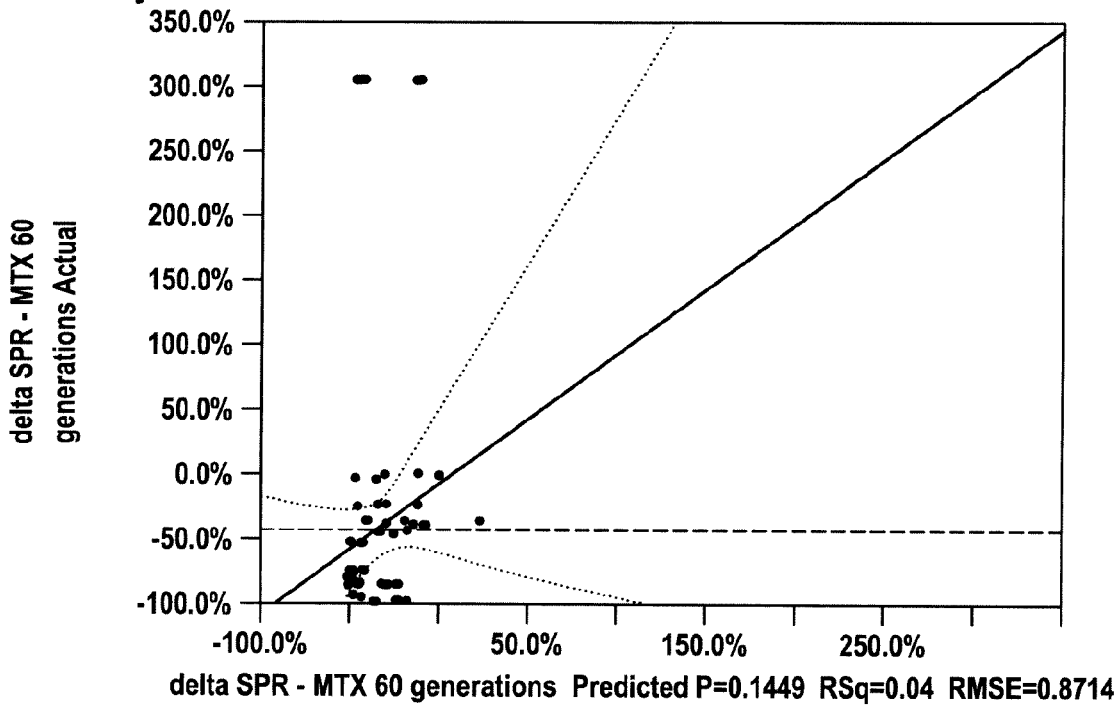

Fig. 19
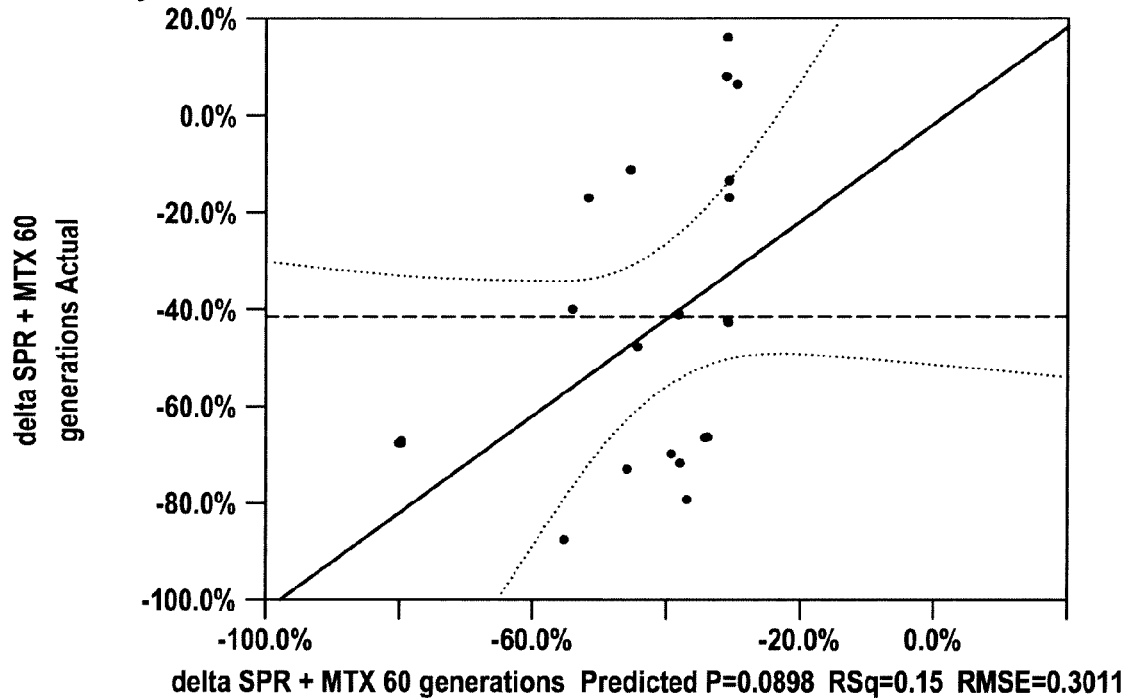
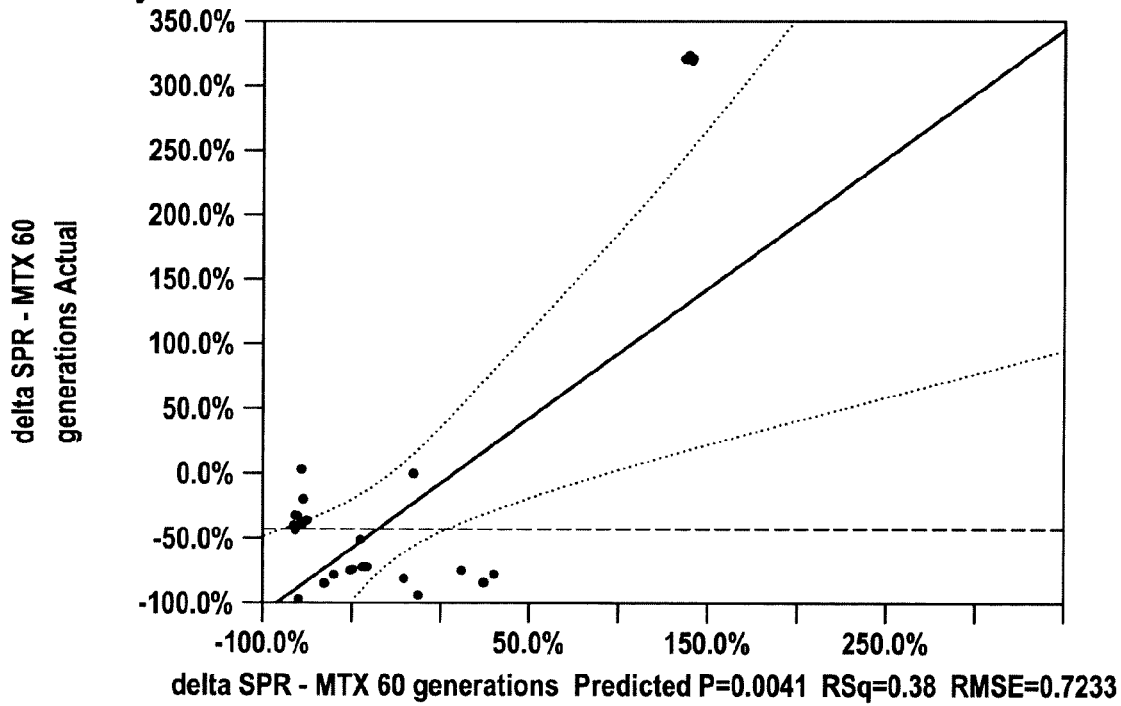

α = 0.05

Fig. 21
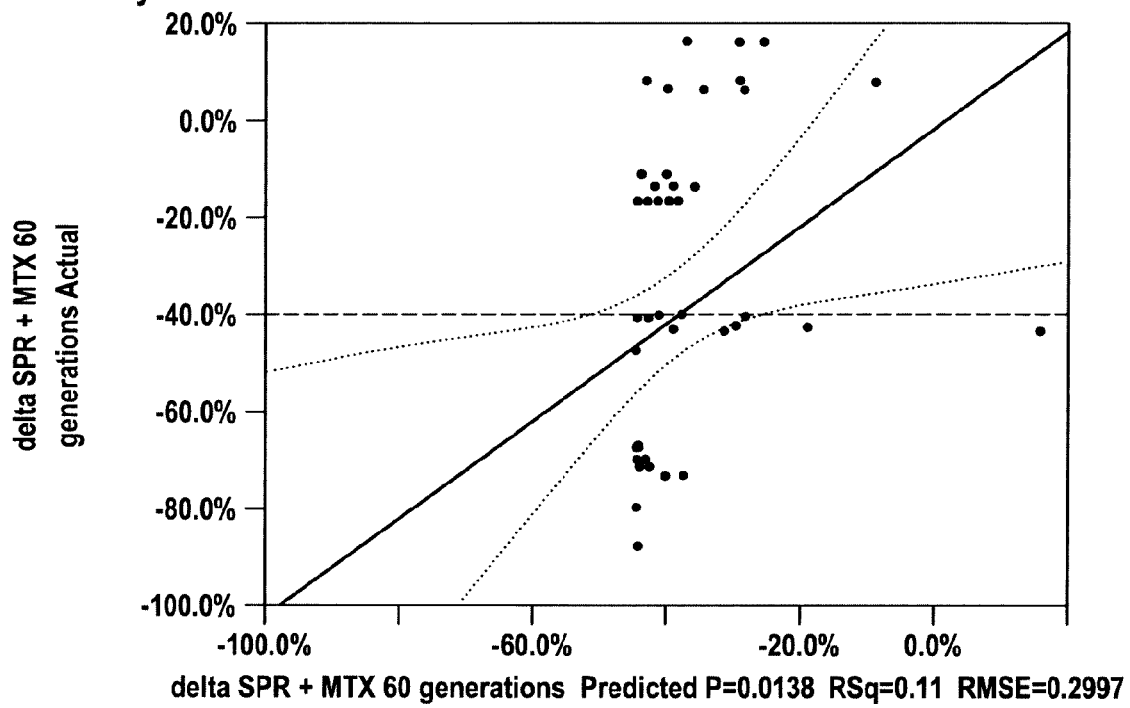
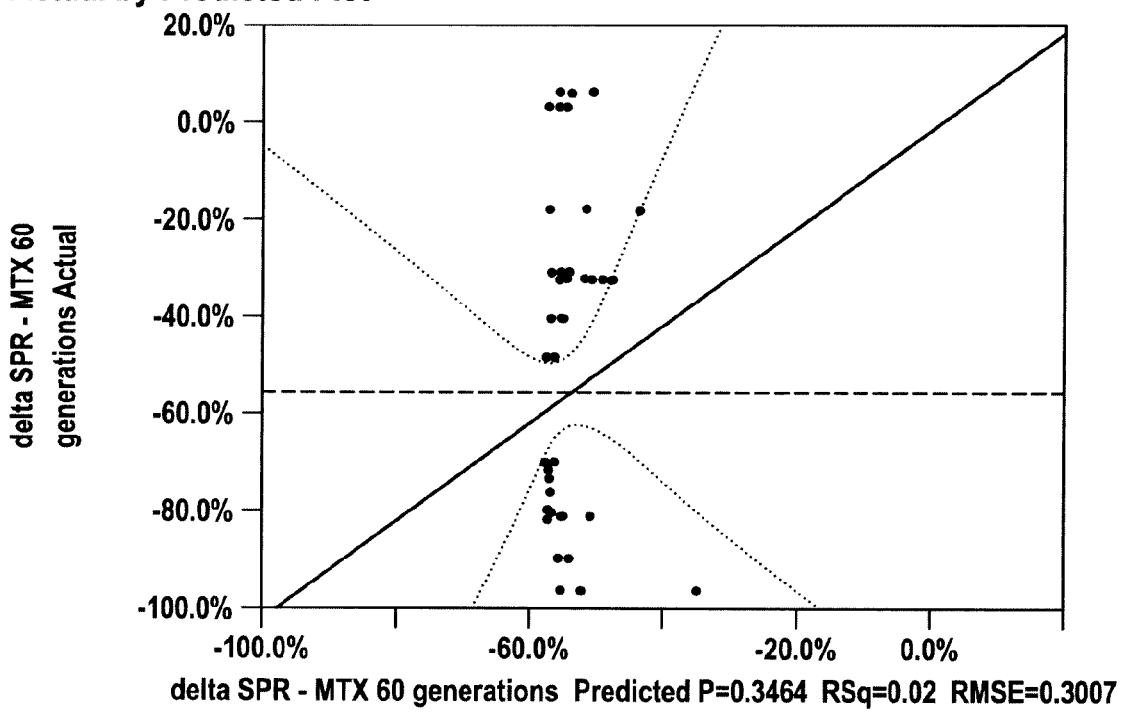

Fig. 22
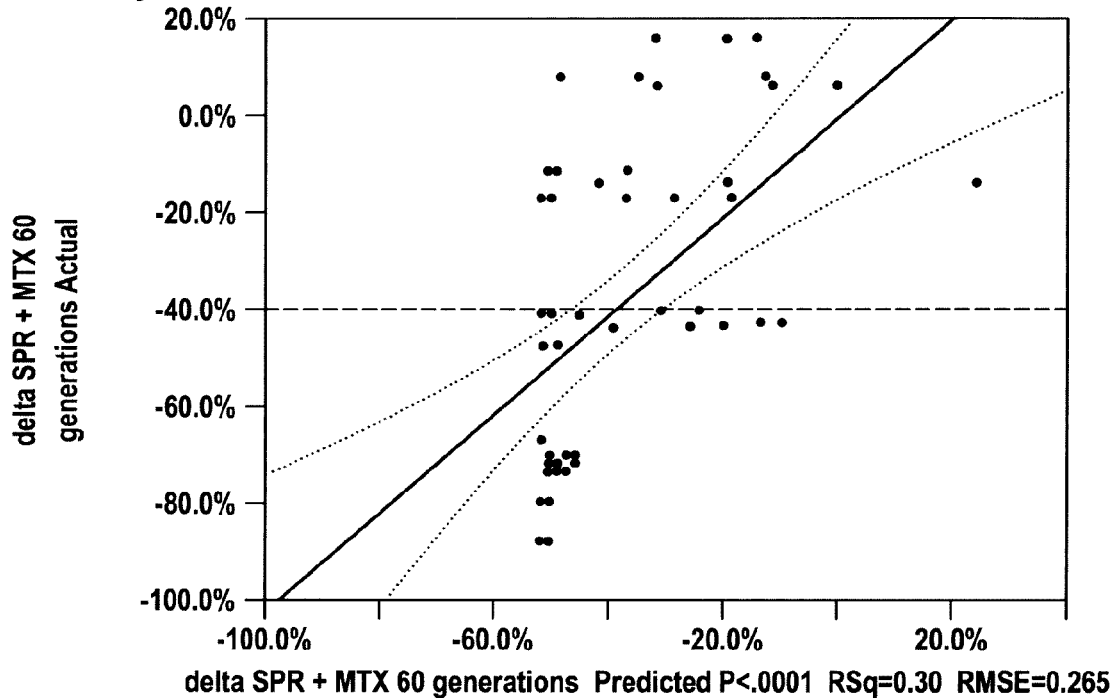
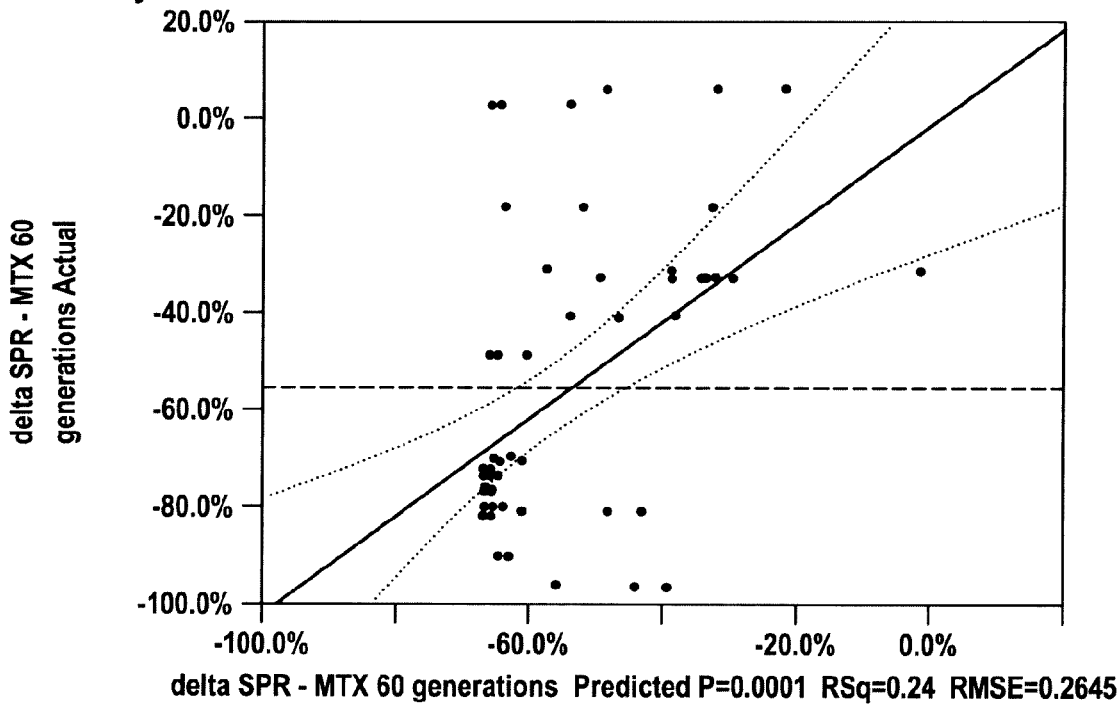

Fig. 23
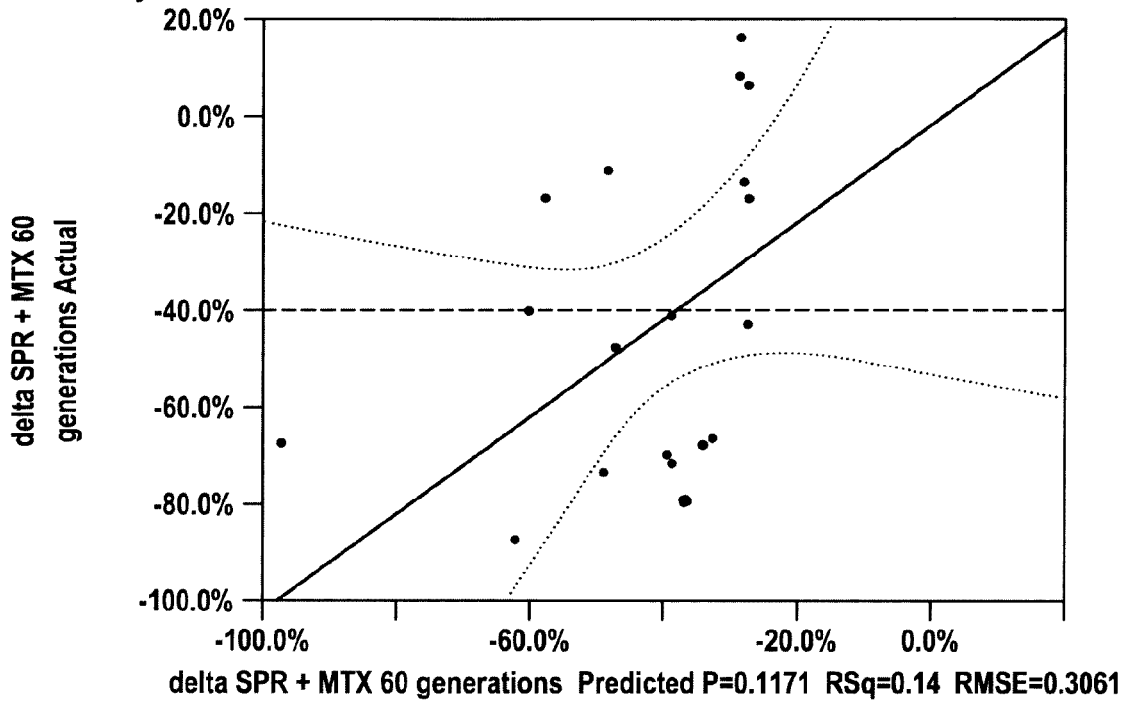
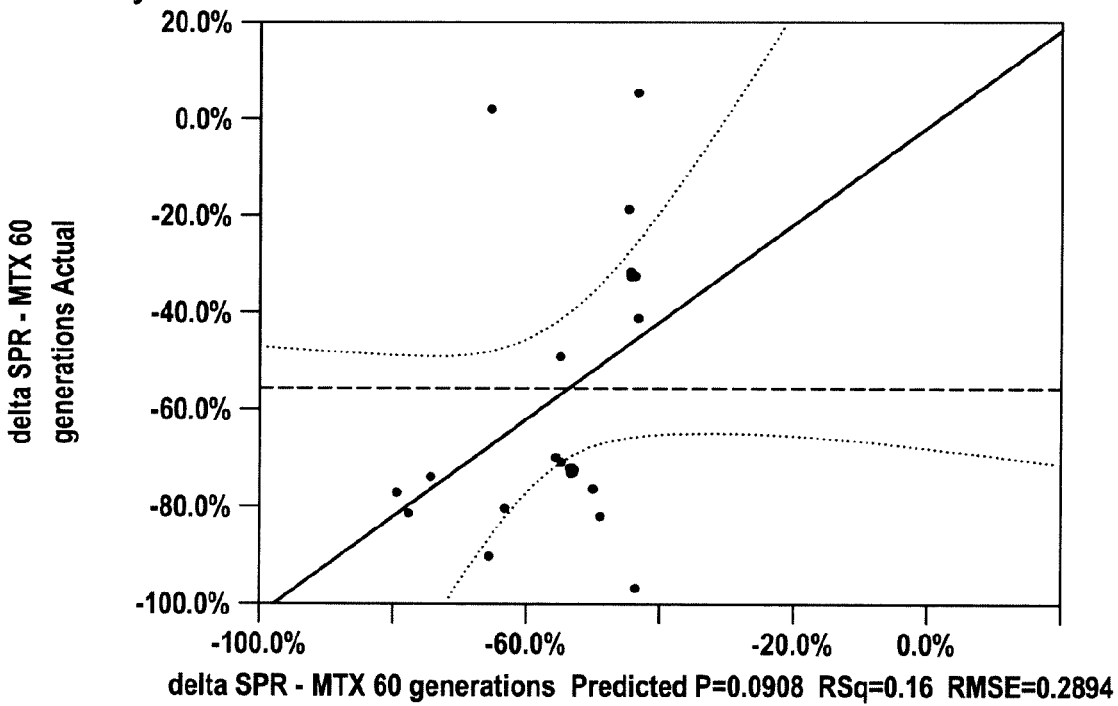

METHOD FOR THE SELECTION OF A LONG-TERM PRODUCING CELL USING HISTONE ACYLATION AS MARKERS

CROSS-REFERENCE TO RELATED APPLICATIONS

This application is a § 371 national phase application of International Application No. PCT/EP2015/060593 having an international filing date of May 13, 2016, the entire contents of which are incorporated herein by reference, and which claims benefit under 35 U.S. § 119 to European Patent Application No. 14168896.0 filed on May 19, 2014.

SEQUENCE LISTING

This application contains a Sequence Listing which has been submitted electronically in ASCII format and is hereby incorporated by reference in its entirety. Said ASCII copy, created on Nov. 15, 2016, is named Sequence.Listing.txt and is 17,914 bytes in size.

The herein reported method is in the field of cell selection and polypeptide expression/production. In more detail, herein is reported a method for the selection of a long-term polypeptide expressing or secreting cell based on the determination of histone acylation.

BACKGROUND OF THE INVENTION

DNA is a macromolecule that encodes the instructions of all known living organisms (Avery, O. T., et al., J. Exp. Med. 79 (1944) 137-158). In human cells DNA has a length of approximately two meters and is mostly stored in the nucleus which has a diameter of 10 µm (Turner, B. M., Cell 111 (2002) 285-291). To organize this amount of information the DNA needs to be highly compacted. A group of conserved small basic proteins called histones form complexes with DNA to generate an ordered and compact structure termed chromatin. Those positively charged proteins interact with the negatively charged phosphodiester backbone of the DNA double helix (Alberts, B. J. A., et al., Molecular Biology of the Cell; Meyers, R. A., Epigenetic Regulation and Epigenomics, WILEY-BLACKWELL, 1; Olins, E. D., Nat. Rev. Mol. Cell Biol. (2003)). The four "core" histones H2A, H2B, H3 and H4 combine with DNA to form the basic repeating unit of chromatin, called the nucleosome (Thomas, J. O. and Kornberg, R. D., Proc. Natl. Acad. Sci. USA 72 (1975) 2626-2630). The 225 kDa nucleosome core structure consists of approximately 147 bp of DNA wrapped around a histone octamer, comprising two H2A/H2B dimers and a H3/H4 tetramer in 1.67 left-handed superhelical turns (Arents, G., et al., Proc. Natl. Acad. Sci. USA 88 (1991) 10148-10152; Arents, G. and Moudrianakis, E. N., Proc. Natl. Acad. Sci. USA 90 (1993), 10489-10493; Richmond, T. J., Scientist 13 (1999) 15-15). Depending on the accessibility of DNA, chromatin is distinguished into two types. Highly compacted heterochromatin, which is less accessible for transcription, and loosely-packed transcriptionally-active euchromatin. Facultative heterochromatin can form anywhere in the nucleus, often localized to promoters, and is established either in a developmentally regulated manner or in response to environmental triggers (Chen, T. and Dent, S. Y., Nat. Rev. Genet. 15 (2014), 93-106).

The gradual loss of productivity in long-term culture is a common issue with the development of manufacturing cell lines. The decrease of recombinant protein expression can be due to a loss of transgene copies and/or silencing of the transgene promoter. Silencing is caused by epigenetic modifications of chromatin such as direct methylation of promoter DNA at CpG sites and posttranslational modifications of histones which are the major protein components of chromatin. Inactivating modifications of histones are counteracted by other modifications that are activating.

Barnes, L. M., et al., report the molecular definition of predictive indicators of stable protein expression in recombinant NS0 myeloma cells (Biotechnol. Bioeng. 85 (2004) 115-121). The correlation reported by Barnes et al. is weak and not sufficient for a stability prediction.

In WO 2004/056986 means and methods for producing a protein through chromatin openers that are capable of rendering chromatin more accessible to transcription factors are reported.

In WO 2011/128377 it has been reported that direct methylation of the human cytomegalovirus major-immediately-early promoter (hCMV MIE) can be used as early marker to predict production instability of recombinant CHO cell lines.

Osterlehner, A., et al., report promoter methylation and transgene copy numbers predict unstable protein production in recombinant Chinese hamster ovary cell lines (Biotechnol. Bioeng. 108 (2011) 2670-2681).

SUMMARY OF THE INVENTION

It has been found that the determination of the degree of methylation of a specific CpG site in the promoter nucleic acid operably linked to a structural gene encoding a polypeptide in a cell or cell line used for the production of the respective polypeptide in combination with the determination of histone acylation close to the promoter, i.e. in the promoter chromatin, can be used to predict a decrease in productivity during long-term cultivation. Additionally the copy number of the light chain expression cassette integrated into the genome can be determined.

One aspect as reported herein is a method for selecting a cell clone/cell line, which comprises a nucleic acid comprising a structural gene encoding a polypeptide operably linked to a promoter nucleic acid, comprising the following steps:
  a) determining the (relative) level of histone 3 acetylation relative to the level of histone 3 (H3ac/H3) close to the promoter nucleic acid for a first multitude of cell clones/cell lines, and
  b) selecting a cell clone/cell line, which comprises a nucleic acid comprising a structural gene encoding a polypeptide operably linked to a promoter nucleic acid that has a (relative) level of histone 3 acetylation relative to the level of histone 3 as determined in step a) of 0.1 or more.

One aspect as reported herein is a method for selecting a cell clone/cell line, which comprises a nucleic acid comprising a structural gene encoding a polypeptide operably linked to a promoter nucleic acid comprising the following steps:
  a) determining for each cell clone/cell line of a first multitude of cell clones/cell lines, whereby each clone/cell line comprises a nucleic acid comprising a structural gene encoding a polypeptide operably linked to a promoter nucleic acid, the average (relative) level of histone 3 acetylation relative to the level of histone 3 (H3ac/H3) close to the promoter nucleic acid based on the (relative) level of histone 3 acetylation relative to the level of histone 3 (H3ac/H3) determined in at least 10 cells obtained from a cultivation of each cell clone/cell line, and b) selecting a cell clone/cell line that has an average (relative) level of histone 3 acetylation relative to the level of histone 3 (H3ac/H3) of 0.1 or more.

One aspect as reported herein is a method for selecting a cell clone/cell line, which comprises a nucleic acid comprising a structural gene encoding a polypeptide operably linked to a promoter nucleic acid that has the nucleic acid sequence of SEQ ID NO: 01 comprising the following steps:

a) determining the (relative) level of histone 3 acetylation relative to the level of histone 3 (H3ac/H3) close to the promoter nucleic acid that has the nucleotide sequence of SEQ ID NO: 01 for each clone of a first multitude of cell clones/cell lines, and b) determining the methylation frequency of the CpG-site at position 425 of SEQ ID NO: 01 for each clone of a second multitude of cell clones/cell lines, and c) selecting a cell clone/cell line, which comprises a nucleic acid comprising a structural gene encoding a polypeptide operably linked to a promoter nucleic acid that has the nucleic acid sequence of SEQ ID NO: 01, that has a (relative) level of histone 3 acetylation relative to the level of histone 3 as determined in step a) of 0.1 or more, and that has a methylation frequency of the CpG-site at position 425 as determined in step b) of less than 5%.

One aspect as reported herein is a method for selecting a cell clone/cell line, which comprises a nucleic acid comprising a structural gene encoding a polypeptide operably linked to a promoter nucleic acid that has the nucleic acid sequence of SEQ ID NO: 01 comprising the following steps:

a) determining for each cell clone/cell line of a first multitude of cell clones/cell lines, whereby each clone/cell line comprises a nucleic acid comprising a structural gene encoding a polypeptide operably linked to a promoter nucleic acid that has the nucleic acid sequence of SEQ ID NO: 01, the average (relative) level of histone 3 acetylation relative to the level of histone 3 (H3ac/H3) close to the promoter nucleic acid that has the nucleotide sequence of SEQ ID NO: 01 based on the (relative) level of histone 3 acetylation relative to the level of histone 3 (H3ac/H3) determined in at least 10 cells obtained from a cultivation of each cell clone/cell line, b) determining for each cell clone/cell line of a second multitude of cell clones/cell lines, whereby each clone/cell line comprises a nucleic acid comprising a structural gene encoding a polypeptide operably linked to a promoter nucleic acid that has the nucleic acid sequence of SEQ ID NO: 01, the average methylation frequency of the CpG-site at position 425 of SEQ ID NO: 01 based on the methylation determined for at least 10 cells obtained from a cultivation of each cell clone/cell line, c) selecting a cell clone/cell line that has an average (relative) level of histone 3 acetylation relative to the level of histone 3 (H3ac/H3) of 0.1 or more, and that has a methylation frequency at position 425 below 5%.

In one embodiment the (relative) level of histone 3 acetylation relative to the level of histone 3 is 0.2 or more. In one embodiment the (relative) level of histone 3 acetylation relative to the level of histone 3 is 0.5 or more. In one embodiment the (relative) level of histone 3 acetylation relative to the level of histone 3 is 0.75 or more. In one embodiment the (relative) level of histone 3 acetylation relative to the level of histone 3 is 1.0 or more.

In one preferred embodiment the (relative) level of histone 3 acetylation relative to the level of histone 3 is 0.5 or more.

In one embodiment the promoter nucleic acid has the sequence of SEQ ID NO: 01 or comprises a functional fragment thereof or a functional variant thereof. In one embodiment the CpG-site is at position 425 of SEQ ID NO: 01 or a thereto corresponding position in the fragment or variant thereof.

In one embodiment of all aspects the method further comprises the following step:

ab) determining the (copy) number of stably integrated light chain expression cassettes,
whereby step c) is:
selecting a cell clone/cell line that has a level of histone 3 acetylation relative to the level of histone 3 as determined in step a) of more than 0.5, that has a methylation frequency of the CpG-site at position 425 as determined in step b) of less than 5%, and that has a (copy) number of stably integrated light chain expression cassettes as determined in step ab) of 10 or less.

In one preferred embodiment the copy number of stably integrated light chain expression cassettes as determined in step ab) is 6 or less.

In one embodiment the average (relative) level of histone 3 acetylation is the average (relative) level of histone 3 acetylation at the lysine residues at position 4 and/or 9 and/or 14 and/or 18 and/or 27. In one embodiment the lysine residues are at position 9 and/or 14 and/or 27.

In one embodiment of all aspects the method comprises as first step:

transfecting a population of cells with a nucleic acid comprising a structural gene encoding a polypeptide operably linked to a promoter nucleic acid that has the nucleic acid sequence of SEQ ID NO: 01, and obtaining therefrom a first and a second and optionally a third multitude of cell clones/cell lines.

In one embodiment the (selected) cell line has a production rate after 30-60 generations in cultivation of more than 60% of the production rate at the beginning of the cultivation.

One aspect as reported herein is a method for selecting a cell clone/cell line, which comprises a nucleic acid comprising a structural gene encoding at least an antibody light chain operably linked to a promoter nucleic acid that has the nucleic acid sequence of SEQ ID NO: 01 comprising the following steps:

a) determining the (relative) level of histone 3 acetylation relative to the level of histone 3 (H3ac/H3) close to the promoter nucleic acid that has the nucleotide sequence of SEQ ID NO: 01 for each clone of a first multitude of cell clones/cell lines, and b) determining the (copy) number of stably integrated light chain expression cassettes for each clone of a second multitude of cell clones/cell lines, and c) determining the methylation frequency of the CpG-site at position 425 of SEQ ID NO: 01 for each clone of a third multitude of cell clones/cell lines, and d) selecting a cell clone/cell line, which comprises a nucleic acid comprising a structural gene encoding a polypeptide operably linked to a promoter nucleic acid that has the nucleic acid sequence of SEQ ID NO: 01, i) that has a (relative) level of histone 3 acetylation relative to the level of histone 3 as determined in step a) of 0.1 or more, ii) that has a methylation frequency of the CpG-site at position 425 as determined in step b) of less than 5%, and iii) that has a (copy) number of stably integrated light chain expression cassettes as determined in step ab) of 10 or less.

One aspect as reported herein is a method for selecting a cell clone/cell line, which comprises a nucleic acid comprising a structural gene encoding at least an antibody light chain operably linked to a promoter nucleic acid that has the nucleic acid sequence of SEQ ID NO: 01 comprising the following steps:
  a) determining for each cell clone/cell line of a multitude of cell clones/cell lines, whereby each clone/cell line comprises a nucleic acid comprising a structural gene encoding a polypeptide operably linked to a promoter nucleic acid that has the nucleic acid sequence of SEQ ID NO: 01, the average (relative) level of histone 3 acetylation relative to the level of histone 3 (H3ac/H3) close to the promoter nucleic acid that has the nucleotide sequence of SEQ ID NO: 01 based on the (relative) level of histone 3 acetylation relative to the level of histone 3 (H3ac/H3) determined in at least 10 cells obtained from a cultivation of each cell clone/cell line,
  b) determining for each cell clone/cell line of the multitude of cell clones/cell lines the (copy) number of stably integrated light chain expression cassettes in at least 10 cells obtained from a cultivation of each cell clone/cell line, and
  c) determining for each cell clone/cell line of the multitude of cell clones/cell lines, whereby each clone/cell line comprises a nucleic acid comprising a structural gene encoding a polypeptide operably linked to a promoter nucleic acid that has the nucleic acid sequence of SEQ ID NO: 01, the average methylation frequency of the CpG-site at position 425 of SEQ ID NO: 01 based on the methylation determined for at least 10 cells obtained from a cultivation of each cell clone/cell line,
  d) selecting a cell clone/cell line i) that has an average (relative) level of histone 3 acetylation relative to the level of histone 3 (H3ac/H3) of 0.1 or more, ii) that has a methylation frequency at position 425 below 5%, and iii) that has a (copy) number of stably integrated light chain expression cassettes as determined in step ab) of 10 or less.

In one embodiment the (relative) level of histone 3 acetylation relative to the level of histone 3 is 0.2 or more. In one embodiment the (relative) level of histone 3 acetylation relative to the level of histone 3 is 0.5 or more. In one embodiment the (relative) level of histone 3 acetylation relative to the level of histone 3 is 0.75 or more. In one embodiment the (relative) level of histone 3 acetylation relative to the level of histone 3 is 1.0 or more.

In one preferred embodiment the (relative) level of histone 3 acetylation relative to the level of histone 3 is 0.5 or more.

In one embodiment the average (relative) level of histone 3 acetylation is the average (relative) level of histone 3 acetylation at the lysine residues at position 4 and/or 9 and/or 14 and/or 18 and/or 27. In one embodiment the lysine residues are at position 9 and/or 14 and/or 27.

In one embodiment the promoter nucleic acid has the sequence of SEQ ID NO: 01 or comprises a functional fragment thereof or a functional variant thereof. In one embodiment the CpG-site is at position 425 of SEQ ID NO: 01 or a thereto corresponding position in the fragment or variant thereof.

In one preferred embodiment the (copy) number of stably integrated light chain expression cassettes as determined in step b) is 6 or less.

In one embodiment the determining of the (relative) level of histone 3 acetylation relative to the level of histone 3 (H3ac/H3) comprises the following steps:
  1) isolating chromatin from each of the cell clones/cell lines,
  2) treating a first aliquot of the chromatin by an antibody that is suitable to determine the (relative) level of histone 3 acetylation, such as e.g. a histone 3 acetylation specific antibody, and forming an antibody-chromatin precipitate, and treating a second aliquot of the chromatin by an antibody that is suitable to determine the level of histone 3, such as e.g. a histone 3 specific antibody, and forming and antibody-chromatin precipitate,
  3) amplifying genomic DNA from a third not-treated aliquot of the chromatin and from the first and second treated aliquot with real time quantitative PCR,
  4) determining with the result obtained in step 3) the (relative) level of histone 3 acetylation relative to the level of histone 3.

In one embodiment the determining of the methylation frequency comprises the following steps:
  1) isolating the DNA from each of the cell clones/cell lines,
  2) performing for each isolated DNA individually a methylation specific polymerase chain reaction,
  3) determining with the results obtained in step 2) the methylation frequency.

In one embodiment step 2) is
  2) performing for each isolated DNA individually a polymerase chain reaction with a methylation specific primer and a universal primer.

In also an embodiment step 2) is
  2) individually digesting the isolated DNA with a restriction enzyme and performing a polymerase chain reaction for each of the digested DNA with a methylation specific primer and a universal primer.

In one embodiment the primers are independently of each other selected from the group consisting of SEQ ID NO: 06 to 20.

In one embodiment a primers is selected from the group consisting of SEQ ID NO: 11, 14 and 15, the universal primer has the sequence of SEQ ID NO: 09, and a methylation specific primer is selected from the group consisting of SEQ ID NO: 17, 18 and 19.

In one embodiment the universal primers have the sequence of SEQ ID NO: 09 and 11 and the methylation specific primers have the sequence of SEQ ID NO: 11 and 18.

In one embodiment the (relative) level of histone 3 acetylation relative to the level of histone 3 (H3ac/H3) is normalized to a reference gene. In one embodiment the reference gene is Gusb.

In one embodiment the second multitude of cell clones/cell lines comprises at least one cell clone/cell line also comprised in the first multitude of cells clones/cell lines. In one embodiment the second multitude of cell clones/cell lines is identical to the first multitude of cells clones/cell lines.

In one embodiment the cell clone/cell line is a eukaryotic cell clone/cell line. In one embodiment the cell clone/cell line is a mammalian cell clone/cell line. In one embodiment the cell clone/cell line is selected from CHO, BHK, HEK, and Sp2/0. In one embodiment the cell clone/cell line is a CHO cell clone/cell line. In one embodiment the cell clone/cell line is a CHO K1 cell clone/cell line.

In one preferred embodiment the cell clone/cell line is a CHO cell clone/cell line.

In one embodiment the polypeptide is i) an antibody, or ii) an antibody fragment, or iii) an antibody conjugate, or iv) an antibody light chain and an antibody heavy chain. In one embodiment the antibody is a bispecific antibody.

One aspect as reported herein is a method for the production of a polypeptide comprising the following steps:
a) selecting a cell clone/cell line with a method as reported herein,
b) cultivating the selected cell clone/cell line, and
c) recovering the polypeptide from the cultivation medium and/or the cell clone/cell line and thereby producing the polypeptide.

In one embodiment the method comprises prior to step a) the following steps:
a-3) providing a mammalian, non-human cell,
a-2) transfecting the provided cell with a nucleic acid, which comprises a nucleic acid comprising a structural gene encoding a polypeptide operably linked to a promoter nucleic acid that has the nucleic acid sequence of SEQ ID NO: 01,
a-1) i) optionally cultivating the transfected cell clone/cell line in the presence of a selection agent, ii) single depositing the transfected cells, and iii) cultivating the single deposited transfected cells in the presence of a selection agent.

One aspect as reported herein is a method for the production of a polypeptide comprising the following steps:
a) selecting a cell clone/cell line with a method as reported herein,
b) cultivating the selected cell/clone, and
c) recovering the polypeptide from the cultivation medium and/or the cells and thereby producing a polypeptide.

In one embodiment the method comprises a further step d) purifying the recovered polypeptide.

In one embodiment the method comprises prior to step a) the following steps:
a-3) providing a cell,
a-2) transfecting the provided cell with a nucleic acid containing a structural gene encoding the polypeptide operably linked to a promoter nucleic acid,
a-1) i) optionally cultivating and propagating the transfected cell in the presence of a selection agent, ii) single depositing the cells, and iii) cultivating the single deposited transfected cells in the presence of a selection agent.

In one embodiment step a) comprises:
i) providing at least one cell comprising a nucleic acid comprising a structural gene encoding the polypeptide operably linked to a promoter nucleic acid,
ii) determining the methylation of the CpG-site at position 425 within the promoter nucleic acid of SEQ ID NO: 01, and
iii) selecting a cell producing a polypeptide wherein the methylation determined in step b) is below a threshold value.

DETAILED DESCRIPTION OF THE INVENTION

Economic cell lines are required to provide high productivity and stable production levels during propagation from small to large scale. Decrease of productivity during scale-up constitutes a serious risk during cell line development (Barnes, L. M., et al., Biotechnol. Bioeng. 81 (2003) 631-639). One main reason for production instability is a reduction of active copy numbers over cell cycles, which might be attributed to chromosomal disruption/rearrangement as an inherent characteristic of CHO cells (Kim, M., et al., Biotechnol. Bioeng. 108 (2011) 2434-2446.) and/or an induction by the gene amplification process (Kaufman, R. J., et al., Mol. Cell. Biol. (1983) 699-711). The decrease of mRNA at a constant number of copies of recombinant genes is another major cause of productivity drop (Barnes, L. M., et al., Biotechnol. Bioeng. 85 (2004) 115-121; Chusainow, J., et al., Biotechnol. Bioeng. 102 (2009) 1182-1196; Strutzenberger, K., et al., J. Biotechnol. 69 (1999) 215-226). A reasonable explanation for this occurrence is epigenetic silencing by promoter methylation (Osterlehner, A., et al., Biotechnol. Bioeng. 108 (2011) 2670-2681; Yang, Y., et al., J. Biotechnol. 147 (2010) 180-185) and histone modifications as typified by deacetylation and specific methylation (Mutskov, V. and Felsenfeld, G., EMBO J. 23 (2004) 138-149; Paredes, V., et al., Biotechnol. Lett. 35 (2013) 987-993). Also, the recombinant sequence itself, the formation of tandem repeats of sequence and the genomic location of transgene are proposed initiators for gene silencing (Kaufman, W. L., et al., Nuc. Acids Res. 36 (2008) e111). From this the influence of adjacent chromatin onto integration sites is termed 'position effect' (Lattenmayer, C., et al., Cytotechnol. 51 (2006) 171-182; Yin, Z., et al., Genet. Mol. Res. 11 (2012) 355-369).

The promoter upstream of the recombinant gene initiates gene transcription and is able to affect gene expression level and stability (Kaufman, W. L., et al., Nuc. Acids Res. 36 (2008) e111). The major immediate early gene promoter of the human cytomegalovirus (hCMV-MIE) is commonly used to drive recombinant expression in mammalian cells for research and manufacturing to obtain high expression levels in transient and stable transfections (Boshart, M., et al., Cell 41 (1985) 521-530; Chapman, B. S., et al., Nuc. Acids Res. 19 (1991) 3979-3986; Foecking, M. K. and Hofstetter, H. Gene 45 (1986) 101-105; Wright, A., et al., Hum. Gene Ther. 16 (2005) 881-892). Although the hCMV-MIE promoter provides high gene expression levels, many studies have reported a decrease of productivity over long-term culture (Bailey, L. A., et al., Biotechnol. Bioeng. 109 (2012) 2093-2103; Barnes, L. M., et al., Biotechnol. Bioeng. 73 (2001) 261-270; He, L., et al., Biotechnol. Bioeng. 109 (2012) 1713-1722.). The silencing of the hCMV-MIE promoter is (in addition to the loss of copy numbers) largely attributed to epigenetic events of promoter DNA methylation and histone modification (Brooks, A. R., et al., J. Gene Med. 6 (2004) 395-404.; Kim, M., et al., Biotechnol. Bioeng. 108 (2011) 2434-2446; Osterlehner, A., et al., Biotechnol. Bioeng. 108 (2011) 2670-2681; Paredes, V., et al., Biotechnol. Lett. 35 (2013) 987-993; Yang, Y., et al., J. Biotechnol. 147 (2010) 180-185).

Chromatin is known to be involved in the regulation of gene expression. The modification of the DNA or of chromatin and/or chromatin-associated proteins, such as histones, has an impact on chromatin structure and hence gene expression. DNA modification in mammalian cells can be by methylation of cytosine residues in CpG dinucleotides. Histones, especially their N-terminal portion, can be modified by acetylation, methylation, phosphorylation or ubiquitinylation.

The nucleic acid content of a cell, i.e. its DNA, is present in the cell nucleus in compacted form together with histones. Histones pack and order the DNA into nucleosomes. There are five main histone proteins in humans. Histones are highly alkaline proteins. Histone H3 (histone 3) has a main globular domain and an N-terminal tail. It has a size of 137 amino acid residues. Histones in general have the function of providing a core structure around which the DNA is located and regulate gene expression.

Histones can be modified in many different ways, mainly occurring along the residues of the N-terminal amino acid sequence which ranges from 13 to 40 amino acids in length depending on the specific histone. This large number of modifications even increases due to the fact that some modifications like lysine methylation comprise up to three different states (Kouzarides, T., Cell 128 (2007) 693-705). More than 100 histone modifications have been discovered (Zentner, G. E. and Henikoff, S., Nat. Struct. Mol. Biol. 20 (2013) 259-266). Acetylation and methylation of histone H3 and histone H4 tail residues are the best studied modifications. Overall, 14 distinctive types of modifications have been found (Dawson, M. A. and Kouzarides, T., Cell 150 (2012) 12-27) and are listed in the following Table.

TABLE 1

| Chromatin Modifications | Modified Residues | Chromatin Modifications | Modified Residues |
|---|---|---|---|
| acetylation | K-ac | Proline isomerization | P-cis > P-trans |
| methylation (lysines) | K-me1, K-me2, K-me3 | crotonylation | K-cr |
| methylation (arginines) | R-me1, R-me2a, R-me2s | propionylation | K-pr |
| phosphorylation | S-ph, T-ph | butyrylation | K-bu |
| ubiquitinylation | K-ub | formylation | K-fo |
| sumoylation | K-su | hydroxylation | Y-oh |
| ADP ribosylation | E-ar | O-GlcNAcylation (serine and threonine) | S-GlcNAc; T-GlcNAc |
| deimination | R > Cit | | |

K, lysine;
R, arginine;
S, serine;
T, threonine;
E, glutamic acid;
P, proline;
ac, acetylation;
me, methylation;
cit, citrulline;
cr, crotonylation;
pr, propionylation;
bu, butyrylation;
fo, formylation;
oh, hydroxylation;
a, asymmetric;
s, symmetric;
>, conversion.
Adopted from (Dawson & Kouzarides, 2012).

The combination of these modifications, termed as PTM (post translational modification) motifs are rather associated with functions than the individual marks. Research into combination of modifications suggests more than 200 different PTM motifs (Feller, C., et al., Mol. Cell 57 (2015) 559-571). Modifications are reversible.

It is known that methylation of histone H3 at lysine 9 (H3K9) and 27 (H3K27) are modifications resulting in gene repression. Histone modifications seem to provide labile transcriptional repression whereas DNA methylation being a highly stable silencing mark that is not easily reversed (Cedar, H. and Bergman, Y., Nat. Rev. Gen. 10 (2009) 295-304).

Histone acetylation was discovered in 1961 as the first histone modification (Phillips, D. M., Biochem. J. 87 (1963) 258-263). Early studies associate active transcribed genes with the hyperacetylation of histones, which indicates a function of acetylation in the transcription process (Allfrey, V. G., et al., Proc. Natl. Acad. Sci. USA 51 (1964) 786-794). During S-phase a global increase of acetylation sites, such as H3K56ac, was observed followed by a decrease during G2-phase. This led to the conclusion that histone acetylation might facilitate the incorporation of newly synthesized histones (Miller, K. M., et al., Cell Cycle 5 (2006) 2561-2565). In addition to their global role during DNA replication, histone acetylation form specific genomic patterns correlating with active transcription. Thereby heterochromatin regions are hypoacetylated and euchromatin transcriptionally active genes are highly acetylated (Kouzarides, T., Cell 128 (2007) 693-705). Acetylation peaks are found at specific sites in the promoter close to transcription start sites (TSS) (Wang, Z., et al., Nat. Genet. 40 (2008) 897-903). The histone lysine residues of the N-terminal tail of histone 3 at position 4, 9, 14, 18 and of histone 4 at lysines 5, 8, and 12 are predominantly prone to acetylation. Taken together, regulation of gene expression, DNA replication, repair and recombination are influenced by different acetylation states of histones (Dawson, M. A. and Kouzarides, T., Cell 150 (2012) 12-27).

Histone acetyltransferases (HATS) generally mediate gene expression and transcriptional activation (Cheung, P., et al., Cell 103 (2000) 263-271). Using chromatin immunoprecipitation it has been found that non-methylated DNA is mostly assembled in nucleosomes that contain acetylated histones, which are associated with open chromatin, whereas the presence of methyl groups on identical DNA sequences correlates with assembly of nucleosomes containing non-acetylated histone H3 and H4 leading to more compact chromatin (Cedar, H. and Bergman, Y., Nat. Rev. Gen. 10 (2009) 295-304; Eden, S., et al., Nature 394 (1998) 842-843; Hashimshony, T., et al., Nat. Gen. 34 (2003) 187-192). Histone H3 is the most excessively modified histone of the five naturally occurring histones.

In regions of high transcriptional activity a high degree of histone acetylation can be found. Histone acetylation is catalyzed by the enzyme histone-acetyl-transferase (HAT) which transfers the acetyl part of acetyl-CoA to the ε-amino group of specific histone lysine residues in the N-terminal region. Histone acetylation takes exclusively place at lysine residues, such as e.g. H3K9 (lysine at position 9 of histone 3), H3K14, and H3K27 (Koch, C. M., et al., Gen. Res. 17 (2007) 691-707; Creyghton, M. P., et al., Proc. Natl. Acad. Sci. USA 107 (2010) 21931-21936).

It is commonly observed during cell line development and in large scale production that silencing of recombinant gene expression during prolonged (large scale) host cell cultivation occurs. In mammalian cells this can be due e.g. to the formation of chromatin derivatives, which prevents the transcription of the recombinant gene.

This results in a heterogeneous cell population after longer cultivation times, such as in large scale production (including seed train fermentations and main fermentation). In this heterogeneous cell population some cells continue to express high levels of the recombinant protein of interest while other cells express low or even no protein of interest (see e.g. Martin, D. I. and Whitelaw, E., Bioessays 18, (1996) 919-923; McBurney, M. W., et al., Exp. Cell. Res. 274 (2002) 1-8).

Production cell lines are in general descendants from a single parent cell. These cells are often scaled up during cultivation and cultivated for a long time in large scale fermentations (seed train and production fermentations) resulting in cultivation volumes of up to 25,000 liter and cell densities of often more than one million cells per milliliter. Such large scale fermentations can show dramatic reductions in productivity (Migliaccio, A. R., et al., Gene 256 (2000) 197-214; Strutzenberger, K., et al., J. Biotechnol. 69 (1999) 215-226).

For the selection of production cell lines/cell clones, i.e. cell clone/cell lines that are intended to be used for the large scale recombinant production of a polypeptide, such as e.g. an antibody, the production/expression stability, i.e. the loss of productivity generation by generation, of the cell clone/cell line is important. Thus, mammalian cell lines for recombinant protein production need to maintain productivity over extended cultivation times. Generally the production stability of a cell clone/cell line is determined by cultivating the cell clone/cell line over a long period of time, i.e. multiple generations. At regular intervals the medium is diluted with fresh medium and the specific productivity per cell is determined based on the product titer and the viable cell density. The change (normally a reduction) of the specific productivity is indicative of long term production stability of the cell clone/cell line.

Long term stability studies are time and resource intensive, but are widely performed to identify and eliminate unstable candidates during cell line development. Depending on the target criteria the study covers 30 to 60 cell divisions, which corresponds generally to 30 to 70 days. Thus, the required material and working time is pronounced. This can be seen even more by the fact that up to 75% of the tested cell lines/cell clones are not stable and, thus, a high number of cell lines/cell clones has to be assessed.

Beside the loss of the transgene production instability of manufacturing cell lines can be associated with methylation and silencing of the heterologous promoter used for the expression of the transgene (see e.g. Escher, G., et al. J. Lipid Res. 46 (2005) 356-365; Krishnan, M., et al., FASEB J. 20 (2006) 106-108; Yang, Y., et al., J. Biotechnol. 147 (2010) 180-185). Promoter silencing can result from epigenetic modification of the chromatin (combination or complex of DNA and proteins that make up the contents of the nucleus of a cell). This can be the direct methylation of CpG dinucleotides within the promoter, such as e.g. the human cytomegalovirus major-immediate-early promoter/enhancer (hCMV MIE), and/or the posttranslational modification of histones. Besides inactivating histone modifications, such as the methylation of lysine 9 or 27 of histone 3, activating modifications, such as the methylation of lysine 4 of histone 3, or the global acetylation of histone 3 and 4, are known (see e.g. Cedar, H. and Bergman, Y., Nat. Rev. Genet. 10 (2009) 295-304).

The epigenetic modification of CpG methylation of the hCMV-MIE promoter was used as an indicator for long-term production stability (see Osterlehner et al.).

Herein local lysine acetylation (H3ac) as potential prediction markers of long-term transgene silencing was identified.

It has been found that the CpG dinucleotide at position 425 of the human CMV major-immediate-early (hCMV) promoter/enhancer (SEQ ID NO: 01) is frequently methylated in unstable antibody-producing Chinese hamster ovary (CHO) cell lines. A methylation-specific real-time qPCR has been established to allow for the rapid and sensitive measurement of hCMV-MIE methylation.

It has further been found that the posttranslational modification of histone adjacent to the promoter can be used as further marker to identify stable expressing/producing cell lines. The presence of an inactivating modification is a marker that the respective cell clone/cell line is very instable and will show a decline in productivity during the future course of the cultivation that is above average (long term instable producing cell clone/cell line). On the other hand the presence of an activating modification is a marker that the respective cell clone/cell line is very stable and will show a decline in productivity during the future course of the cultivation that is below average (long term stable producing cell clone/cell line).

It has been found that by using a combination of both above markers, i.e. the methylation at position 425 of SEQ ID NO: 01 and the relative level of histone 3 acetylation relative to the level of histone 3 (H3ac/H3) close to the promoter nucleic acid a further improvement in the determination of long term stable producing recombinant cell lines/cell clones can be achieved. A further improvement is possible if also the (copy) number of stably integrated light chain expression cassettes is included in case of an antibody.

Thus, herein are reported methods for the selection of a cell clone/cell line as well as a method for the production of a polypeptide using such a cell clone/cell line. The selected cell clone/cell line is a long-term producing cell. Such a cell clone/cell line can be selected as reported herein based i) on the relative level of histone 3 acetylation relative to the level of histone 3 (H3ac/H3) close to the promoter nucleic acid, or ii) on the methylation of the human CMV major-immediate-early (hCMV MIE) promoter/enhancer at position 425 operably linked to the structural gene encoding the polypeptide, or iii) on a combination of i) and ii).

A. DEFINITIONS

The term "almost" denotes that the value following this expression is a center value with certain variability. In one embodiment the variability is of ±40% of the value, in another embodiment the variability is of ±30%, and in a further embodiment the variability is of ±20%. Thus, the term almost constant denotes that a value is in one embodiment in the range of from 60% to 140%, in another embodiment in the range of from 70% to 130%, and in a further embodiment in the range of from 80% to 120%.

The term "antibody" denotes a molecule comprising at least two so called light chain polypeptides (light chain) and two so called heavy chain polypeptides (heavy chain). Each of the heavy and light chain polypeptides comprises a variable domain (variable region) (generally the amino terminal portion of the polypeptide chain) comprising binding regions that are able to interact with an antigen. Each of the heavy and light chain polypeptides also comprises a constant region (generally the carboxy-terminal portion). The constant region of the heavy chain mediates the binding of the antibody i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component (C1q).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

Depending on the amino acid sequence of the constant region of the heavy chains, antibodies are divided in different classes: IgA class, IgD class, IgE class, IgG class, and IgM class. Some of these classes are further divided into subclasses (isotypes), i.e. IgG in IgG1, IgG2, IgG3, and IgG4, or IgA in IgA1 and IgA2. According to the class to which an antibody belongs the heavy chain constant regions are called α (IgA), δ (IgD), ε (IgE), γ (IgG), and μ (IgM), respectively. In one embodiment the antibody is an antibody of the IgG class. In another embodiment the antibody has a human constant region or a constant region derived from human origin. In a further embodiment the antibody is of the IgG4 subclass or the IgG1, IgG2, or IgG3 subclass, which is modified in such a way that no Fcγ receptor (e.g. FcγRIIIa) binding and/or no C1q binding can be detected. In one embodiment the antibody is of the human IgG4 subclass or a mutated human IgG1 subclass. In one embodiment the antibody is of the human IgG1 subclass with mutations L234A and L235A. In another embodiment the antibody is in regard to Fcγ receptor binding of IgG4 subclass or of IgG1 or IgG2 subclass, with a mutation in L234, L235, and/or D265, and/or contains the PVA236 mutation. In a further embodiment the antibody has a mutation selected from S228P, L234A, L235A, L235E, SPLE (S228P and L235E), and/or PVA236 (PVA236 means that the amino acid sequence ELLG (given in one letter amino acid code) from amino acid position 233 to 236 of IgG1 or EFLG of IgG4 is replaced by PVA). In one embodiment the antibody is of the IgG4 subclass and has the mutation S228P of IgG4, or the antibody is of the IgG1 subclass and has the mutations L234A and L235A.

The variable domain of an immunoglobulin's light or heavy chain in turn comprises different segments, i.e. four framework regions (FR) and three hypervariable regions (CDR).

The term "bisulfite treatment" denotes a reaction for the conversion of cytosine bases in a nucleic acid to uracil bases in the presence of bisulfite ions whereby 5-methyl-cytosine bases are not significantly converted. This reaction for the detection of methylated cytosine is described in detail by Frommer et al. (Frommer, M., et al., Proc. Natl. Acad. Sci. USA 89 (1992) 1827-1831) and Grigg and Clark (Grigg, G. W. and Clark, S., Bioessays 16 (1994) 431-436; Grigg, G. W., DNA Seq. 6 (1996) 189-198). The bisulfite reaction contains a deamination step and a desulfonation step which can be conducted separately or simultaneously. The statement that 5-methyl-cytosine bases are not significantly converted shall only take the fact into account that it cannot be excluded that a small percentage of 5-methyl-cytosine bases is converted to uracil although it is intended to convert only and exclusively the (non-methylated) cytosine bases.

The term "cell" denotes a cell into which a nucleic acid, e.g. encoding a, optionally heterologous, polypeptide, can be or is introduced/transfected. The term "cell" includes both prokaryotic cells, which are used for propagation of plasmids, and eukaryotic cells, which are used for the expression of a nucleic acid. In one embodiment the cell is a eukaryotic cell and in a further embodiment the eukaryotic cell is a mammalian cell. In another embodiment the mammalian cell is selected from the group of mammalian cells comprising CHO cells (e.g. CHO K1, CHO DG44), BHK cells, NS0 cells, SP2/0 cells, HEK 293 cells, HEK 293 EBNA cells, PER.C6® cells, and COS cells. As used herein, the expression "cell" includes the subject cell and its progeny. Thus, the term "cell" denotes the primary subject cell and cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

The term "CpG-site" denotes the dinucleotide CG within a nucleic acid that can be recognized by the methylating enzymes of a cell and wherein the cytosine can be converted to 5-methyl cytosine. In one embodiment the CpG-site is within a promoter nucleic acid.

The term "expression cassette" denotes a construct that contains the necessary regulatory elements, such as promoter and polyadenylation site, for expression of at least the contained nucleic acid in a cell.

The term "expression plasmid" denotes a nucleic acid providing all required elements for the expression of the comprised structural gene(s) in a cell. Typically, an expression plasmid comprises a prokaryotic plasmid propagation unit, e.g. for E. coli, comprising an origin of replication, and a selection marker, an eukaryotic selection marker, and one or more expression cassettes for the expression of the structural gene(s) of interest each comprising a promoter nucleic acid, a structural gene, and a transcription terminator including a polyadenylation signal. Gene expression is usually placed under the control of a promoter nucleic acid, and such a structural gene is said to be "operably linked to" the promoter nucleic acid. Similarly, a regulatory element and a core promoter nucleic acid are operably linked if the regulatory element modulates the activity of the core promoter nucleic acid.

The term "generation time" denotes the time required by a cell to divide and to produce a daughter cell. Thus, a cell that has divided once has an age of one generation. The term "generation" denotes the number of cell division of a cell.

The term "high frequency" denotes that at this methylation site the cytosine is methylated more often than at other methylation sites based on the analysis of the methylation of a statistical significant number of individual cells or DNA clones, respectively. This statistical significant number is in one embodiment at least 10 individual cells or DNA clones, respectively, in a further embodiment at least 15 individual cells or DNA clones, respectively, and in another embodiment at least 20 individual cells or DNA clones, respectively. In one embodiment at maximum 400 cells or DNA clones, respectively, are analyzed.

The term "long-term producing cell" denotes a cell that produces a polypeptide, in one embodiment a heterologous polypeptide, whereby the specific production rate of the cell is almost constant for at least 30 generations. In one embodiment the long-term producing cell has a specific production rate that is almost constant for at least 30 generations, in another embodiment for at least 45 generations and in a further embodiment for at least 60 generations. In one embodiment the long-term producing cell has a specific production rate that is almost constant for up to 60 generations, in a further embodiment for up to 75 generations and in another embodiment for up to 90 generations.

The term "methylation" denotes a process within a cell that has been transfected with a nucleic acid comprising a structural gene encoding a polypeptide operably linked to a promoter in which a cytosine of the promoter nucleic acid is converted to 5-methyl cytosine. A promoter nucleic acid in which at least one cytosine is converted to 5-methyl cytosine is denoted as "methylated" nucleic acid.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein. In one embodiment the antibody is a monoclonal antibody.

The term "operably linked" denotes a juxtaposition of two or more components, wherein the components so described are in a relationship permitting them to function in their intended manner. For example, a promoter and/or enhancer are operably linked to a coding sequence, if it acts in cis to control or modulate the transcription of the linked sequence. Generally, but not necessarily, the DNA sequences that are "operably linked" are contiguous and, where necessary to join two protein encoding regions such as a secretory leader and a polypeptide, contiguous and in (reading) frame. However, although an operably linked promoter is generally located upstream of the coding sequence, it is not necessarily contiguous with it. Enhancers do not have to be contiguous. An enhancer is operably linked to a coding sequence if the enhancer increases transcription of the coding sequence. Operably linked enhancers can be located upstream, within or downstream of coding sequences and at considerable distance from the promoter. A polyadenylation site is operably linked to a coding sequence if it is located at the downstream end of the coding sequence such that transcription proceeds through the coding sequence into the polyadenylation sequence. A translation stop codon is operably linked to an exonic nucleic acid sequence if it is located at the downstream end (3' end) of the coding sequence such that translation proceeds through the coding sequence to the stop codon and is terminated there. Linking is accomplished by recombinant methods known in the art, e.g., using PCR methodology and/or by ligation at convenient restriction sites. If convenient restriction sites do not exist, then synthetic oligonucleotide adaptors or linkers are used in accord with conventional practice.

The term "polypeptide" denotes a polymer consisting of amino acids joined by peptide bonds, whether produced naturally or synthetically. Polypeptides of less than about 20 amino acid residues may be referred to as "peptides", whereas molecules consisting of two or more polypeptides or comprising one polypeptide of more than 100 amino acid residues may be referred to as "proteins". A polypeptide may also comprise non-amino acid components, such as carbohydrate groups, metal ions, or carboxylic acid esters. The non-amino acid components may be added by the cell, in which the polypeptide is expressed, and may vary with the type of cell. Polypeptides are defined herein in terms of their amino acid backbone structure or the nucleic acid encoding the same. Additions such as carbohydrate groups are generally not specified, but may be present nonetheless.

The term "variant" of a promoter nucleic acid denotes that within the promoter nucleic acid one or more nucleotides are changed without interfering with the function of the promoter nucleic acid. Such a change may be for removing or introducing a restriction site.

The term "producing" denotes the expression of a structural gene inserted into an expression cassette in a cell. The term includes the processes of transcription and translation of nucleic acid. Producing is performed in appropriate prokaryotic or eukaryotic cells and the expressed, i.e. produced, polypeptide can be recovered from the cells after lysis or from the culture supernatant.

The term, promoter nucleic acid" denotes a polynucleotide sequence that controls transcription of a gene/structural gene or nucleic acid sequence to which it is operably linked. A promoter nucleic acid includes signals for RNA polymerase binding and transcription initiation. The used promoter nucleic acid will be functional in the cell in which expression of the selected structural gene is contemplated. A large number of promoter nucleic acids including constitutive, inducible and repressible promoters from a variety of different sources are well known in the art (and identified in databases such as GenBank) and are available as or within cloned polynucleotides (from, e.g., depositories such as ATCC as well as other commercial or individual sources).

Typically, a promoter nucleic acid is located in the 5' non-coding or untranslated region of a gene, proximal to the transcriptional start site of the structural gene. Sequence elements within promoter nucleic acids that function in the initiation of transcription are often characterized by consensus nucleotide sequences. These elements include RNA polymerase binding sites, TATA sequences, CAAT sequences, differentiation-specific elements (DSEs), cyclic AMP response elements (CREs), serum response elements (SREs), glucocorticoid response elements (GREs), and binding sites for other transcription factors, such as CRE/ATF, AP2, SP1, cAMP response element binding protein (CREB) and octamer factors. If a promoter nucleic acid is an inducible promoter nucleic acid, then the rate of transcription increases in response to an inducing agent, such as a CMV promoter nucleic acid followed by two tet-operator site, the metallothionein and heat shock promoter nucleic acids. The rate of transcription is not regulated by an inducing agent if the promoter nucleic acid is a constitutively active promoter nucleic acid. Among the eukaryotic promoter nucleic acids that have been identified as strong promoter nucleic acids for expression are the SV40 early promoter nucleic acid, the adenovirus major late promoter nucleic acid, the mouse metallothionein-I promoter nucleic acid, the Rous sarcoma virus long terminal repeat, the Chinese hamster elongation factor 1 alpha (CHEF-1), human EF-1 alpha, ubiquitin, and human cytomegalovirus major-immediate-early promoter nucleic acid (hCMV MIE).

The term "selection marker" denotes a nucleic acid that allows cells carrying it to be specifically selected for or against, in the presence of a corresponding selection agent. Typically, a selection marker will confer resistance to a drug or compensate for a metabolic or catabolic defect in the cell into which it is introduced. A selection marker can be positive, negative, or bifunctional. A useful positive selection marker is an antibiotic resistance gene allowing for the selection of cells transformed therewith in the presence of the corresponding selection agent, e.g. the antibiotic. A non-transformed cell is not capable to grow or survive under the selective conditions, i.e. in the presence of the selection agent. Negative selection markers allow cells carrying the marker to be selectively eliminated. Selection markers used with eukaryotic cells include, e.g., the structural genes encoding aminoglycoside phosphotransferase (APH), such as e.g. the hygromycin (hyg), neomycin (neo), and G418 selection markers, dihydrofolate reductase (DHFR), thymidine kinase (tk), glutamine synthetase (GS), asparagine synthetase, tryptophan synthetase (selection agent indole), histidinol dehydrogenase (selection agent histidinol D), and nucleic acids conferring resistance to puromycin, bleomycin, phleomycin, chloramphenicol, Zeocin, and mycophenolic acid.

The term "short-term production rate" denotes the amount of polypeptide produced by a single cell within one day as determined from the amount of polypeptide produced within a given time period and the viable cell density, wherein the time period is short. In one embodiment the short-term cultivation is for of from 2 to 20 days, in another embodiment for of from 4 to 15 days, and in still a further embodiment for of from 10 to 14 days.

The term "specific production rate" or "production rate" denotes the amount of polypeptide produced by a single cell within one day as determined from the amount of polypeptide produced within a given time period and the viable cell density. The specific production rate (SPR) can be calculated using the following formula:

$$SPR = P_2 - P_1 / ((D_2 + D_1)/2 * \Delta t) \quad \text{(Formula 2)}$$

with
SPR [pg/cell/d]: specific production rate,
$P_1$ [µg/ml]: polypeptide concentration at the beginning of the time period,
$P_2$ [µg/ml]: polypeptide concentration at the end of the time period,
$D_1$ [cells/ml]: viable cell density at the beginning of the time period,
$D_2$ [cells/ml]: viable cell density at the end of the time period,
$\Delta t$ [d]: duration of the time period.

The term "structural gene" denotes the region of a gene without a signal sequence, i.e. the coding region.

B. THE METHODS AS REPORTED HEREIN

Cell lines/cell clones producing a polypeptide, i.e. cells transfected with a nucleic acid comprising an expression cassette containing a structural gene encoding a heterologous polypeptide, can be grouped in different classes: In a first class of cells the specific production rate is almost constant over multiple generations. In contrast thereto in the second class of cells the specific production rate is decreasing, especially monotonously decreasing, with each generation over multiple generations. Without being bound by this theory the diminishing productivity of polypeptide producing cells and cell lines, respectively, is caused at least in part by the steadily increasing methylation and therewith inactivation/silencing of the promoter nucleic acid operably linked to the structural gene encoding the polypeptide of interest. Further the decrease can be by loss of copies of the structural gene encoding the protein of interest.

The current invention is based, at least in part, on the finding that the CpG dinucleotide at position 425 of the human CMV major-immediate-early (hCMV MIE) promoter/enhancer (SEQ ID NO: 01) is frequently methylated in unstable antibody-producing Chinese hamster ovary (CHO) cell lines. This can be used as marker for the prediction of long-term recombinant production stability of a recombinant cell clone/cell line expressing a protein of interest encoded by a structural gene operably linked to a hCMV-MIE promoter (e.g. of SEQ ID NO: 01).

The current invention is based, at least in part, on the finding that the posttranslational modification of histone adjacent to the promoter can be used as further marker to identify stable expressing/producing cell lines. The presence of an inactivating modification is a marker that the respective cell clone/cell line is very instable and will show a decline in productivity during the future course of the cultivation that is above average (long term instable producing cell clone/cell line). On the other hand the presence of an activating modification is a marker that the respective cell clone/cell line is very stable and will show a decline in productivity during the future course of the cultivation that is below average (long term stable producing cell clone/cell line).

The current invention is based, at least in part, on the finding that by using a combination of the methylation at position 425 of SEQ ID NO: 01 and the relative level of histone 3 acetylation relative to the level of histone 3 (H3ac/H3) close to the promoter nucleic acid a further improvement in the determination of long term stable producing recombinant cell lines/cell clones can be achieved.

B.1. Promoter Methylation

It has been found that the presence of detectable methylation in the promoter nucleic acid of the human CMV MIE promoter at position 425 that is operably linked to the structural gene encoding a polypeptide provides information regarding the long-term productivity of the cell line or cell clone, respectively.

Each promoter nucleic acid used for the expression of a structural gene comprises sites prone to methylation by the cell's enzymes into which it has been introduced if the promoter nucleic acid is not shielded by protective elements. A site amenable to methylation is termed CpG-site and comprises/consists of the dinucleotide CG. But not all CpG-sites are methylated with the same relative frequency—some of the CpG-sites are methylated more often than others. It has been found that certain sites e.g. within the human CMV MIE promoter are methylated with different frequency and have a different impact on promoter silencing.

The following method can be used for identifying a CpG-site in a nucleic acid sequence:
1) providing a cell with a production rate of a polypeptide that is after a cultivation time of 30 generations of the cell in the absence of a selection agent less than 90% of the production rate of the cell after the first generation of the cultivation,
2) separately isolating the DNA from at least 10 cells of a cultivation of the cell of 1),
3) modifying the cytosine of the isolated DNA by bisulfite treatment,
4) identifying a CpG site within the promoter nucleic acid operably linked to the structural gene encoding the polypeptide with a methylation frequency of at least 0.2 based on the DNA obtained in step 3) and thereby identifying a CpG-site.

One criterion i.e. in one embodiment for an instable cell clone/cell line is a production rate of the cell clone/cell line after a cultivation time of 30 to 60 generations of 60% or less than the production rate of the cell clone/cell line after the first generation of the cultivation.

In one embodiment the cell line has a production rate after 30-60 generations in cultivation of more than 60% of the production rate at the beginning of the cultivation.

The step of modifying the cytosine of the isolated DNA by bisulfite treatment can comprise the following steps:
3-a) incubating the isolated DNA in the presence of sulfite ions whereby the DNA is deaminated, and 3-b) incubating the deaminated DNA under alkaline conditions whereby the deaminated DNA is desulfonated.

A method for obtaining a cell clone/cell line producing a polypeptide is a process comprising at least one transfecting step and at least one selecting step including single cell depositing of successfully transfected cells either directly after transfection or after growth in the presence of a selection agent. In the selecting step cells are identified based on their short-term specific production rate, i.e. based on the polypeptide concentration in the supernatant after a short-term cultivation. Among the selected cells some have a specific production rate that is almost constant over multiple generations and others have a specific production rate that is monotonously decreasing over multiple generations. Thus, with generally applied (short term) selection criteria no specific selection of a cell or cells with a stable long-term productivity can be made.

In the methods as reported herein any cell clone/cell line obtained by transfection with an expression plasmid comprising an expression cassette comprising a promoter nucleic acid operably linked to a structural gene encoding a polypeptide of interest to be produced by the transfected cell can be analyzed. The expression plasmid generally comprises also a selection marker. Thus, the cells are cultivated in the presence of a selection agent after the transfecting step and prior to the selecting step. Alternatively the method can comprise cultivating the cells without prior single cell deposition or limited dilution, i.e. as pool, in the presence of a selection agent. Further alternatively the method can comprise cultivating the cells after single cell deposition or limiting dilution.

After the pool cultivation/selection a single cell deposition has to be performed. If the single cell deposition is performed after a pool cultivation step the cells are also further cultivated after the single cell deposition.

In order to identify cells lines or cell clones with a specific production rate that is almost constant over multiple generations the polypeptide concentration in the supernatant and the viable cell density have to be determined at defined cultivation times in a long-term cultivation over multiple generations. Methods suitable therefore are known to a person skilled in the art, such as ELISA and FACS, respectively.

A CpG-site with a high methylation frequency can be identified by bisulfite treatment of single stranded DNA, e.g. at pH 5, with succeeding alkaline desulfurization. Herein methylated and non-methylated CpG-sites can be discriminated. Under the specific treatment conditions cytosine but not 5-methyl-cytosine is deaminated at position 4 of the N-heterocycle and converted to uracil. Complementary DNA strands are converted into two strands, strand A and strand B, which are no longer complementary. The determination can be based on any of these strands.

This long-term cultivation has to be performed only once for the promoter nucleic acid or combination of promoter nucleic acid and cell line. If the same promoter nucleic acid or combination of cell and promoter is used a second time the selection can be based on the already collected data.

A number of techniques can be applied to reveal sequence differences between methylated and non-methylated alleles after bisulfite treatment. For example the sequence of interest (either strand A or strand B) can be amplified by PCR under non-methylation specific conditions, i.e. with primer not sensitive to methylated sites, and subsequently analyzed by methods such as DNA sequencing (with or without cloning), high resolution melting point analysis, or microarray analysis. In another embodiment a quantitative PCR (qPCR) with methylation sensitive or methylation specific primer or probes can be performed. In an alternative approach methylated DNA is precipitated with 5-methyl cytosine specific antibodies followed by a quantitative polymerase chain reaction.

Methylation specific PCR (MSP) can also be used to address the sequence of bisulfite treated DNA directly without previous PCR amplification of the region of interest. Primers used in MSP shall comprise one or more CpG-sites. They are either complementary to unconverted 5-methylcytosine for the detection of methylated DNA or complementary to uracil converted from cytosine for the detection of non-methylated DNA.

The methylation of the CpG-site is determined for a number of cells. In one embodiment the number of cells is at least 10, in another embodiment at least 15, and in a further embodiment at least 20. Afterwards the methylation frequency for the CpG-site is calculated, i.e. the number of cells methylated at that CpG-site divided by the total number of cells analyzed is calculated. A CpG-site with a high methylation frequency is a CpG-site that has a methylation frequency of at least 0.2, in one embodiment of at least 0.25, in one embodiment of at least 0.4, and in one preferred embodiment of at least 0.5.

It has been found that even low levels of methylated promoter nucleic acid, i.e. above a predetermined threshold value, in a cell or cell line used for the production of a polypeptide can be used to predict a decrease in productivity during long-term cultivation.

In FIG. 1 the number of methylated CpG site of the same promoter nucleic acid obtained from different cells is shown.

The human CMV MIE promoter as a nucleic acid sequence as depicted in the following (CpG sites are underlined):

```
                                          (SEQ ID NO: 01)
ATGTTGACATTGATTATTGACTAGTTATTAATAGTAATCAATTACGGGG

TCATTAGTTCATAGCCCATATATGGAGTTCCGCGTTACATAACTTACGG

TAAATGGCCCGCCTGGCTGACCGCCCAACGACCCCCGCCCATTGACGTC

AATAATGACGTATGTTCCCATAGTAACGCCAATAGGGACTTTCCATTGA

CGTCAATGGGTGGAGTATTTACGGTAAACTGCCCACTTGGCAGTACATC

AAGTGTATCATATGCCAAGTACGCCCCCTATTGACGTCAATGACGGTAA

ATGGCCCGCCTGGCATTATGCCCAGTACATGACCTTATGGGACTTTCCT

ACTTGGCAGTACATCTACGTATTAGTCATCGCTATTAGCATGGTGATGC

GGTTTTGGCAGTACATCAATGGGCGTGGATAGCGGTTTGACTCACGGGG

ATTTCCAAGTCTCCACCCCATTGACGTCAATGGGAGTTTGTTTTGGCAC

CAAAATCAACGGGACTTTCCAAAATGTCGTAACAACTCCGCCCCATTGA

CGCAAATGGGCGGTAGGCGTGTACGGTGGGAGGTCTATATAAGCAGAGC

TCCGTTTAGTGAACG.
```

In SEQ ID NO: 01 thirty-three CpG sites are present, which are potential sites for nucleic acid methylation. With the method as outlined above cytosine residues within the human CMV MIE promoter that are predominantly methylated can be identified.

The strand A with all CpG-sites preserved has the nucleotide sequence (SEQ ID NO: 02)
ATGTTGATATTGATTATTGATTAGTTATTAATAGTAATTAATTACGGGGTTATTAGTTTATAGTTTATAT
ATGGAGTTTCGCGTTATATAATTTACGGTAAATGGTTCGTTTGGTTGATCGTTTAACGATTTTCGTTTAT
TGACGTTAATAATGACGTATGTTTTTATAGTAACGTTAATAGGGATTTTTTATTGACGTTAATGGGTGGA
GTATTTACGGTAAATTGTTTATTTGGTAGTATATTAAGTGTATTATATGTTAAGTACGTTTTTTATTGA**C
GTTAATGACGGTAAATGGTTCG**TTTGGTATTATGTTTAGTATATGATTTTATGGGATTTTTTATTTGGT
AGTATATTTACGTATTAGTTATCGTTATTAGTATGGTGATGCGGTTTTGGTAGTATATTAATGGGCGTGG
ATAGCGGTTTGATTTACGGGGATTTTTAAGTTTTTATTTTATTGACGTTAATGGGAGTTTGTTTTGGTAT
TAAAATTAACGGGATTTTTTAAAATGTCGTAATAATTTCGTTTTATTGACGTAAATGGGCGGTAGGCGTG
TACGGTGGGAGGTTTATATAAGTAGAGTTTCGTTTAGTGAACG and the completely deaminated strand A has the nucleotide sequence (SEQ ID NO: 03)
ATGTTGATATTGATTATTGATTAGTTATTAATAGTAATTAATTATGGGGTTATTAGTTTATAGTTTATAT
ATGGAGTTTTGTGTTATATAATTTATGGTAAATGGTTTGTTTGGTTGATTGTTTAATGATTTTTGTTTAT
TGATGTTAATAATGATGTATGTTTTTATAGTAATGTTAATAGGGATTTTTTATTGATGTTAATGGGTGGA
GTATTTATGGTAAATTGTTTATTTGGTAGTATATTAAGTGTATTATATGTTAAGTATGTTTTTTATTGA**T
GTTAATGATGGTAAATGGTTTG**TTTGGTATTATGTTTAGTATATGATTTTATGGGATTTTTTATTTGGT
AGTATATTTATGTATTAGTTATTGTTATTAGTATGGTGATGTGGTTTTGGTAGTATATTAATGGGTGTGG
ATAGTGGTTTGATTTATGGGGATTTTTAAGTTTTTATTTTATTGATGTTAATGGGAGTTTGTTTTGGTAT
TAAAATTAATGGGATTTTTTAAAATGTTGTAATAATTTTGTTTTATTGATGTAAATGGGTGGTAGGTGTG
TATGGTGGGAGGTTTATATAAGTAGAGTTTTGTTTAGTGAATG

The strand B with all CpG-sites preserved has the nucleotide sequence.

(SEQ ID NO: 04)
CGTTTATTAAACGGAGTTTTGTTTATATAGATTTTTTATCGTATACGTTTATCGTTTATTTGCGTTAATG
GGGCGGAGTTGTTACGATATTTTGGAAAGTTTCGTTGATTTTGGTGTTAAAATAAATTTTTATTGACGTT
AATGGGGTGGAGATTTGGAAATTTTCGTGAGTTAAATCGTTATTTACGTTTATTGATGTATTGTTAAAAT
CGTATTATTATGTTAATAGCGATGATTAATACGTAGATGTATTGTTAAGTAGGAAAGTTTTATAAGGTTA
TGTATTGGGTATAATGTTAGGCGGGTTATTTATCGTTATTGACGTTAATAGGGGCGTATTTGGTATATG
ATATATTTGATGTATTGTTAAGTGGGTAGTTTATCGTAAATATTTTATTTATTGACGTTAATGGAAAGTT
TTTATTGGCGTTATTATGGGAATATACGTTATTATTGACGTTAATGGGCGGGGGTCGTTGGGCGGTTAGT
TAGGCGGGTTATTTATCGTAAGTTATGTAACGCGGAATTTTATATATGGGTTATGAATTAATGATTTCGT
AATTGATTATTATTAATAATTAGTTAATAATTAATGTTAATAT and strand B in completely deaminated form has the nucleotide sequence (SEQ ID NO: 05)
TGTTTATTAAATGGAGTTTTGTTTATATAGATTTTTTATTGTATATGTTTATTGTTTATTTGTGTTAATG
GGGTGGAGTTGTTATGATATTTTGGAAAGTTTTGTTGATTTTGGTGTTAAAATAAATTTTTATTGATGTT
AATGGGGTGGAGATTTGGAAATTTTTGTGAGTTAAATTGTTATTTATGTTTATTGATGTATTGTTAAAAT
TGTATTATTATGTTAATAGTGATGATTAATATGTAGATGTATTGTTAAGTAGGAAAGTTTTATAAGGTTA
TGTATTGGGTATAATGTTAGGTGGGTTATTTATTGTTATTGATGTTAATAGGGGTGTATTTGGTATATG
ATATATTTGATGTATTGTTAAGTGGGTAGTTTATTGTAAATATTTTATTTATTGATGTTAATGGAAAGTT
TTTATTGGTGTTATTATGGGAATATATGTTATTATTGATGTTAATGGGTGGGGGTTGTTGGGTGGTTAGT
TAGGTGGGTTATTTATTGTAAGTTATGTAATGTGGAATTTTATATATGGGTTATGAATTAATGATTTTGT
AATTGATTATTATTAATAATTAGTTAATAATTAATGTTAATAT.

In FIG. 4 the frequency of methylation at individual CpG-sites in different cell lines is shown. The numbers have been determined by analyzing 19 to 22 different clones obtained from different CHO parent cell lines after transfection with a plasmid comprising an expression cassette for expressing a polypeptide of interest. Shown is the methylation pattern of single DNAs (bottom) and the frequency of methylation at single CpG sites (top) for each cell line. Cell line K18.1 for example is highly methylated (FIG. 4A). The frequency of methylation is not equal at the different CpG sites but seems to have centers in 3 clusters, i.e. at the 5'-end, the 3'-end, and around position (or nucleotide, respectively) 400. Fourteen out of 22 sequenced inserts had a cytosine at position 425. The methylation of the promoter nucleic acid in cell line 43-16 A10 is shown in FIG. 4E. The distribution of methylation is similar to the distribution observed with cell line K18.1. As with K18.1 the position 425 was methylated most often: five of 20 inserts sequenced contained a cytosine in this position.

In three other analyzed cell lines cytosine is detected sporadically, i.e. as single events, at different CpG sites (FIGS. 4B, 4C and 4D). To obtain statistically significance for cell lines with a low overall methylation frequency sequencing of hundreds of inserts would be required. Additionally these single events may also represent false positive events due to incomplete cytosine deamination rather than actual promoter methylation.

For reliable determination of CpG position specific methylation a methylation specific PCR method has been developed. For the methylation specific PCR primers as shown in the following Table 1-2 can be used. These primers either alone or in combination are also aspects as reported herein.

TABLE 2

Primers that can be used in methylation specific PCR.

| primer no. (direction) | methylation specific | nucleotide sequence | SEQ ID NO: |
|---|---|---|---|
| 227 (forward) | no | ATGTTGATATTGATTATTGATTAG | 06 |
| 228 (forward) | no | TATGGGATTTTTTTATTTGGTAGT | 07 |
| 229 (reverse) | no | ACTCCTCTCCCAAAACTAAATCTA | 08 |
| 237 (reverse) | no | CCAAAACAAACTCCCATTAAC | 09 |
| 238 (forward) | no | GGGGTTATTAGTTTATAGTTTATA | 10 |
| 239 (forward) | no | TGGTATTATGTTTAGTATATGATTTTAT | 11 |
| 240 (forward) | no | GGATTTTTTATTTGGTAGTATATT | 12 |
| 254 (reverse) | yes | AAATCCCCGTAAATCAAACCG | 13 |
| 263 (forward) | no | GGGATTTTTTTATTTGGTAGTATATT | 14 |
| 264 (forward) | no | TATGGGATTTTTTTATTTGGTAGTA | 15 |
| 265 (reverse) | yes | ATCCCCGTAAATCAAACCG | 16 |
| 266 (reverse) | yes | TCCCCGTAAATCAAACCG | 17 |
| 267 (reverse) | yes | CCCCGTAAATCAAACCG | 18 |
| 268 (reverse) | yes | CCCGTAAATCAAACCGC | 19 |
| 262 (reverse) | yes | AAATCCCCRTAAATCAAACCG | 20 |

In the course of primer evaluation it has been found that methylation specific primer pairs, that are highly selective for deaminated CMV promoter DNA with a cytosine at position 425, differ in their properties (see FIG. 6). In one embodiment the primers for the methylation specific PCR have the nucleotide sequence of SEQ ID NO: 14 and SEQ ID NO: 18.

Thus, in one embodiment of the methods as reported herein is the promoter nucleic acid the human CMV promoter nucleic acid of SEQ ID NO: 01. In one embodiment the CpG-site with high methylation frequency is the CpG-sites at position (bp) 425 of SEQ ID NO: 01.

TABLE 3

Expected results for methylation specific (MSP)
primer pairs and universal primer pair in qPCR.

|  | Template | | | |
| --- | --- | --- | --- | --- |
|  | #11 | #62 | #01 | #04 |
| position 425 | T | C | C | T |
| position 437 | T | C | T | C |
|  | Amplification | | | |
| methylation specific primer pair | − | + | + | − |
| universal primer pair | + | + | + | + |

The universal primer pair should amplify all four templates whereas the MSP primer pair should selectively amplify template #62 (SEQ ID NO: 22) and template #01 (SEQ ID NO: 23). The ΔCp value should be as small as possible between the MSP primer pair and the universal primer pair on template #62 and template #01. By contrast, Cp values obtained with the MSP primer pair on templates #11 (SEQ ID NO: 21) and #04 (SEQ ID NO: 24) should be as high as possible, i.e. ΔCp compared to amplification with the universal primer pair should be maximal.

The methylation specific primer should be able to detect 5-methyl cytosine at position 425 selectively albeit two further methylation positions are present at position 416 and 437.

The determination of the methylation is possible with a frequency of methylation of from 1% to 100%.

Comparable results with respect to the methylation extent were observed with a methylation specific PCR and by cloning and sequencing, whereby the methylation specific PCR is much more sensitive. Cell lines with a decreasing productivity in long-term production have a methylation at position 425 with a methylation frequency above a threshold value. The threshold value is in one embodiment twice the background noise of the determination method. A cell line with long-term stable productivity has a frequency of methylation at the CpG site that is below the threshold value.

For high-resolution melting point analysis the promoter nucleic acid is amplified starting from position 334 up to position 487, i.e. 154 bps. An exemplary melting point analysis is shown in FIG. 10A and its first derivative in FIG. 10B. It can be seen that with a high-resolution melting point analysis a methylated promoter nucleic acid (template #16, SEQ ID NO: 25) can be distinguished from a non-methylated promoter nucleic acid (template #11). The methylated promoter nucleic acid fragment can be detected at a relative frequency of 50% or more. The non-methylated promoter fragment can be detected at a relative frequency of 10% or more.

This data shows that the production stability of recombinant CHO cell lines that contain recombinantly introduced genes whose expression is driven by the human CMV major-immediate-early promoter/enhancer can be predicted by measuring the methylation status of the cytosine at position 425.

Thus, it has been found that the determination of C425 methylation can be used as a predictive marker to determine the stability of polypeptide expression in generated recombinant cell clones. This allows the selection of stable clones with stable productivity during cell line development. It has further been found that C425 methylation of 5% or less is a suitable criterion for the selection of stable cell clones (this takes into account the threshold of the used detection method). It has also been found that the fraction of cell clones that are falsely predicted as stable (false negative cell clones) can be reduced by cultivating them for some time in the absence of MTX before testing.

Thus, herein is reported a method for the enrichment of long term (stable) recombinant polypeptide expressing cells lines from a population of transfected cells by selecting cells having a relative promoter methylation at position 425 of SEQ ID NO: 01 of 5% or less. This relative methylation frequency can be determined using a methylation-specific qPCR method as reported herein with the primers as reported herein.

Having established a sensitive and accurate PCR method to quantify methylation of hCMV-MIE nucleotide at CpG site 425, the methylation in recombinant CHO cell lines K18.1, 43 16 A10 and G45-2 has been assessed. The bisulfite-treated DNA that had been analyzed by sequencing was used as template in methylation-specific real time qPCR, either directly or after PCR amplification of the complete hCMV-MIE region (FIGS. 8A and 8B). The two assay set-ups provided comparable results. More importantly, the results correlated well with the results of bisulfate sequencing. This demonstrates that the CpG site 425 methylation-specific qPCR assay can be used to measure hCMV-MIE methylation at CpG site 425 in recombinant CHO cell lines and can be used without previous PCR amplification of the target DNA.

In principal, other CpG sites within the CMV major-immediate-early promoter/enhancer DNA could be explored to predict production instability. However, methylation at C425 was found to be approximately 5-fold higher than the average methylation at all CpG sites. Moreover some sites were not methylated at all even in highly methylated cell clones, e.g. C280 and C289 (FIGS. 4F, 4J and 13). By chosen the right i.e. frequently modified CpG site for promoter methylation analysis the assay becomes more sensitive. Significant methylation of clones G25-17, G25-10 and 43-16 A10 which is about 10% would likely be missed, if a CpG site was randomly chosen for analysis.

The stability prediction by addressing the methylation status of a relevant CpG sites within a promoter nucleic acid can be used also with other heterogenic promoter nucleic acids.

To evaluate a potential correlation of early promoter methylation and production instability, CpG site 425 methylation at the start of a stability study was plotted against the relative alteration of qP in the presence or in the absence of a selection agent (MTX). The correlation plots are shown in FIGS. 11A (with MTX) and 11B (without MTX). For the evaluation, the plot areas were divided into four compartments with limits at 5% methylation—equaling the two to three-fold background of the methylation measurement, i.e. the limit of detection—and 40% decrease in qP—representing the acceptance limit of production stability (this is also an embodiment of the method as reported herein). The number of clones in the different compartments was determined. Contingency analysis of stability status by methylation status using a Pearson chi square test demonstrated a significant association with a p-value of 0.05 for cultivation with MTX and a trend with a p-value of 0.13 for cultivation without MTX. It turned out that the majority of clones with less than 5% methylation at CpG site 425 were found in the fraction of stable clones (less than 40% decrease in qP with or without MTX, shown in upper left compartments).

Thus, summarizing the above, loss of productivity during long term cultivation and scale-up is a major risk in the development of manufacturing cell lines. Therefore, there exists a need for molecular markers of production instability that can be rapidly and easily determined and examined. It has been found that promoter methylation can be employed to predict a loss of productivity in recombinant CHO cell lines. To assess this, DNA methylation of 33 CpG sites within a 603 bp region of the widely used hCMV-MIE promoter/enhancer was analyzed. The overall methylation level of the region investigated varied between approximately 1% and 18% of all CpG sites. One percent apparent methylation represents the technically achievable background resulting from incomplete deamination of non-methylated cytosines. Moreover, within methylated promoters, the level of methylation greatly varies between individual CpG sites and accumulates in three clusters with a maximum at CpG site 425. Methylation at site CpG 425 is approximately 5-fold higher than the average degree of methylation of all other CpG sites. On the other hand, some CpG sites appear to be completely non-methylated, even in highly methylated cell lines. The overall methylation of hCMV-MIE, as well as the distribution of methylation between individual CpG sites, can vary considerably between cell types and tissues (see e.g. Kong, Q., et al., PLoS One 4 (2009) e6679; Krishnan, M., et al., FASEB J. 20 (2006) 106-108; Mehta, A. K., et al., Gene 428 (2009) 20-24).

It has been found that the dominant methylation of CpG site 425 is suited as marker for methylation of hCMV-MIE. It has been established a CpG site 425 methylation-specific qPCR as a fast and sensitive method with medium throughput. When analyzing a large number of cell lines by CpG site 425 methylation-specific qPCR, it has been found that the majority of unstable producers displayed more than 5% methylation at CpG site 425, even before long-term cultivation, whereas the majority of the stable producers showed less than 5% methylation at this site.

Early methylation of CpG site 425 was exclusively found with clones carrying more than ten copies of the heterologous plasmid. Previous reports have provided some evidence that tandem repeats of multiple transgene copies are more susceptible to methylation and silencing in mammalian cells (Garrick, D., et al., Nat. Genet. 18 (1998) 56-59, McBurney, M. W., et al., Exp. Cell Res. 274 (2002) 1-8).

B.2. Histone Acylation

The relative amounts of histone modifications close to the hCMV-MIE promoter were determined. The H3ac and H3K4me3 marks (activating marks) and H3K9me3 as well as H3K27me3 marks (repression marks) were examined. Those histone modifications were examined at positions 404 to 507 of SEQ ID NO: 01 (human CMV-MIE promoter sequence; tacatca atgggcgtgg atagcggttt gactcacggg gatttccaag tctccacccc attgacgtca atgggagttt gttttggcac caaaatcaac gggactt) which indicates a sequence from −97 to −200 bp upstream of transcription start site and contains the CpG site at position C-425 (i.e. −179 bp upstream of transcription start site) and which can be amplified with primer pair 396/397.

Levels of relative histone 3 acetylation relative to the level of histone 3 close to human CMV major-immediate-early promoter/enhancer fragment was investigated as prediction markers for production stability with and without selection agent.

Two exemplary frozen cell lines from the start point (Primary Seed Bank) of cultivation were thawed and the relative amounts of specified histone modifications close to the hCMV-MIE promoter were determined. Project T and project H were independently executed and each cell line was cultivated for at least 60 generations under the conditions with (+) and without (−) selection agent (250 nM methotrexate).

Data of the hCMV-MIE promoter methylation rate (mC-425), the copy number per cell from (PSB) as well as the percentage alteration over 60 generations of specific productivity (ΔqP) were determined. Recording of data was done as previously described by Osterlehner et al.

TABLE 4

Data of 12 project T cell lines. mC-425 is the mean of percentage methylation of cytosine at position 425 upstream of transcription start site (TSS; −179 relative to TSS) of hCMV-MIE at begin of cultivation phase (PSB); ΔqP is the percentage alteration of specific productivity (qP) over a time period of 60 cell generations; the average copy number of the light chain (LC) of the IgG transgene was measured at begin of cultivation (PSB).
Project T: 12 CHO antibody producing cell lines.
Generated by transfection of CHO-K1-M with plasmid p5057

| Sample No. | mC-425 (%) PSB | ΔqP (60 generations) in % +MTX | ΔqP (60 generations) in % −MTX | LC-Copies/Cell PSB |
|---|---|---|---|---|
| T-1 | 0.44 | −35.40 | −34.20 | 4.4 |
| T-2 | 2.20 | −30.60 | −72.00 | 11.5 |
| T-3 | 3.54 | −81.60 | −96.60 | 9.4 |
| T-4 | 0.92 | −23.40 | −47.40 | 4.6 |
| T-5 | 4.41 | −15.60 | −22.20 | 5.3 |
| T-6 | 0.47 | −14.40 | −20.40 | 2.6 |
| T-7 | 0.22 | −16.20 | −31.80 | 1.6 |
| T-8 | 52.40 | −64.80 | −79.20 | 64.3 |
| T-9 | 52.84 | −27.60 | −49.20 | 67.5 |
| T-10 | 49.61 | 3.60 | 1.20 | 70.5 |
| T-11 | 2.02 | −10.20 | −21.60 | 4.6 |
| T-12 | 61.34 | −32.40 | −22.80 | 11.5 |

TABLE 5

Data of 20 project H cell lines. mC-425 is the mean of percentage methylation of cytosine at position 425 upstream of TSS of hCMV-MIE at begin of cultivation phase (PSB); ΔqP is the percentage alteration of specific productivity (qP) over a time period of 60 cell generations; the average copy number of the light chain (LC) of the IgG transgene was measured at begin of cultivation (PSB).
Project H: 20 CHO antibody producing cell lines.
Generated by transfection of CHO-K1-M with Plasmid p7672

| Sample No. | me of C-425 (%) PSB | ΔqP (60 generations) in % +MSX | ΔqP (60 generations) in % −MSX | LC-Copies/Cell PSB |
|---|---|---|---|---|
| H-1 | 15.7 | −46.80 | −80.20 | 168.8 |
| H-2 | 9.9 | −71.00 | −70.30 | 2.0 |
| H-3 | 16.5 | −73.10 | −89.60 | 3.2 |
| H-4 | 10.5 | −69.30 | −69.50 | 2.9 |
| H-5 | 11.0 | −40.40 | −48.80 | 1.8 |
| H-6 | 7.1 | −79.50 | −71.70 | 37.6 |
| H-7 | 4.8 | −66.20 | −81.50 | 53.0 |
| H-8 | 4.4 | −67.40 | −75.70 | 30.6 |
| H-9 | 23.4 | −87.00 | −77.00 | 95.1 |
| H-10 | 26.2 | −16.40 | −73.30 | 48.8 |
| H-11 | 0.2 | −43.10 | −96.10 | 3.3 |
| H-12 | 0.1 | −42.00 | −33.00 | 1.5 |
| H-13 | 1.3 | 8.00 | −18.50 | 1.1 |
| H-14 | 0.0 | 6.80 | 5.40 | 1.3 |
| H-15 | 0.1 | −16.50 | −40.40 | 3.5 |
| H-16 | 0.4 | 16.20 | −32.80 | 3.0 |
| H-17 | 1.0 | −13.20 | −31.30 | 4.2 |
| H-18 | 46.3 | −67.50 | 319.40 | 8.8 |
| H-19 | 16.7 | −11.20 | 2.70 | 10.1 |
| H-20 | 21.8 | −40.30 | −80.60 | 4.8 |

For investigation of the relative amount of histone modification viable CHO cells, which bear recombinant gene driven by the hCMV-MIE promoter, were harvested. After fixation in 3.7% formaldehyde lysed chromatin was sonicated and cross-linked DNA-histone complexes were purified according to appropriate histone modification. Subsequently the accumulated DNA-histone complexes were degraded with proteinase K and DNA fragments were eluted. The amounts of various DNA fragments were compared with qPCR, using specific primer pairs.

To verify antibody-histone binding consistency with respect to the corresponding modification of reference region, various genes were tested for accumulation of a specific histone modification. At first, the amount of antibody filtered histone modification close to the reference regions was compared to the purified sample of a non-specific no antibody control (mock) in project T and project H in one sample each. DNA fragments of antibody purified samples, mock and untreated input sample were used as templates for qPCR. Primer pairs of potential reference regions were added to each sample and qPCR was performed in triplicates. The obtained Cq values were compared as percentage of the input sample. In both projects, the antibody purified samples obtained higher values than mock in the appropriate region. This confirmed proper binding. Furthermore the activation marks H3ac and H3K4me3 accumulated at the active regions Eif3i and Gusb. In contrast the silenced region Fox2a had higher concentration of H3K9me3 whereas H3K27me3 was strikingly located at the Gata5 region. The different histone modifications matched to the corresponding control regions in both projects.

The estimation of relative amount of histone modification on the target region is strictly dependent on a stable modified reference region.

Normalization of a specific histone modification close to the hCMV-MIE promoter to a reference sequence enables the comparison of different cell lines. For this purpose the reference sequence has to have robust and reproducible levels of the respective histone modification.

In following table the average Cq values and the coefficient of variation (CV) of all cell lines, including the three biological replicates are displayed for project T and project H.

TABLE 6

Reference regions in project T and H. The averages and the appropriate coefficient of variation (CV) of Cq values of all ChIP samples including the biological triplicates were calculated for both projects; the rows display the different reference regions within the genome; the columns contain the specific histone modifications; the chosen control regions for the appropriate epigenetic modifications are marked in bold; therefor the Cq distance to mock and the CV were decisive; in both projects, the activation marks H3ac, H3K4me3 as well as total histone 3 are stable accumulated at the Gusb and the Eif3i regions (CV of 2%); the lower Cq values determines Gusb as reference for activation marks; all potential reference regions had stable total histone 3 values.

| Project T: Cq values of ChIP Samples | | | | | | | | |
|---|---|---|---|---|---|---|---|---|
| | H3 | | H3ac | | H3K4me3 | | H3K9me3 | |
| Target | mean | CV | mean | CV | mean | CV | mean | CV |
| Eif3i 431 | 28.24 | 0.01 | 27.57 | 0.02 | 25.45 | 0.02 | 34.35 | 0.03 |
| Gusb 386 | 27.16 | 0.01 | 26.73 | 0.02 | 26.64 | 0.02 | 33.38 | 0.03 |
| Fox2a 484 | 26.32 | 0.01 | 36.43 | 0.05 | 36.20 | 0.05 | 31.54 | 0.02 |
| Gata5 468 | 25.49 | 0.02 | 33.34 | 0.03 | 34.98 | 0.03 | 32.96 | 0.04 |
| Rho 388 | 27.29 | 0.02 | 35.56 | 0.02 | 36.66 | 0.03 | 35.17 | 0.03 |
| Unc13c 474 | 26.81 | 0.01 | 35.40 | 0.03 | 36.35 | 0.05 | 32.01 | 0.02 |

TABLE 6-continued

Reference regions in project T and H. The averages and the appropriate coefficient of variation (CV) of Cq values of all ChIP samples including the biological triplicates were calculated for both projects; the rows display the different reference regions within the genome; the columns contain the specific histone modifications; the chosen control regions for the appropriate epigenetic modifications are marked in bold; therefor the Cq distance to mock and the CV were decisive; in both projects, the activation marks H3ac, H3K4me3 as well as total histone 3 are stable accumulated at the Gusb and the Eif3i regions (CV of 2%); the lower Cq values determines Gusb as reference for activation marks; all potential reference regions had stable total histone 3 values.

| Project H: Cq values of ChIP Samples | | | | | | | | |
|---|---|---|---|---|---|---|---|---|
| | H3 | | H3ac | | H3K4me3 | | H3K9me3 | |
| Target | mean | CV | mean | CV | mean | CV | mean | CV |
| Eif3i 431 | 26.41 | 0.02 | 27.81 | 0.02 | 27.88 | 0.03 | 35.66 | 0.06 |
| Gusb 386 | 25.98 | 0.02 | 27.65 | 0.03 | 27.85 | 0.03 | 34.96 | 0.06 |
| Fox2a 484 | 25.96 | 0.02 | 34.98 | 0.06 | 35.45 | 0.07 | 34.69 | 0.06 |
| Gata5 468 | 25.75 | 0.02 | 33.61 | 0.05 | 35.30 | 0.07 | 35.16 | 0.07 |
| Rho 388 | 27.08 | 0.02 | 34.79 | 0.04 | 35.91 | 0.06 | 35.82 | 0.06 |
| Unc13c 474 | 26.70 | 0.02 | 35.02 | 0.05 | 35.03 | 0.06 | 34.79 | 0.05 |

| Project T: Cq values of ChIP Samples | | | | | | |
|---|---|---|---|---|---|---|
| | H3K27me3 | | Mock | | Input Sample | |
| Target | mean | CV | mean | CV | mean | CV |
| Eif3i 431 | 35.11 | 0.03 | 35.80 | 0.03 | 22.38 | 0.01 |
| Gusb 386 | 33.90 | 0.03 | 35.76 | 0.04 | 22.32 | 0.02 |
| Fox2a 484 | 33.60 | 0.02 | 34.64 | 0.04 | 21.31 | 0.03 |
| Gata5 468 | 30.70 | 0.03 | 34.61 | 0.04 | 21.72 | 0.01 |
| Rho 388 | 35.15 | 0.02 | 36.26 | 0.02 | 22.91 | 0.02 |
| Unc13c 474 | 34.03 | 0.02 | 34.73 | 0.18 | 22.50 | 0.01 |

| Project H: Cq values of ChIP Samples | | | | | | |
|---|---|---|---|---|---|---|
| | H3K27me3 | | Mock | | Input Sample | |
| Target | mean | CV | mean | CV | mean | CV |
| Eif3i 431 | 34.34 | 0.05 | 35.55 | 0.06 | 22.94 | 0.02 |
| Gusb 386 | 33.69 | 0.04 | 35.01 | 0.06 | 22.63 | 0.03 |
| Fox2a 484 | 30.86 | 0.03 | 35.46 | 0.08 | 22.96 | 0.03 |
| Gata5 468 | 30.09 | 0.03 | 34.88 | 0.06 | 22.62 | 0.03 |
| Rho 388 | 33.05 | 0.03 | 36.10 | 0.06 | 23.90 | 0.03 |
| Unc13c 474 | 31.50 | 0.02 | 35.12 | 0.05 | 23.55 | 0.03 |

Gusb as the reference region for active histone modification H3ac and H3K4me3 and Gata5 as a stable region for H3K27me3 differ to the appropriate mock control and had consistent Cq values. Active control regions Eif3i and Gusb are highly stable. For all control regions a stable accumulation of total histone 3 (H3) was observed.

Biological triplicates of CHO cell lines recombinantly expressing an antibody project were analyzed for histone modification close to the location of the hCMV-MIE promoter. For this chromatin fragments were purified using antibodies against specific histone modifications, digested to obtain protein free genomic DNA and quantified by real-time PCR (see FIG. 26). Normalization was executed for each used reference region. To determine the amplification efficiency of each primer pair the LinReg PCR software, version 2014.5 was used (Ruijter, 2009, LinRegPCR). Amplification efficiencies of all primer-template pairs are quite similar. Therefore the Livak method was used for normalization, which assumes similar amplification efficiencies.

TABLE 7

Primer efficiencies. Amplification efficiencies were determined for all cell lines including biological triplicates; the primer pair (396/397) was used; for this purpose the qPCR raw data were applied to the LinRegPCR software, version 2014.5 and efficiencies were calculated; rows are distinguished by the different primer pairs; the mean column contains the average amplification efficiencies of each primer-template pair and the Stdev column contains the appropriate standard deviation; distances between all amplification efficiencies are less than 2%; thus, the Livak method was used for normalization.
Amplification efficiency with LinReg PCR

| Primer pairs | Project T | | Project H | |
|---|---|---|---|---|
| | mean | Stdev | mean | Stdev |
| CMV 396/397 | 1.909 | 0.033 | 1.919 | 0.032 |
| Gusb 386/387 | 1.923 | 0.036 | 1.935 | 0.037 |
| Eif3i 431/432 | 1.893 | 0.036 | 1.923 | 0.034 |
| Fox2a 484/485 | 1.925 | 0.029 | 1.946 | 0.031 |
| Gata5 468/467 | 1.914 | 0.033 | 1.934 | 0.034 |
| Rho 388/389 | 1.876 | 0.036 | 1.902 | 0.037 |
| Unc13c 474/4745 | 1.904 | 0.032 | 1.927 | 0.034 |

The normalization by Livak comprises two normalization steps:
in the first step, the amount (Cq) of histone 3 modification close to the hCMV-MIE promoter is normalized to the amount (Cq) of histone 3 modification at the reference region→$\Delta$Cq
in the second step, the normalized histone 3 modification is set to the normalized total histone 3 close to the hCMV-MIE promoter→$\Delta\Delta$Cq
This finally displays the relative amount of modification per histone 3 close to hCMV-MIE promoter.

Total histone 3 is stable in all reference regions allowing the normalization of histone modification and total histone 3 with the same reference region. This minimizes variation within the normalization process. For instance, the relative Histone acetylation per Histone 3 was normalized to the control region Gusb, as the Gusb region comprises a stable amount of the modified histone and the total Histone 3. The following formula was used for calculation:

$$\Delta\Delta Cq \rightarrow \text{ratio} = \frac{2^{\Delta Cq_{H3\_acetylation}(Cq_{Gusb}-Cq_{CMV})}}{2^{\Delta Cq_{H3\_total}(Cq_{Gusb}-Cq_{CMV})}}$$

Relative amounts of histone modification per histone 3 ($\Delta\Delta$Cq) and total histone 3 ($\Delta$Cq) close to hCMV-MIE promoter were plotted against the $\Delta$qP values. Total histone 3 close to hCMV-MIE promoter were normalized to Gusb and fitted against the $\Delta$qP values. In addition histone 3 per relative copy number (H3/rCN) and mock per histone 3 (Mock/H3) were examined. H3/rCN subtracts ideally the copy number and is a measurement for the relative histone 3 density (H3D) close to hCMV-MIE promoter. Mock/H3 is the unspecific effect of background noise per histone 3.

Correlations were examined with a standard least squares fit model. To this end the software JMP10 (JMP® 10.0.1 Release: 2, 64-bit edition; SAS Institute Inc.) was used.

TABLE 8

Measurement of effect of epigenetic modifications on long term production stability. P-values of effects on $\Delta$qP with (+) and without (−) selection pressure (250 nM MTX) are displayed in the columns; all effects are measured close to hCMV-MIE promoter and ordered in rows; effects of normalized histone 3 (H3), density of histone 3 per relative copy number (H3/rCN), background noise per histone 3 (Mock/H3) and modifications per histone 3 (H3ac/H3, H3K4me3/H3, H3K27me3/H3 and H3K9me3/H3) were calculated in a standard least square model with software JMP10; in project H, acetylation per histone 3 (H3ac/H3) has a highly significant effect on $\Delta$qP if cells were cultivated under selection pressure (+), also H3/rCN, Mock/H3, H3K4me3, H3K27me3 and H3 events resulted in moderate to high significant effects under $\Delta$qP+ condition.

| | Single effect leverage model: P-values for an epigenetic resulted effect | | | |
|---|---|---|---|---|
| | Project T | | Project H | |
| Epigenetic marks | $\Delta$qP+ | $\Delta$qP− | $\Delta$qP+ | $\Delta$qP− |
| H3 | 0.116 | 0.172 | 0.0013 | 0.036 |
| H3/rCN | 0.7981 | 0.5291 | 0.2273 | 0.8701 |
| Mock/H3 | 0.5319 | 0.4735 | 0.0286 | 0.9214 |
| H3ac/H3 | 0.378 | 0.6866 | <0.0001 | 0.1449 |
| H3K4me3/H3 | 0.637 | 0.8012 | 0.0102 | 0.8896 |
| H3K27me3/H3 | 0.4676 | 0.8338 | 0.005 | 0.5864 |
| H3K9me3/H3 | 0.4771 | 0.6858 | n.d. | | n.d. = not determined

The degree of acetylation per histone 3 (H3ac/H3) at the hCMV-MIE promoter has a highly significant effect on the loss of productivity, obtained over 60 generations at the presence of selection agent MTX.

Further significant effects (listed from weakest to strongest effect) were observed for H3/rCN, Mock/H3, H3K4me3/H3, H3K27me3/H3 and H3. In consideration of the effect levels for Mock/H3 and H3 alone H3 alone has a dominant influence on the combined effect X/H3. Epigenetic events with greater effects than H3 alone have been found to be a good prediction marker: →H3ac/H3.

A Jackknife outlier analysis was performed. Thereby one outlier in triplicate was found by comparing $\Delta$qP of both selection agent conditions. In regard to the analysis, cell line H-18 was excluded from effect measurements. Thereafter the samples of project H were analyzed again with the effect screening model after exclusion of cell line H-18. It has been found that the loss of acetylation per histone 3 (H3ac/H3) at the hCMV-MIE promoter has the most significant effect on the loss of productivity, obtained over 60 generations under both selection conditions.

TABLE 9

Effect measurements of modifications on long term stability in project H after exclusion of outlier cell line H-18. P-values of effects on ΔqP with (+) and without (−) selection pressure (250 nM MTX) are displayed in the columns; all effects are measured close to hCMV-MIE promoter and ordered in rows; effects of normalized histone 3 (H3), density of histone 3 per relative copy number (H3/rCN), background noise per histone 3 (Mock/H3) and modifications per histone 3 (H3ac/H3, H3K4me3/H3, H3K27me3/H3 and H3K9me3/H3) were calculated in a standard least square model with software JMP10; most significant effect on ΔqP could be observed for H3ac/H3 under both selection conditions.
Single effect leverage model of project H:
P-values for an epigenetic resulted effect

| Epigenetic marks | ΔqP+ | ΔqP− |
|---|---|---|
| H3 | 0.0005 | 0.0003 |
| H3/rCN | 0.2600 | 0.3016 |
| Mock/H3 | 0.0475 | 0.0485 |
| H3ac/H3 | <0.0001 | 0.0001 |
| H3K4me3/H3 | 0.0138 | 0.3464 |
| H3K27me3/H3 | 0.0072 | 0.0078 |

In project T the plot of H3ac/H3 against ΔqP shows a simultaneous increase of long term stability and the acetylation per histone 3, particularly under selection pressure.

To account for different levels of histone 3 at the hCMV-MIE promoter histone 3 acetylation was further normalized to histone 3 (H3ac/H3).

Relative histone 3 acetylation levels (H3ac/H3) were compared with alterations in specific productivity (ΔqP) over 60 generations in the presence (+) and in the absence (−) of selection agent MSX. After outlier analysis, the standard least squares regression model was fed with H3ac/H3 values of biological replicates and the ΔqP values of 19 CHO cell lines. Significant correlation of H3ac/H3 and ΔqP was detected.

For H3ac/H3 values a decision tree was calculated with jmp software. Best split node and therefore best filter was calculated with the LogWorth statistic. The best split under (+) MSX condition was calculated to be 0.58 histone 3 acetylation relative to the level of Histone 3 (H3ac/H3) for the samples H. In order to reduce the number of false negative Samples the filter was set to the lower value of A>0.5 H3ac/H3.

TABLE 10

The means of delta (ΔqP) at conditions with or without selection agent MTX or MSX, respectively, were calculated for each positive gate and compared to the unfiltered mean and is presented below:

| samples H-1 to H-17, H-19, H-20 | N | Mean ΔSPR (+) MSX | Mean ΔSPR (−) MSX |
|---|---|---|---|
| unfiltered | 56 | −0.39 | −0.55 |
| A >0.5 H3ac/H3 | 23 (41%) | −0.15 | −0.38 |

| samples T-1 to T-12 | N | Mean ΔSPR (+) MTX | Mean ΔSPR (−) MTX |
|---|---|---|---|
| unfiltered | 36 | −0.29 | −0.41 |
| A >0.5 H3ac/H3 | 7 (19%) | −0.19 | −0.32 |

The filter A>0.5 H3ac/H3 increases the mean delta SPR compared to the unfiltered condition.

B.3. Combination of Promoter Methylation and Histone Acetylation

Relative levels of histone 3 acetylation relative to the level of histone 3 close to human CMV major-immediate-early promoter/enhancer fragment and percentage of C-425 methylation of human CMV major-immediate-early promoter/enhancer fragment were investigated as prediction markers for production stability with and without selection agent.

TABLE 11

The means of delta at conditions with or without selection agent were calculated for each positive gate and compared to the unfiltered mean and is presented below:

| samples H-1 to H-17, H-19, H-20 | N | Mean ΔSPR (+) MSX | Mean ΔSPR (−) MSX |
|---|---|---|---|
| unfiltered | 56 | −0.39 | −0.55 |
| A >0.5 H3ac/H3 | 23 (41%) | −0.15 | −0.38 |
| B <5% mC-425[%] PSB | 27 (48%) | −0.24 | −0.45 |
| Combined filter (B ∩ A) | 20 (36%) | −0.13 | −0.36 |

| samples T-1 to T-12 | N | Mean ΔSPR (+) MTX | Mean ΔSPR (−) MTX |
|---|---|---|---|
| unfiltered | 36 | −0.29 | −0.41 |
| A >0.5 H3ac/H3 | 7 (19%) | −0.19 | −0.32 |
| B <5% mC-425[%] PSB | 24 (67%) | −0.28 | −0.43 |
| Combined filter (B ∩ A) | 7 (19%) | −0.19 | −0.32 |

The combination of filter A>0.5 H3ac/H3 with filter B<5% mC-425[%] PSB increases the mean delta SPR compared to the unfiltered condition.

In more detail a decision tree was calculated using the Jmp 10 software to determine the threshold value of the H3ac/H3 ratio in order to allow exclusion of bad producers. The LogWorth statistic was used to identify the best split node. The LogWorth is calculated as: −log 10 (p-value), where the adjusted p-value is calculated in a complex manner that takes into account the myriad number of different ways splits can occur (Sall, 2002, Monte Carlo Calibration of Distributions of Partition Statistics; SAS white paper). The best split for ΔqP+ condition was 0.47 acetylation per histone 3. To minimize false positive values the threshold value was set to 0.5 H3ac/H3 and transferred to both conditions in projects H and T.

In addition, the threshold of 5% for hCMV-MIE promoter methylation (% mC-425) was determined from the recorded methylation data (see Tables above) to use the (synergistic) combination of both prediction markers. Thus, samples with more than 5% DNA methylation or less than 0.5 acetylation per histone 3 at the hCMV-MIE promoter were excluded.

The average of ΔqP was calculated for positive filtered samples and compared with the average ΔqP of the unfiltered samples. This was done under consideration of whether or not MTX was added to the culture medium.

The use of the prediction marker H3ac/H3 results in an increase of long term stability of included samples.

The average ΔqPs after filtration were almost identical in both projects.

TABLE 12

Exclusion of bad producers. Samples with values above 0.5 H3ac/H3 and below 5% mC-425 were used to calculate the average ΔqP; interestingly filtered ΔqPs were almost identical for both projects.

| Project T | N | Mean ΔqP+ | Mean ΔqP− |
|---|---|---|---|
| unfiltered | 36 | −0.29 | −0.41 |
| A >0.5 H3ac/H3 | 7 (19%) | −0.19 | −0.32 |
| B <5% mC-425 | 24 (67%) | −0.28 | −0.43 |

TABLE 12-continued

Exclusion of bad producers. Samples with values above 0.5 H3ac/H3 and below 5% mC-425 were used to calculate the average ΔqP; interestingly filtered ΔqPs were almost identical for both projects.

| Project H | N | Mean ΔqP+ | Mean ΔqP− |
|---|---|---|---|
| unfiltered | 56 | −0.39 | −0.55 |
| A >0.5 H3ac/H3 | 23 (41%) | −0.15 | −0.38 |
| B <5% mC-425 | 27 (48%) | −0.24 | −0.45 |

The degree of histone 3 acetylation at the hCMV-MIE promoter had a significant effect on stability. Also the amount of total H3 and degree of methylation at position C-425 (% mC-425) had effects on the long term stability. Furthermore the found negative correlation of H3ac/H3 and % mC-425 confirms the reliability of these markers.

The threshold setting leads to the exclusion of all bad producers. Cells above this value are predominately stable.

B.4. Combination of Promoter Methylation and Histone Acetylation and Transgene Copy Number The correlation of histone 3 acetylation with the DNA methylation and the copy number were significant, which provides evidence for the interrelation of the copy number, the DNA methylation and the histone 3 acetylation. It has been found that the DNA methylation degree was contrary to the histone 3 acetylation. It has been further found that copy number versus histone 3 acetylation and DNA methylation provides for the fact that cell lines with a higher copy number are mostly non-acetylated and prone for DNA methylation. It has been found the correlations of copy number and the alteration of long-term productivity in the presence and absence of selection agent. Thus, the copy number interacts with the degree of marks, which in turn influence the long-term production stability.

In addition an unintended accumulation of instable cell lines is promoted in the standard cell line development by the early selection cell lines according to their antibody titers. It is assumed that cell lines with a low copy number need to be predominately active whereas producers with a high copy number can have a plethora of different epigenetic statutes from non-over moderate- to high-activation of each individual transgene as long as the sum of the transcripts are comparable. Considering this, the first selection according to the antibody titer either prefers cell lines with high copy numbers which might have stable integration sites by coincidence or low copy number cell lines which are slightly forced to have them. The copy number from begin of cultivation phase was plotted against the stability and it was found that cell lines with high number of transgenes were prone for instability.

Thus, herein is reported as one aspect a three step cell line selection method/process. In the first step antibody expressing cells with a low light chain copy number are expanded, in the second step a selection according to their histone 3 acetylation degrees is performed. Thereafter a fast reduction of the selection agent is performed. Thereby cell lines are obtained with stable integration sites, a reduced risk for gene silencing and for copy number loss as well as the identification of subpopulations with pre-stressed destabilizing mechanisms.

In one embodiment the copy number of stably integrated light chain expression cassettes is below 50. In another embodiment the copy number of stably integrated light chain expression cassettes is below 25. In a further embodiment the copy number of stably integrated light chain expression cassettes is below 10. In a further embodiment the copy number of stably integrated light chain expression cassettes is below 6.

The following examples, sequence listing and figures are provided to aid the understanding of the present invention, the true scope of which is set forth in the appended claims. It is understood that modifications can be made in the procedures set forth without departing from the spirit of the invention.

Figure 9:
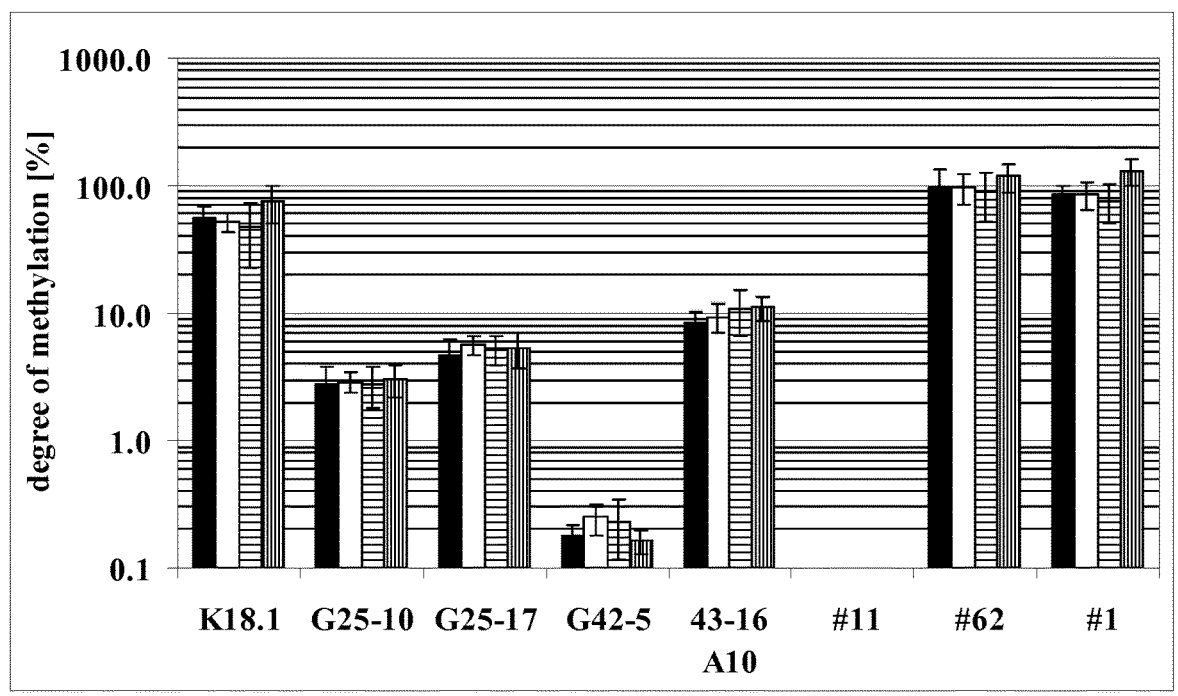

FIG. 9 hCMV-MIE promoter/enhancer nucleic acid methylation at methylation site 425 obtained with primer (black) 239+237 and 239+267, (white) 263+237 and 263+267, (horizontal lines) 264+237 and 264+267 and (vertical lines) 239+237 and 239+266.

Figure 10:
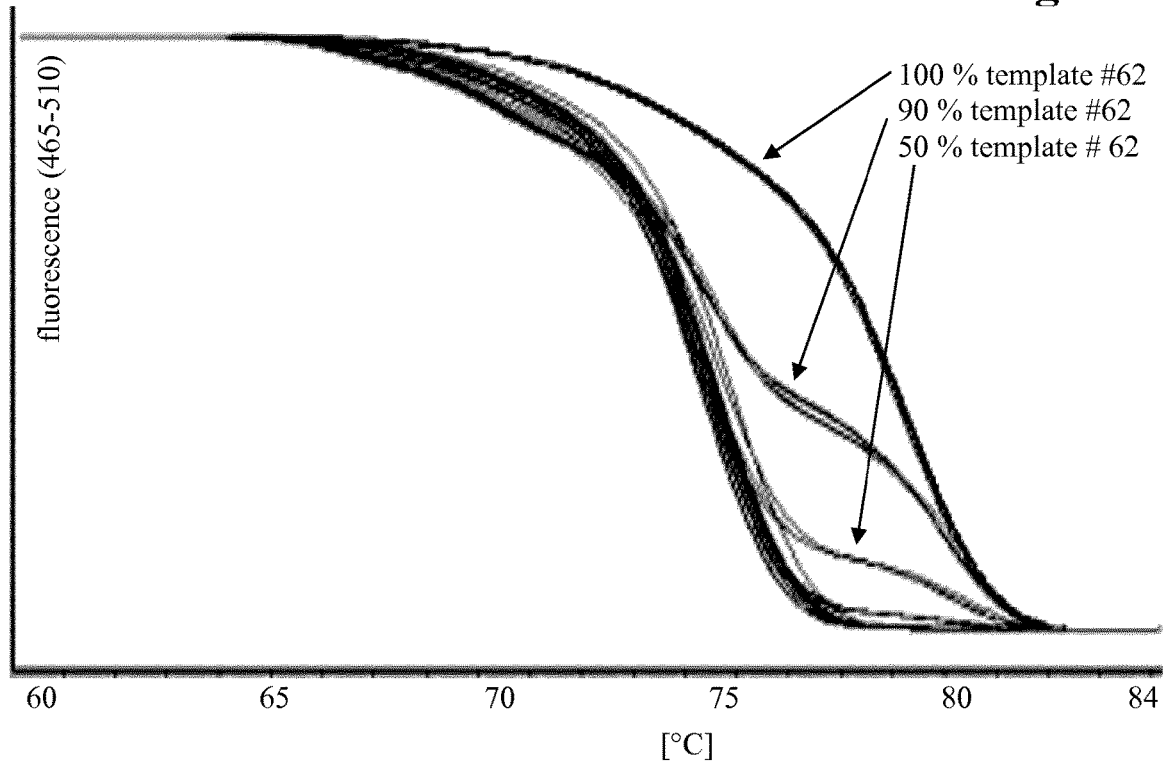
Figure 10:
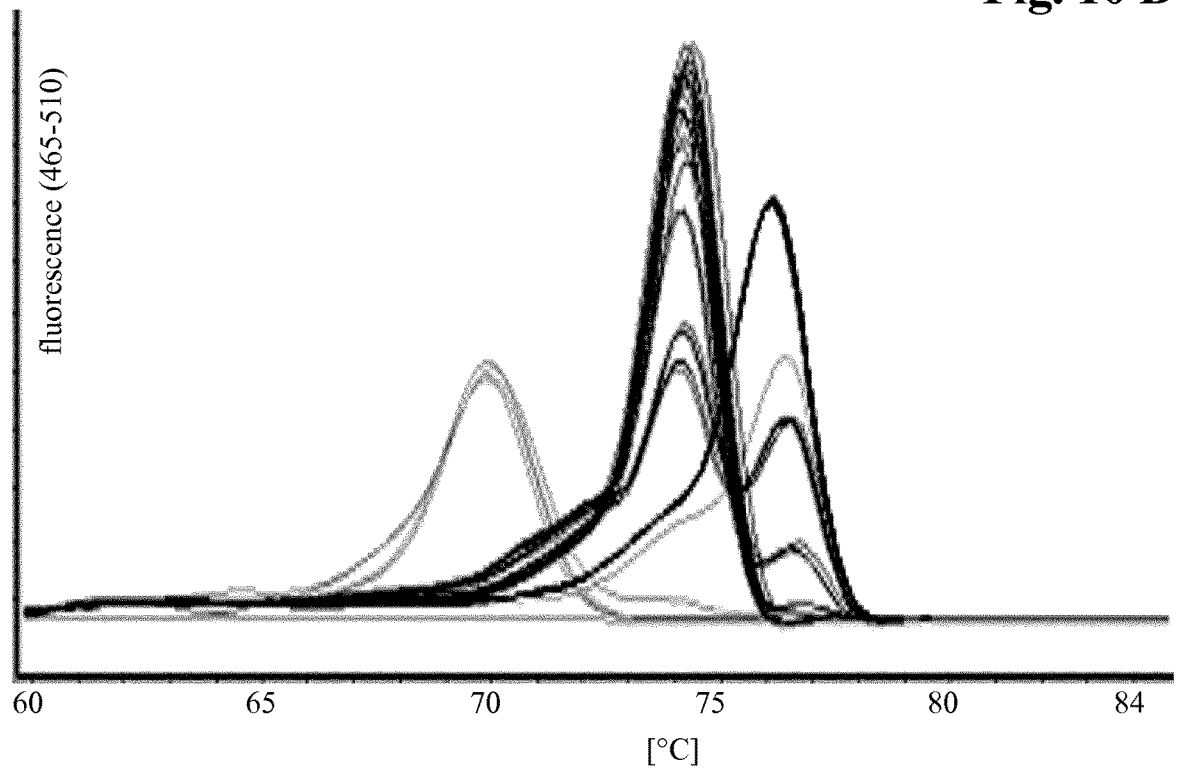

FIG. 10 Exemplary high resolution normalized melting curve analysis (A) and first derivative thereof, i.e. melting peaks (B).

Figure 11:
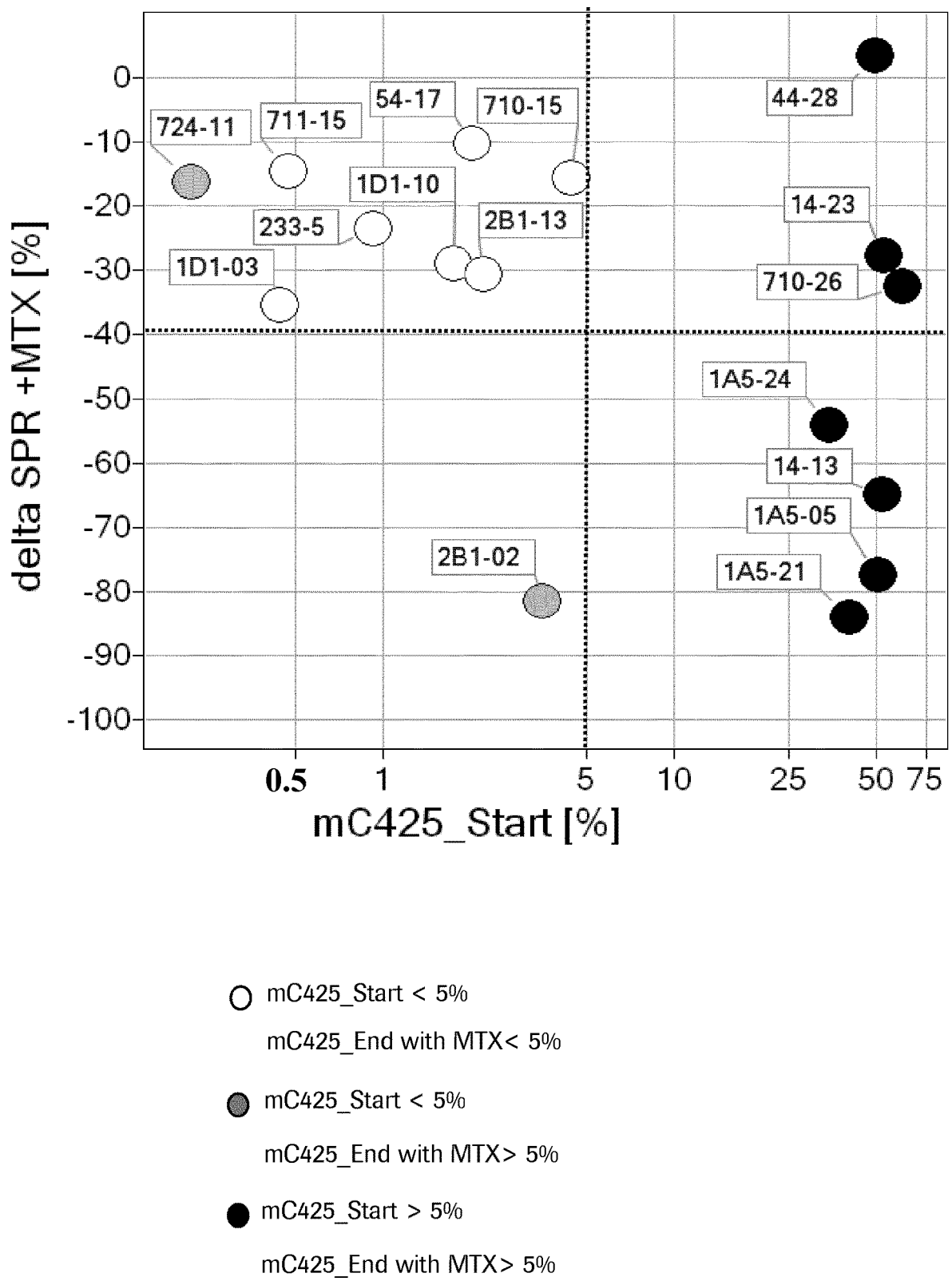
Figure 11:
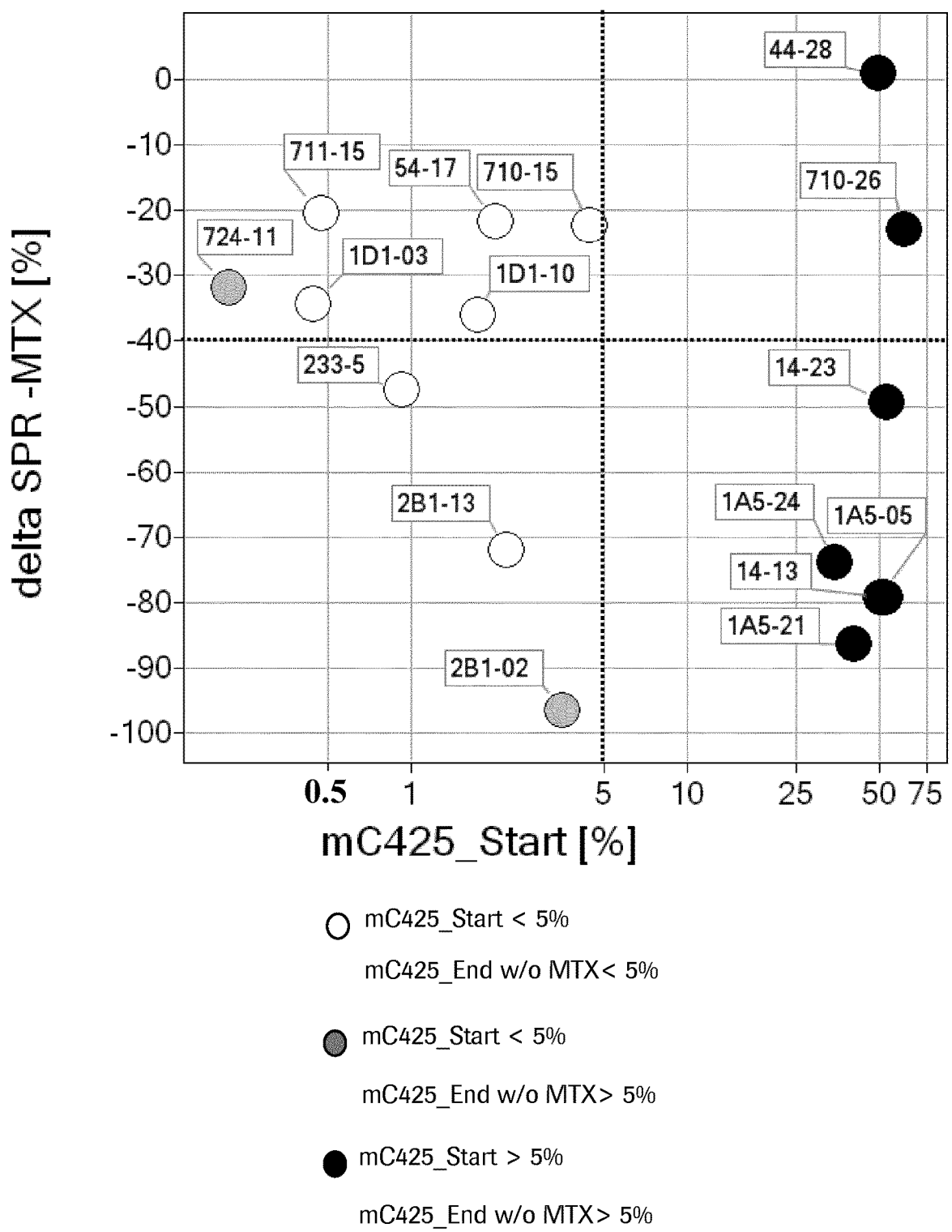

FIG. 11 Correlation of the degree of methylation at C425 before long-term cultivation and the relative alteration of the SPR after 60 generations cultivation with 250 nM MTX (A) or without MTX (B).

Figure 12:
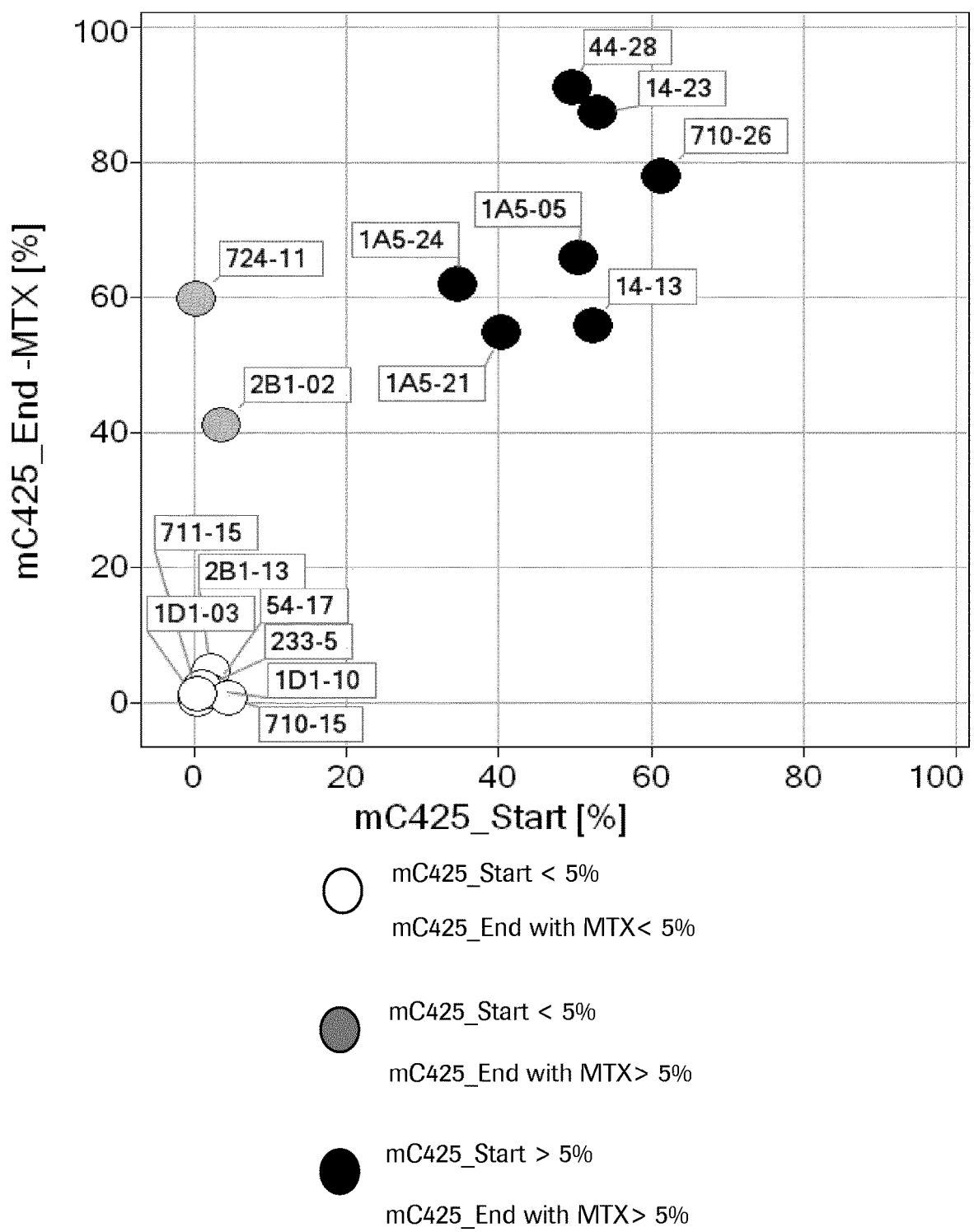

FIG. 12 Correlation of the degree of methylation at C425 before long-term cultivation and the degree of methylation after 60 generations cultivation with 250 nM MTX.

Figure 13:
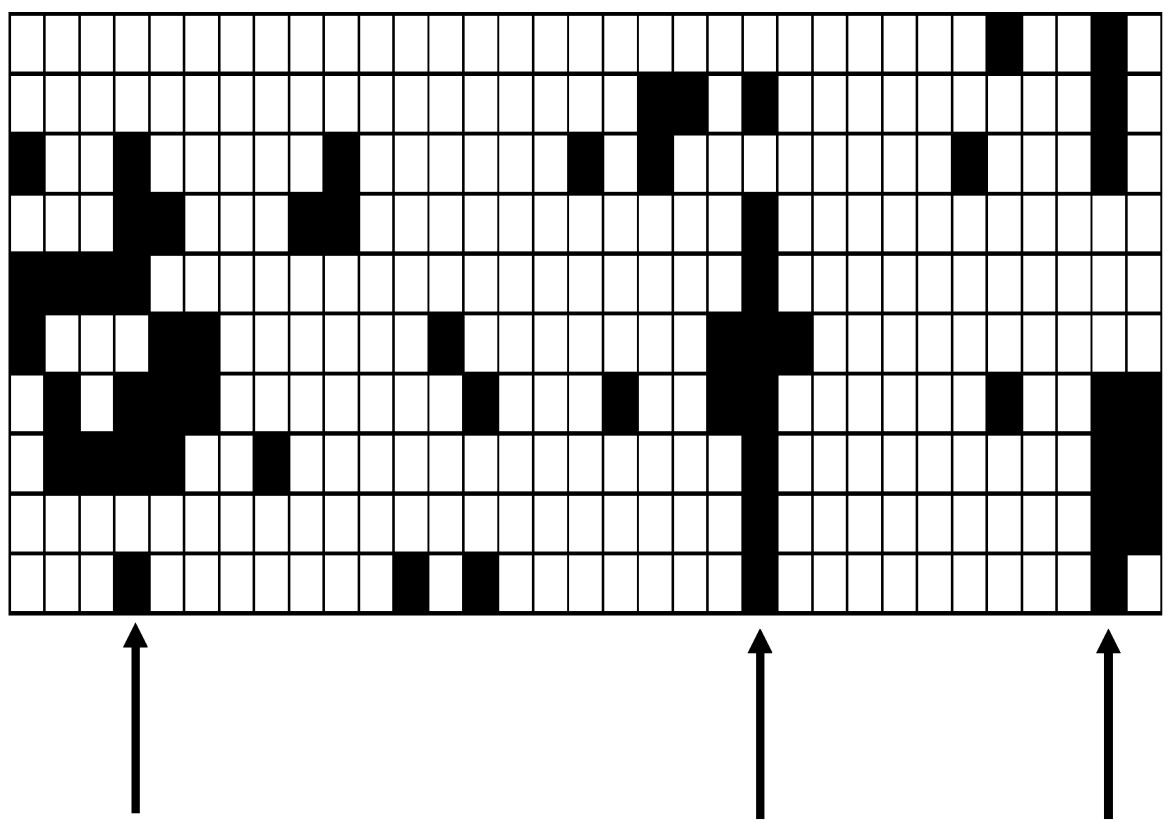

FIG. 13 Schematic representation of methylated CpG sites within hCMV-MIE promoter/enhancer DNA from clone 44-28. Methylated sites are shown in black. Nucleotide position 425 is highlighted by an arrow. Methylation of all CpG sites: 18%; methylation at C425: 80%; methylation at C591: 70%; methylation at C96: 60%.

Figure 14:
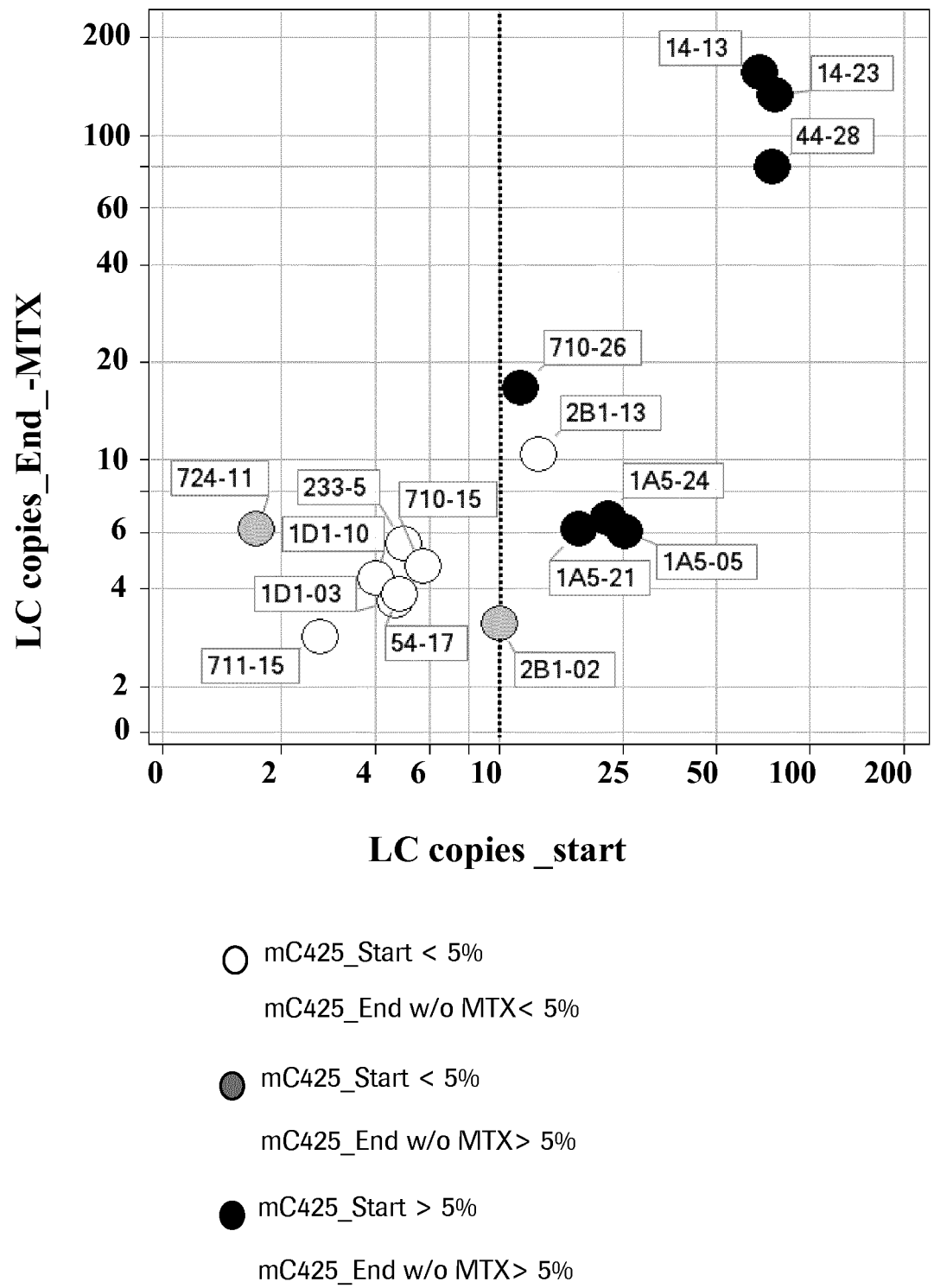

FIG. 14 Light chain gene copy numbers before and after stability testing without MTX.

Figure 15:
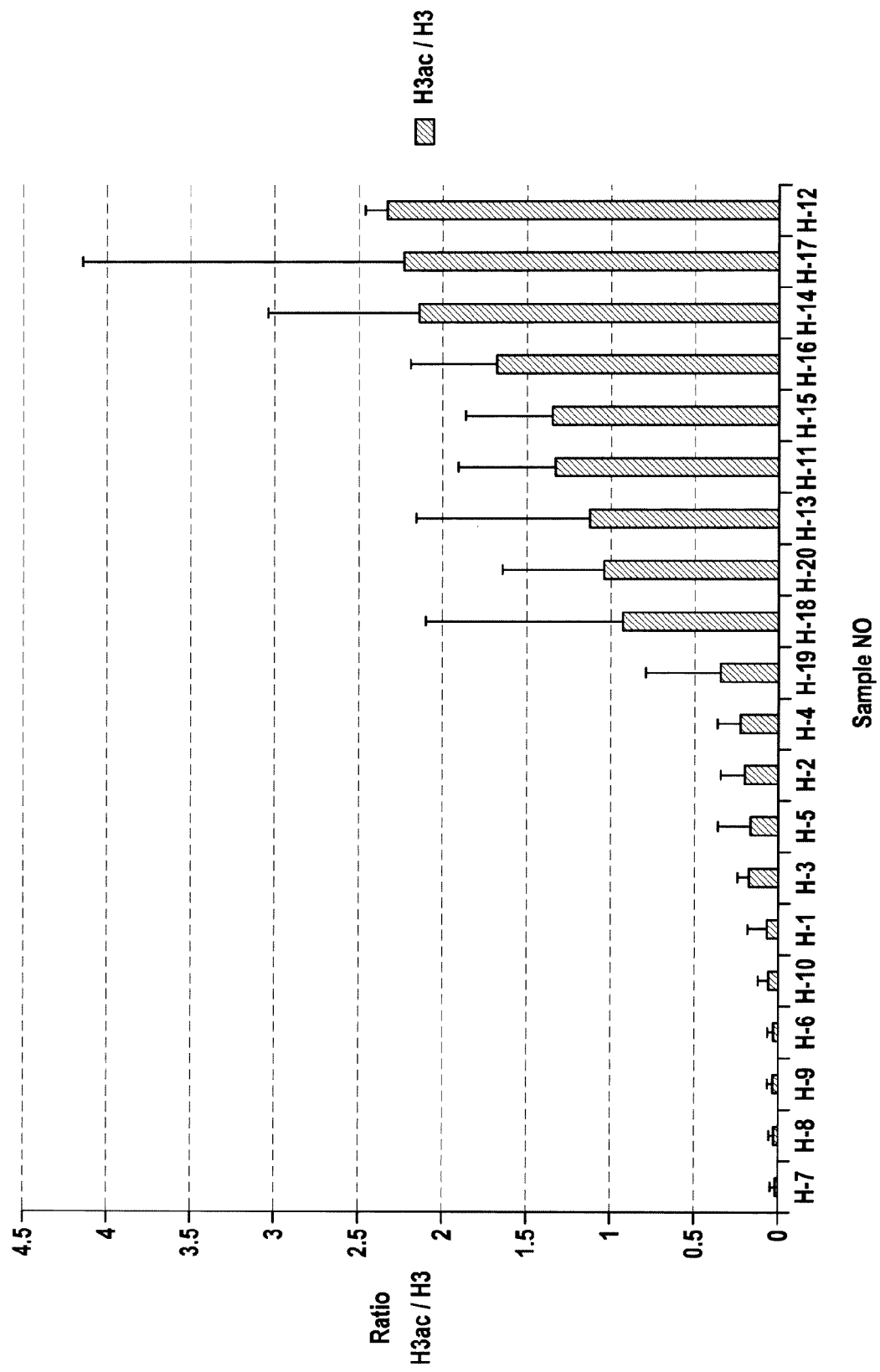

FIG. 15 Relative Levels of histone 3 acetylation relative to the level of histone 3 close to human CMV major-immediate-early promoter/enhancer fragment normalized to reference gene Gusb. The variances between the 3 biological replicates are displayed by the standard deviation.

Figure 16:
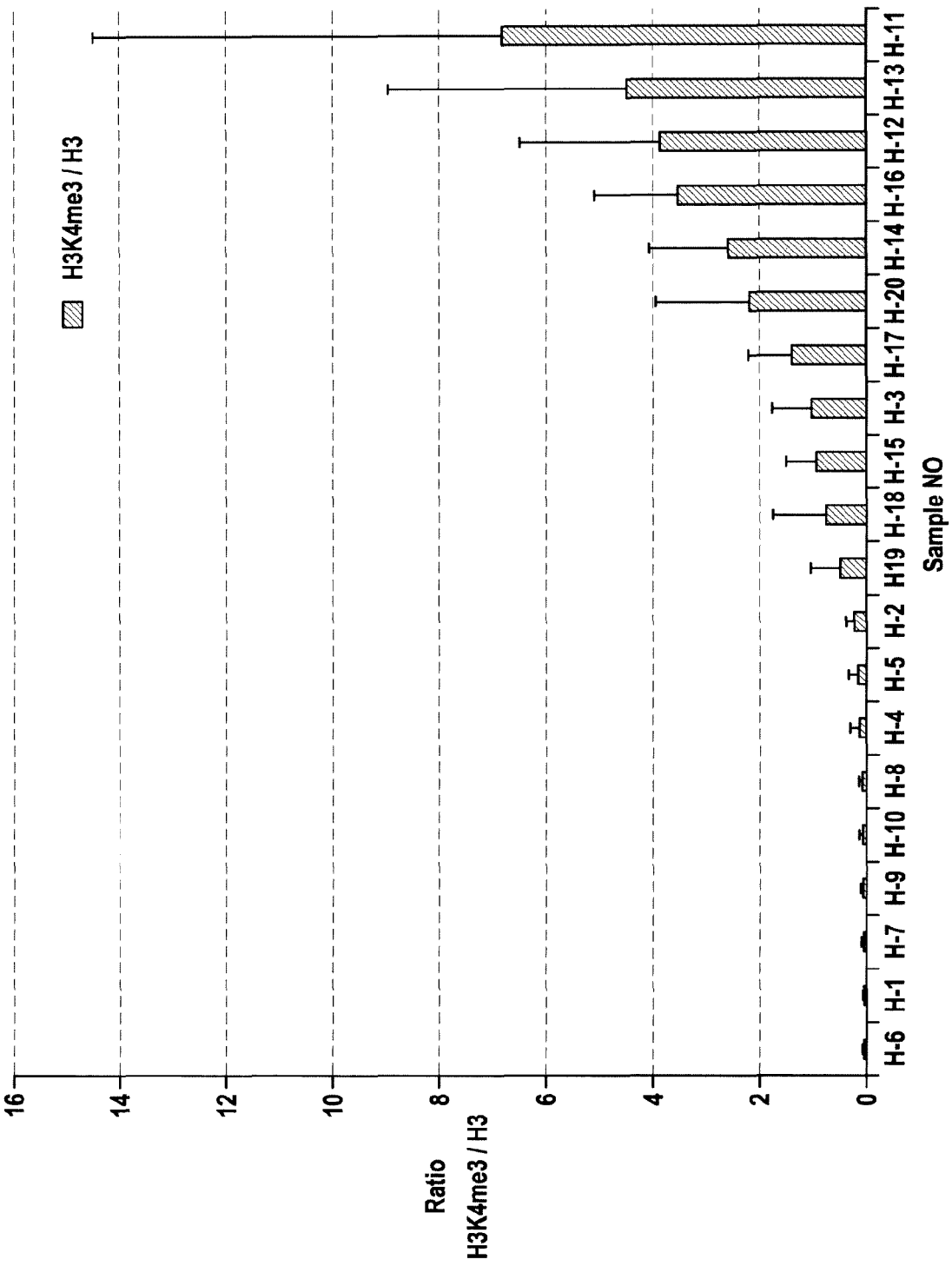

FIG. 16 Relative Levels of histone 3 Lysine 4 three-fold methylation relative to the level of histone 3 close to human CMV major-immediate-early promoter/enhancer fragment normalized to reference gene Gusb. The variances between the 3 biological replicates are displayed by the standard deviation.

FIG. 17 Actual by Predicted Plot of effect H3K4me3/H3 for samples H-1 to H-20 with 3 biological replicates. Confidence curves for the line of fit are shown in dashed lines to provide visual indication of whether the test of interest is significant at the 5% level. The curves need to cross the horizontal line for significance.

FIG. 18 Actual by Predicted Plot of effect H3ac/H3 for the samples H-1 to H-20 with 3 biological replicates. Confidence curves for the line of fit are shown in dashed lines to provide visual indication of whether the test of interest is significant at the 5% level. The curves need to cross the horizontal line for significance.

FIG. 19 Actual by Predicted Plot of effect mC 425[%] for the samples H-1 to H-20. Confidence curves for the line of fit are shown in dashed lines to provide visual indication of whether the test of interest is significant at the 5% level. The curves need to cross the horizontal line for significance.

Figure 20:
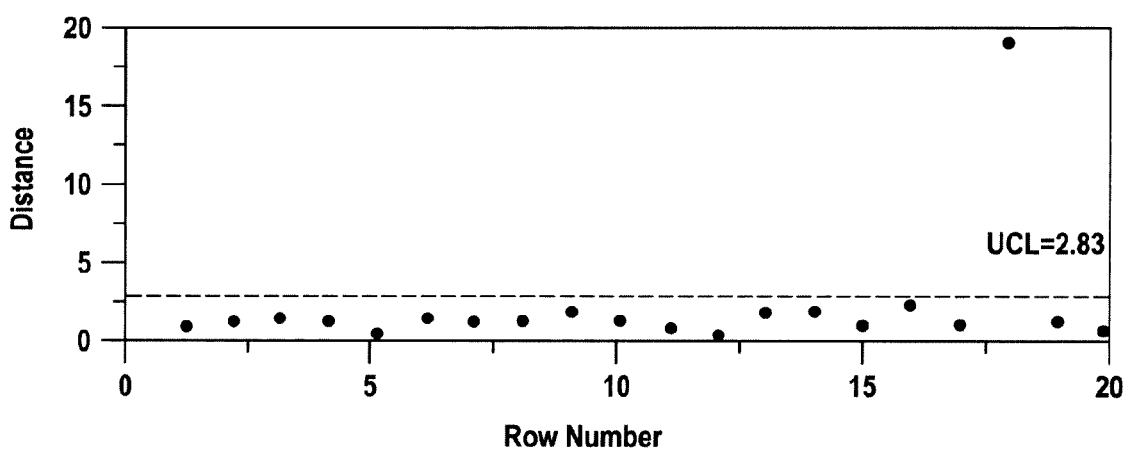

FIG. 20 Outlier analysis of project H with Jackknife Distances for delta SPR with and without MSX as condition. Sample H-18 is far beyond the Upper Control Limit (UCL), which strongly indicates that sample as an outlier.

FIG. 21 Actual by Predicted Plot of effect H3K4me3/H3 for samples H-1 to H-17, H-19 and H-20 with 3 biological replicates. Confidence curves for the line of fit are shown in dashed lines to provide visual indication of whether the test of interest is significant at the 5% level. The curves need to cross the horizontal line for significance.

FIG. 22 Actual by Predicted Plot of effect H3ac/H3 for samples H-1 to H-17, H-19 and H-20 with 3 biological replicates. Confidence curves for the line of fit are shown in dashed lines to provide visual indication of whether the test of interest is significant at the 5% level. The curves need to cross the horizontal line for significance.

FIG. 23 Actual by Predicted Plot of effect mC-425[%] for samples H-1 to H-17, H-19 and H-20. Confidence curves for the line of fit are shown in dashed lines to provide visual indication of whether the test of interest is significant at the 5% level. The curves need to cross the horizontal line for significance.

Figure 24:
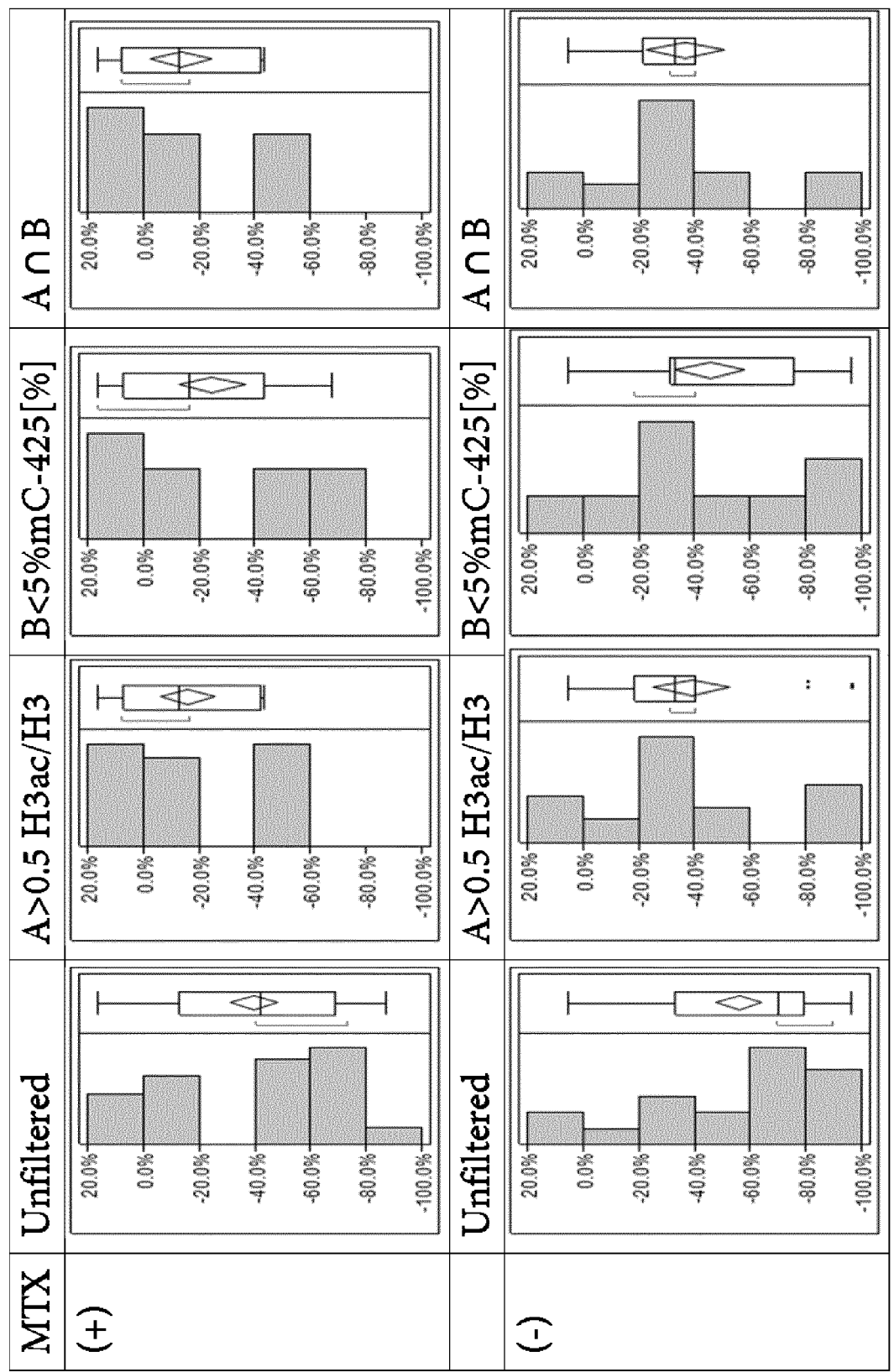

FIG. 24 Delta SPR values of samples H-1 to H-17, H-19 and H-20 plotted in histograms. Different Selection and filter conditions are displayed. The horizontal line within the box represents the median. The confidence diamond contains the mean, the upper and lower 95% of the mean. The middle of the diamond represents the mean. The top and bottom points of the diamond represent the $1^{st}$ and $3^{rd}$ quartiles. The box has lines that extend from each end, called whiskers. The whiskers extend from the ends of the box to the outermost data point that falls within the distances computed as $1^{st}$ quartile −1.5*(interquartile range) and $3^{rd}$ quartile+1.5*(interquartile range). If the data points do not reach the computed ranges, then the whiskers are determined by the upper and lower data point values (not including outliers). The bracket outside of the box identifies the shortest half, which is the densest 50% of the observations (Rousseuw and Leroy 1987).

Figure 25:
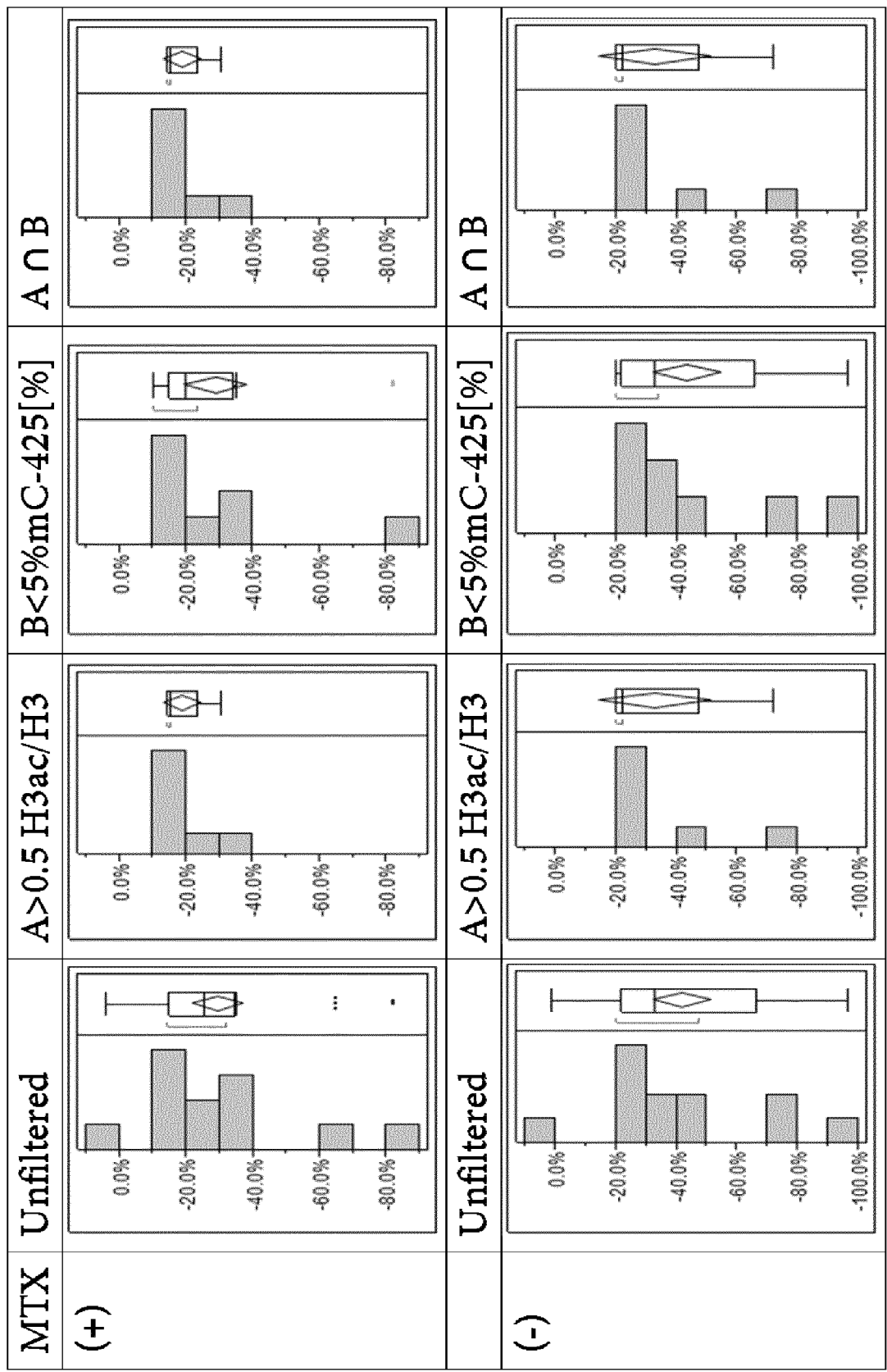

FIG. 25 Delta SPR values of project T plotted in histograms. Different selection and filter conditions are displayed.

Figure 26:
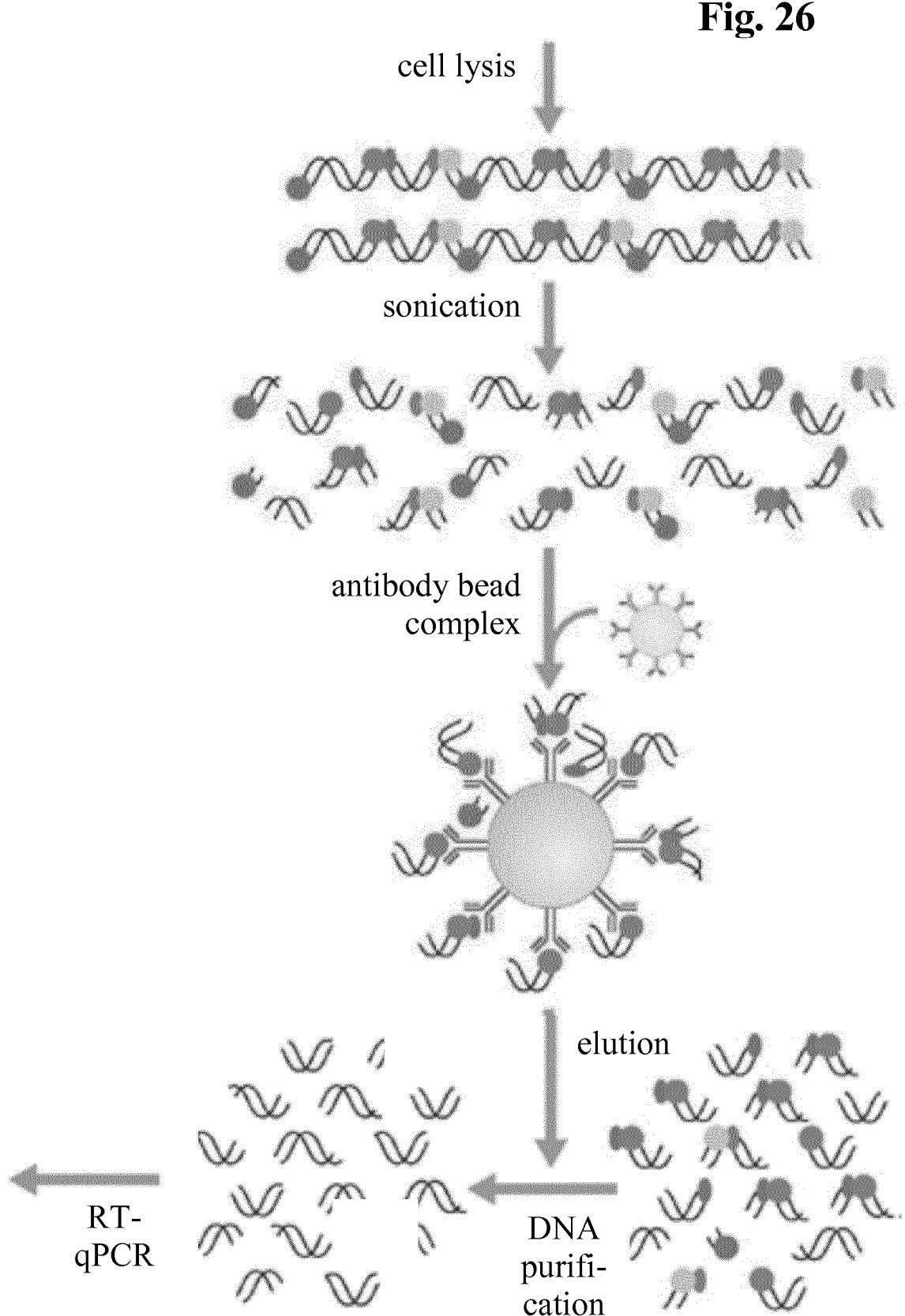

FIG. 26 Scheme for chromatin immunoprecipitation (ChIP) of CHO cell line DNA.

Figure 27:
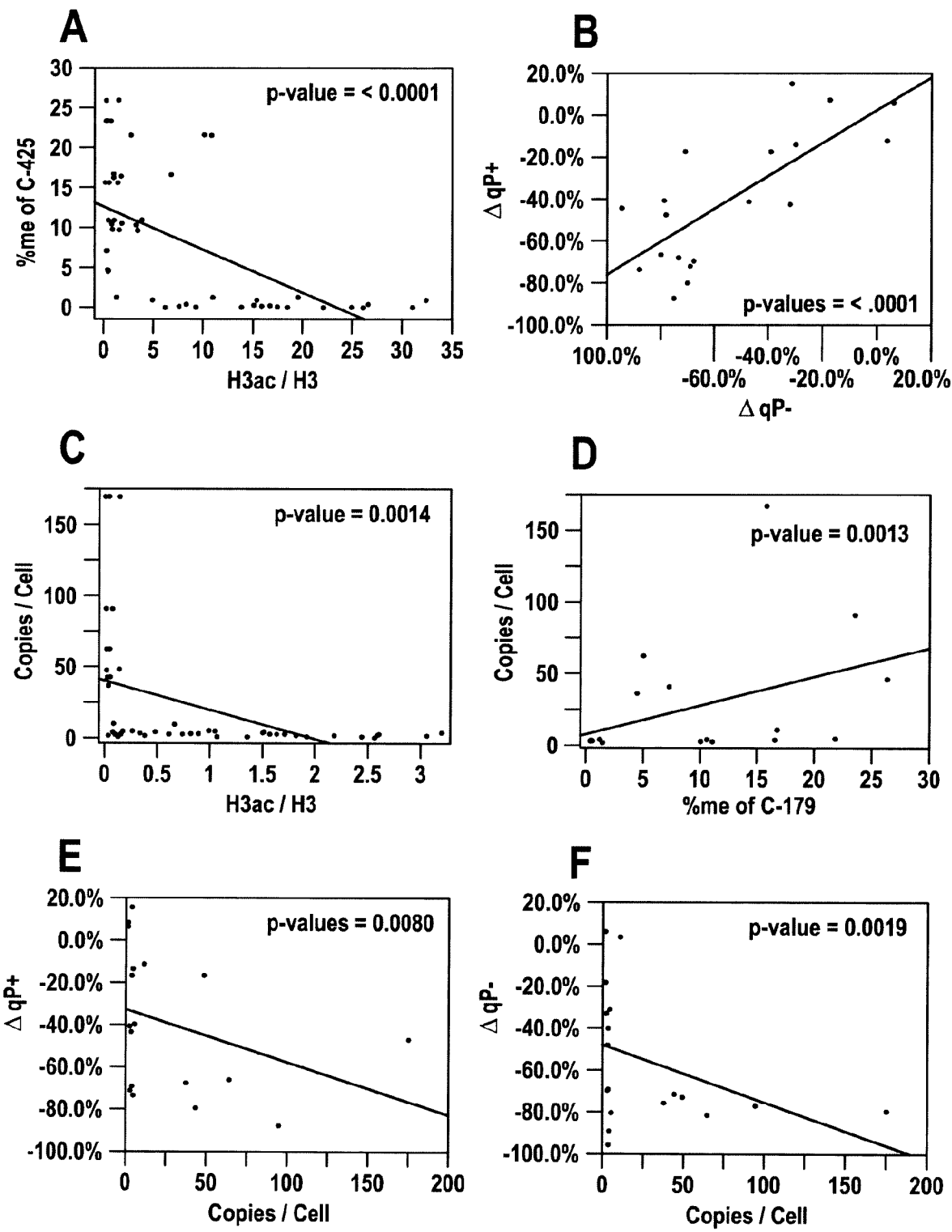

FIG. 27 Correlation studies of epigenetic marks, copy number and stability. A: Plot of C-425 methylation to the acetylation per histone 3 at the hCMV-MIE promoter. B: plot of the alteration of specific productivity over 60 generations of CHO cells at the absence (−) and presence (+) of selection agent MSX after exclusion of cell line H-18. High correlative behavior of stability of cell lines with and without selection agent was determined. C: Plot shows the correlation of copy number and histone 3 acetylation, indicating that only cell lines with low copy number were acetylated at histone 3. D: Plot displays the correlation of copy number and DNA methylation whereas only cell lines with high copy number are predominantly methylated at the hCMV-MIE promoter. E and F: plots show the correlation of copy number and the alteration of productivity over 60 generations in the presence (+) and absence (−) of selection agent. Therefore high copy number cell lines are prone for silencing.

Figure 28:
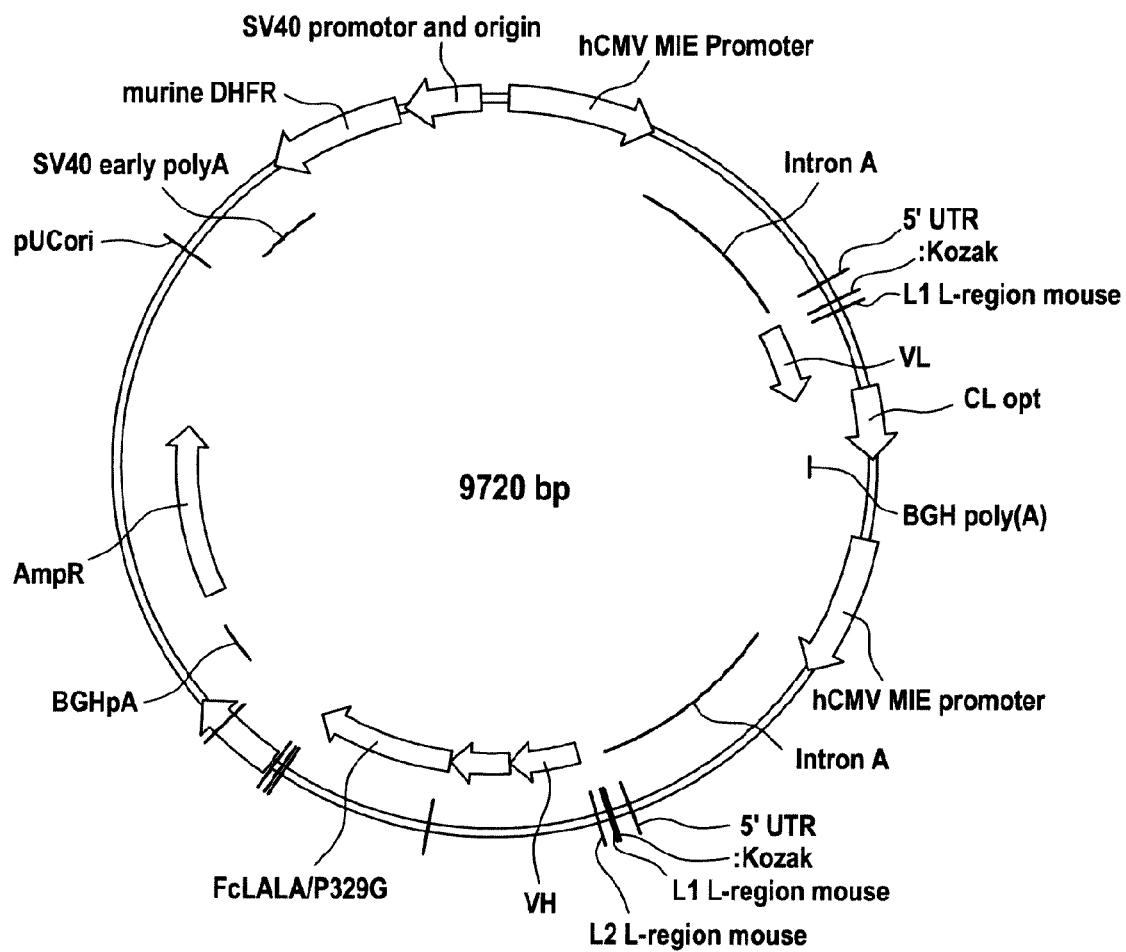

FIG. 28 Human antibody of class IgG expressing plasmid. Light and heavy chain expression cassette of human immunoglobulin were both under the control of a human CMV major immediate-early promoter and enhancer (SEQ ID NO: 01) (hCMV-MIE).

EXAMPLE 1

General Techniques
Solutions

| CHIP Cell lysis buffer |
|---|
| 20 mM Tris-HCl pH 8.0 |
| 85 mM KCl |
| 0.5% NP40 (Nonident P-40/octylphenolpolyethoxyethanol) |
| double distilled H2O |

-continued

Nuclei Lysis buffer 50 mM Tris-HCl pH 8.0
10 mM EDTA pH 8.0
1% SDS
double distilled H2O
1 tablet Roche Complete per 10 ml Low salt wash buffer 0.1% SDS
1% Triton X 100
2 mM EDTA
20 mM Tris-HCl pH 8.0
150 mM NaCl
double distilled H2O High salt wash buffer 0.1% SDS
1% Triton X 100
2 mM EDTA
20 mM Tris-HCl pH 8.0
500 mM NaCl TE buffer 10 mM Tris-HCl pH 8.0
1 mM EDTA (IP) Elution buffer 50 mM NaHCO3
1% SDS
double distilled H2O IP Dilution buffer 0.01% SDS
1.1% Triton X 100
1.2 mM EDTA
16.7 mM Tris-HCl pH 8.1 (8.0)
167 mM NaCl
H2O IP Blocking Buffer
IP Dilution buffer BSA
Salmon Sperm DNA
Roche Complete Protease Inhibitor Recombinant DNA Techniques Standard methods were used to manipulate DNA as described in Sambrook et al., Molecular Cloning: A Laboratory Manual, Second Edition, Cold Spring Harbor Laboratory Press, Cold Spring Harbor, N.Y. (1989). The molecular biological reagents were used according to the manufacturer's instructions.

DNA Sequence Determination

DNA sequencing was performed at SequiServe GmbH (Vaterstetten, Germany).

DNA and Protein Sequence Analysis and Sequence Data Management

The EMBOSS (European Molecular Biology Open Software Suite) software package and Invitrogen's Vector NTI version 9.1 were used for sequence creation, mapping, analysis, annotation and illustration.

Protein Determination

A chromatographic method was used to quantify the amount of antibody present in a sample. A Poros A column was used that binds the Fc-region of the antibody. The antibody binds to the column and is subsequently eluted by low pH conditions. Protein concentration was determined by determining the optical density (OD) at 280 nm, with a reference wavelength of 320 nm, using the molar extinction coefficient calculated on the basis of the amino acid sequence.

Agarose Gel Electrophoresis

Agarose gel electrophoresis was performed to analyze the quality, size and amount of linear DNA fragments (Chong, 2001). According to the size of DNA fragments, agarose solutions of 1% (w/v) were dissolved in 1 ×TAE solution by boiling. Gels contained a final concentration of 0.5 µg/ml ethidium bromide. Samples were prepared by adding 1/6 (v/v) of 6×DNA loading dye. A DNA ladder was used as a size standard. Electrophoresis was performed in 1 ×TAE by applying 10 V/cm gel length (not more than 250 V). After separation, DNA was examined under UV light (254-366 nm) in a gel documentation system (Intas Science Imaging Instruments GmbH, Goettingen, Germany).

Gel Extraction

After Agarose Gel Electrophoresis, the gel slice with the favored band was excised by scalpel and the gel slice was further extracted by QIAquick® Gel Extraction Kit (Qiagen, Hilden, Germany). Following this, 3 volumes of Buffer QG were added to 1 volume of gel (100 mg~100 µl) and incubated for 10 minutes at 50° C. One gel volume of isopropanol was added to the dissolved gel and mixed. DNA fragments adhered to QIAquick spin column by one minute centrifugation at 13,000 rpm and were washed by 0.75 ml Buffer PE and subsequent centrifugation (13,000 rpm, 1 min.). Second wash in another collection tube removed the residual wash buffer. Finally DNA was eluted in 30 µl RNAse-free $H_2O$ into a sample tube by centrifugation (13,000 rpm, 1 min.). DNA can be checked on Flash-gel (FlashGel™ systems, Lonza, Cologne, Germany).

DNA Quantification

Nanodrop 2000 (PEQLAB Biotechnologie GmbH, Erlangen, Germany) was used to quantify DNA concentration by measuring the optical density (OD) at a wavelength of 260 nm. The purity of the DNA can be judged by the ratio OD 260/280 and 260/230. Pure DNA preparations should possess a ratio ≥1.8 and 2.0.

Transformation of Competent Bacteria

Forty-five microliter of chemically competent E. coli NEB 5 alpha (NEB, Germany) were thawed on ice for 10 minutes and thereafter incubated with 1 pg-100 ng of plasmid DNA (1-5 µl) for 30 minutes on ice. The cell suspension was heat shocked at 42° C. for 45 seconds and immediately chilled on ice for 5 minutes. Nine hundred and fifty microliter of room tempered SOC or LB was added and suspension was incubated at 37° C. for 60 minutes with agitation (250 rpm). Transformed bacteria were plated on pre-warmed agar plates containing ampicillin. Plates were incubated overnight at 37° C.

Plasmid Preparation

Plasmids were prepared using the Qiagen Plasmid Mini and Maxi Kits (Qiagen, Hilden, Germany) following the manufacturer's instructions.

DNA purification

Genomic DNA was isolated and purified with the Allprep DNA/RNA Mini Kit (50) (Cat. No. 80204, Qiagen, Hilden, Germany) and the DNAse Blood & Tissue Kit (Qiagen, Hilden, Germany) according to manufacturer's recommendations. Purification of fragments was done with the High Pure PCR Product Purification Kit (Roche Diagnostics GmbH, Mannheim, Germany) by following the manufacturer's instructions.

Phenol-Chloroform Extraction

Plasmid concentration and purification was done by phenol/chloroform extraction. All steps were performed under a chemical hood. Five hundred microliter of linearized plasmid was mixed with one volume Roti® Phenol/chloroform/isoamylalcohol (25:24:1) (Cat. No. A156, Roth, Germany) and vortexed for 30 seconds. Thereafter the emulsion was transferred in pre-centrifuged Phase Lock Gel™ Light tube (Cat. No. 0032005.101, Eppendorf, Hamburg, Germany) for centrifugation (13,000 rpm, 1 minute). Upper aqueous phase was transferred into new tube and the extraction was repeated. Thereafter the upper aqueous phase was mixed with 500 µl chloroform/isoamylalcohol (24:1) and extraction steps were repeated again once. The upper phase was transferred into a new tube and mixed with 0.1 start volume of 3 mol/L sodium acetate buffer (pH 4.8-5.2) and 0.7 start volume of 100% isopropanol (20-30° C.) by inverting the tube 4-6 times. After 20 minutes incubation at −80° C. followed by centrifugation (13,000 rpm, 30 minutes at 4° C.) the supernatant was discarded. The pellet was washed with chilled 1 ml 70% ethanol, centrifuged (13,000 rpm, 5 minutes at 4° C.) and the supernatant was discarded. The wash step was repeated under sterile conditions and residual supernatant was completely removed. The pellet was dried for 5-10 minutes on sterile air and subsequently taken up in 0.5 start volume double distilled water.

Transgene Copy Number Determination

Determinations of transgene copy number as well as methylation rate of C-425 of hCMV-MIE promoter were performed according to the recommendations of Osterlehner et al. (supra).

Relative Copy number (rCN) was calculated by two to the power of the difference of the Cq value of the reference input sample (e.g. Gusb) from the Cq value of the target input sample hCMV-MIE promoter.

$$\text{Relative Copynumber} = 2^{(C_q Input\ sample_{target} - C_q Input\ sample_{reference})}$$

Chromatin Immunoprecipitation

CHO cells lines were harvested with a viability of greater than 90%, preferably greater than 97%. Before fixation, beads for pre-clearing and precipitation were prepared. Pre-clearing beads were generated by incubation (1 hour, RT while rotation) of 15 µl protein A agarose slurry (Roche Diagnostics GmbH, Mannheim, Germany) with 2 µl purified rabbit IgG (Cat. No. PP64B, Millipore, Germany) in 120 µl ChIP Dilution Buffer per sample. Two wash steps with each one volume of ChIP dilution buffer were done for purification followed by resuspension of beads in 85 µl ChIP dilution buffer. Fifteen microliter agarose A beads for pre-cipitation were blocked in 1 ml ChIP dilution buffer with 5 mg/ml BSA (Roche Diagnostics GmbH, Mannheim, Germany) and 100 µg/ml of preheated salmon sperm DNA (10 minutes at 95° C. and 5 minutes on ice; Cat No. 15632-011, Invitrogen, Germany). Resuspended pellet were incubated for 4-5 hours at 4° C. while rotation, subsequently washed three times and mounted in 2 volumes of ChIP Dilution Buffer.

About $1*10^7$ cells per sample were fixed by adding formaldehyde into media up to a final concentration of 3.7% and incubated for 10 minutes at RT as described previously (Beneke, S., et al. PLoS One 7 (2012) e32914). Fixation was stopped by adding glycine up to a one fold solution. After two wash steps with ice cold PBS, and centrifugation at 2000×g for 3 minutes, the pellet was resuspended in 1 ml PBS containing protease inhibitor Roche complete (Roche Diagnostics GmbH, Mannheim, Germany). The suspension was pelleted by centrifugation (3000×g, 5 minutes, 4° C.). The supernatant was discarded.

Lysis of the pellet was done by adding 1 ml cell lysis buffer plus Roche complete (Roche Diagnostics GmbH, Mannheim, Germany) and incubation on ice for 10 minutes. After centrifugation (2300×g, 4 minutes, 4° C.) the nuclei pellet was resuspended in 300 µl Nuclei Lysis Solution and sonicated (Output 5, Duty cycle 90%, 15 seconds sonication followed by 2-3 minutes incubation on ice for 6 cycles; Branson Sonifier B15, Dietzenbach, Germany). Seven hundred microliter of nuclei lysis solution were added to sonicated nuclei followed by centrifugation (13,000 rpm, 15 minutes, 4° C.). The supernatant was transferred into a new tube for storage at −80° C. until use. Sonification grade was tested after protein digestion on an agarose gel.

Chromatin was pre-cleared with 80 µl prepared protein A agarose slurry by incubation (2 hours at 4° C. while rotation) and centrifugation (13,000 rpm, 6 minutes, 4° C., Eppendorf, Hamburg, Germany). Supernatant was transferred into new tube and protein concentration was determined (Pierce® BCA Protein Assay Kit, Thermo Scientific, Rockford, USA). Twenty-five to one hundred microgram of chromatin per immunoprecipitation (IP) were mounted in 200 µl nuclei lysis buffer and added to 300 µl ChIP dilution buffer comprising 3 µg of appropriate antibody. Immuno-precipitation was done overnight at 4° C. while under rotation. Undiluted input samples were stored at −20° C. After overnight incubation, 40 µl of blocked protein A agarose beads were added to IP solution and incubated (1 hour at 4° C. while rotating). The precipitate was washed with twice with low-, once with high-salt wash buffer, once with LiCl wash buffer and once with TE wash buffer. Each wash was done in 1 ml buffer for 5 minutes on rotating platform followed by centrifugation (500×g, 30 seconds, 4° C.). After the last wash step beads were centrifuged with 500×g for 1 minute. Bead pellets were combined with 200 µl IP elution buffer, while simultaneously 25-100 µg chromatin input sample were filled up to 200 µl with IP elution buffer and incubated for 30 minutes at 65° C. while shaking. Subsequently tubes were incubated for 30 minutes at 37° C. after adding 0.5 µl RNAse DNAse free (Roche Diagnostics GmbH, Mannheim, Germany) to each tube. For final protein digestion 10 µl 4 M NaCl (final conc. 0.2 M) and 2 µl proteinase K (final conc. 100-200 µg/ml, Roche Diagnostics GmbH, Mannheim, Germany) were added to the reaction samples and incubated for 1.5 hours at 65° C. DNA was purified by Roche PCR purification kit (Roche Diagnostics GmbH, Mannheim, Germany).

Bisulfite Conversion

For conversion of non-methylated cytosines into uracil the EZ-96 DNA methylation-Lightning™ kit (deep-well format) (ZymoResearch, Freiburg, Germany) was used according to manufacturer's instructions. In brief, gDNA was extracted with DNAse blood & tissue kit (Qiagen, Hilden, Germany) and concentration was measured with Nanodrop 2000 (PEQLAB Biotechnologie GmbH, Erlangen, Germany) to set concentration at 350 ng gDNA in 20 µl double distilled water. Twenty microliter gDNA were mixed with 130 µl of lightning conversion reagent in a conversion plate. The plates were incubated at 98° C. for 8 minutes, then at 54° C. for 60 minutes and finally temporarily stored at 4° C. A Zymo-Spin™ 1-96 binding plate containing 600 µl of M-binding buffer per well was mounted on a collection plate. Samples from the conversion plate were added to the Zymo-Spin™ 1-96 binding plate, mixed and centrifuged (3000×g for 5 minutes). Plates were washed with 400 µl of M-wash buffer and centrifuged (3000×g, 5 minutes). 200 µl of L-desulphonation buffer were added to each well, incubated (20-30° C., 20 minutes) and subsequently centrifuged (3000×g for 5 minutes). An additional wash step was completed with 10 minutes centrifugation at 3000×g and converted DNA was eluted in 30 µl M-elution buffer. Converted DNA was stored at −20° C. until use.

Amplification of Converted and Integrated hCMV-MIE Promoter

TABLE 13

Investigation of CpG methylation of hCMV-MIE promoter, primer pairs for distal (F1 & R1) and proximal (F2 & R2) promoter region were designed as follows:

| | | |
|---|---|---|
| UG_730_Bisul_CMV1 F1 | GATATTGATTATTGATTAGTTATTAATAGTA ATTAA | SEQ ID NO: 44 |
| UG_731_Bisul_CMV1 R1 | CAAATAAAAAAATCCCATAAAATCATATACT AA | SEQ ID NO: 45 |
| UG_732_Bisul_CMV2 F2 | TTAGTATATGATTTTATGGGATTTTTTTATT TG | SEQ ID NO: 46 |
| UG_733_Bisul_CMV2 R2 | TTCTAATACTAAACTCCTCTCCCAA | SEQ ID NO: 47 |

TABLE 14

Picomole of each primer (0.5 µl) were added to 12.5 µl ZymoTaq™ DNA polymerase premix (ZymoResarch, Germany), 3 µl gDNA template and filled up to 25 µl with double distilled water. Polymerase chain reaction (PCR) was done with Mastercyler nexus X1 (Epperdorf, Hamburg, Germany), PCR conditions were as follows:

| | | |
|---|---|---|
| 95° C. | 10 min | |
| 94° C. | 30 sec | 2 cycles |
| 49° C. | 2 min | |
| 68° C. | 2 min | |
| 94° C. | 30 sec | 34-43 cycles |
| 54° C. | 2 min | |
| 68° C. | 2 min | |
| 72° C. | 10 min | |
| 4° C. | ∞ | |

Amplicons were purified with Roche PCR purification kit (Roche Diagnostics GmbH, Mannheim, Germany) in 30 to 40 µl Elution buffer. Concentration was defined with Nanodrop 2000 (PEQLAB Biotechnologie GmbH, Erlangen, Germany) and size of amplicons was displayed by agarose gel electrophoresis.

Inverse PCR

The inverse polymerase chain reaction (iPCR) is a method to determine integration sites of a randomly integrated vector. From this the known vector-sequence near the cutting site will be used to generate primers of at least 20 bp length. Those primers are oriented in opposite directions.

The genome was digested with frequently cutting enzymes (4 bp-cutter) which did not cut between the primer binding sites and at the linearization site of the vector. The resulting fragments are ligated at very dilute conditions so as to favor intramolecular ligation. The circularized sequence can now be amplified with the inverse primers.

Genomic DNA was isolated with Qiagen blood & cell culture DNA prep. midi kit (Qiagen, Hilden, Germany) out of $2 \times 10^7$ cells (~90 µg DNA) per condition (genomic DNA can be stored at −20° C. for several months) and dissolved in 90 µl double distilled water.

The isolated genomic DNA was digested with differing restriction endonucleases at the appropriate working temperature for a minimum of 16 hours. For the digestion of gDNA the Enzymes CviQI, MseI and MspI for the iPCR upstream of PvuI integration site and the enzymes MseI, BfaI and MluCl for the iPCR downstream of the PvuI integration site were used. Ten microgram genomic DNA were used per digestion ($3.8 \times 10^6$ copies).

TABLE 15

Digestion:

| Component | Volume/80 µl | Final amount |
|---|---|---|
| gDNA template | x µl | 10 µg |
| NEBuffer 10× | 8 µl | |
| BSA 10× (if required) | 8 µl | |
| double distilled water | Add to 80 µl | |
| Restriction endonuclease | x µl | 50 U* |

The digested DNA was purified with the Roche PCR-purification kit and eluted in x µl (200 µl) Elution buffer. The high dilution grade of DNA favors intramolecular ligation.

TABLE 16

Ligation:
Neb T4 DNA Ligase (M0202S) for iPCR

| | |
|---|---|
| Digested DNA | 20 µl (1 µg) ($3.8 \times 10^5$ copies) |
| Ligation buffer, 10× | 50 µl |
| T4 DNA ligase (400 U*µl⁻¹) | 1 µl |
| WFI (double distilled water) | 429 µl |

In order to generate circular DNA fragments, the digested DNA was ligated overnight at 16° C. using T4 DNA ligase (NEB, Frankfurt/Main, Germany). Ligated DNA was eluted in 50 µl Elution buffer of the high pure PCR purification kit (Roche Diagnostics GmbH, Mannheim, Germany) and added to 10 ng template DNA. As a control group, non-transfected gDNA for CHO cell line was investigated.

TABLE 17

| Primer | Sequence | Location | SEQ ID NO: |
|---|---|---|---|
| UG_574_16110_BtsI_rev | CTGTCATGCCATCGTAAG ATGCT | 5'PvuI Integration Site | 48 |

TABLE 17-continued

| Primer | Sequence | Location | SEQ ID NO: |
|---|---|---|---|
| UG_575_16110 BtsI_for | GCGGCCAACTTACTTCTGACAACG | | 49 |
| UG_576_16110 AceIII_rev | AAGGCGAGTTACATGATCCCCCAT | 3'PvuI Integration Site | 50 |
| UG_577_16110 AceIII_for | CACCACGATGCCTGTAGCAATGG | | 51 |

TABLE 18 iPCR for 5'iPCR conditions are described as follows.

| Initial Denaturation | 94° C. | 7 min | |
|---|---|---|---|
| Denaturation | 94° C. | 45 sec | 28 cycles |
| Annealing | 60° C. | 45 sec | |
| Elongation | 68° C. | 4 min | |
| Final Elongation | 68° C. | 7 min | |
| Short storage | 4° C. | ∞ | |

Five microliter of PCR fragment was mixed with Orange G (5 µl) and double distilled water (10 µl) and loaded on agarose-gel to verify the distribution of fragments. For 5' iPCR of MseI and MluCI cuffed fragments good results were obtained and no unspecific band in control lanes was detected.

5' amplicons of each sample (cut with MseI and MluCI) were combined and purified with high pure PCR purification kit (Roche Diagnostics GmbH, Mannheim, Germany) in 40 µl Elution buffer.

Quantitative Real-Time Polymerase Chain Reaction

For each qPCR the non-specific fluorescent dye LightCycler®480 SYBR Green I Master in the LightCycler® 480 Instrument II System (Roche Diagnostics GmbH, Mannheim, Germany) was used. SYBR Green is excited using blue light ($\lambda_{max}$=488 nm) and it emits green light ($\lambda_{max}$=522 nm). The SYBR Green dye binds to all double-stranded DNA in PCR. As a result the fluorescence intensity and the amount of DNA product increase simultaneously, which can be detected by the LightCycler® System after each cycle. For quantification the fluorescence was plotted against the number of cycles on a logarithmic scale. Slightly above the emitted background the threshold for detection of DNA-based fluorescence was set by the LightCycler® System. The number of cycles at which the fluorescence passes the threshold is termed quantification cycle (Cq) (Bustin, S. A., et al., Clin. Chem. 55 (2009) 611-22). During the exponential amplification phase a doubling of target DNA is expected in every new cycle. However, the efficiency of amplification is often variable among primers and templates. Analysis of the melting temperature of amplified DNA fragments gives first hints of the specificity of used primer pairs and the amount of primer dimers.

An efficiency of primer template combination can be assessed by a titration experiment to create a standard curve or by efficiency calculation program like LinRegPCR. The program uses non-baseline corrected data from the Light-Cycler® System, performs a baseline correction on each sample separately, determines a window-of-linearity and then uses linear regression analysis to fit a straight line through the PCR data set. From the slope of this line the PCR efficiency of each individual sample is calculated.

For relative quantification the amount of target sequence were compared to a reference sequence, by subtracting Cq (target) from Cq (reference). This normalization is termed ΔCq-method (Schefe, J. H., et al., J. Mol. Med. (Berlin) 84 (2006) 901-910). The reference sequence has to have very stable values, considerably higher than the background values (Mock). Therefore for each reference sequence, the average and the coefficient of variation of all samples within one project was calculated and compared to background levels. Cq values of the different conditions were displayed as % of the input sample, visualizing the distance to mock control.

% of Input Sample=$100*2^{\Delta Cq(Input\ Sample-ChIP\ Sample)}$

Regarding the large number of samples, all qPCR were accomplished in 384 well plates. In each well following ingredients were transferred.

TABLE 19

| (µl) 384 well plate | Solution |
|---|---|
| 5 | Sybr Green Master Mix |
| 0.5 | Primer (10 pM) for. |
| 0.5 | Primer (10 pM) rev. |
| 1.5 | H2O |
| 2.5 | DNA (X ng/µl) |
| 10 | Total |

TABLE 20

The qPCR program was designed as follows:

| Appliance | Temperature (° C.) | Time | Grad. (° C./sec) | Cycles |
|---|---|---|---|---|
| Pre-Denaturation | 95 | 10 min | 4.8 | 1 |
| Amplification | 95 | 10 sec | 4.8 | 40 |
| | 60 | 5 sec (single) | 2.5 | |
| | 72 | 15 sec | 4.8 | |
| Melt curve | 95 | 5 sec | 4.8 | 1 |
| | 70 | 1 min | 2.5 | |
| | 95 | (continuously) | | |
| cooling | | | | |

In the case of the relative quantification of histone modifications, the normalization of sample (treated) to input sample (untreated) is directly replaced by the normalization of treated target sequence to treated reference sequence. Further calculation of histone modification per histone makes the normalization to input sample redundant.

The relative amount of specific histone modification close to human CMV major immediate-early promoter/enhancer fragment were estimated with the Livak method, also known as delta delta Cq (ΔΔCq) method (Livak, K. J. and Schmittgen, T. D., Methods 25 (2001) 402-408), as long as primer-template efficiencies are close to 2 and close to each other (<2% difference of Cq mean).

The method can be used for relative quantification of a target regarding to a reference. The relative quantification of histone 3 acetylation and histone 3 levels close to human CMV major immediate-early promoter/enhancer fragment were normalized to the histone 3 acetylation and the histone 3 levels close to reference gene in two steps. First ΔCq was calculated as follows:

$$\Delta Cq = \text{control} - \text{sample}$$

ΔCq is the distance of quantification cycles (Cq) between control (e.g. ChIP sample value of Gusb) and target (e.g. ChIP sample value of hCMV-MIE) of the same sample, amplified with different primer pairs. To identify the level of histone 3 modification per Histone 3, the ΔΔCq method was used.

$$\Delta\Delta Cq \rightarrow \text{ratio} = \frac{2^{\Delta Cq_{target}(control-sample)}}{2^{\Delta Cq_{ref}(control-sample)}}$$

Sequencing Methods

Sanger sequencing was performed by the company SequiServe (SequiServe GmbH, Vaterstetten, Germany).

Next generation sequencing was performed by GATC (GATC-biotech, Konstanz, Germany) and Active Motif (La Hulpe, Belgium) using Illumina Sequencing technology.

Protein Quantification

Protein concentrations were estimated in comparison to a protein standard with the Pierce® BCA protein assay kit (Thermo Scientific, Rockford, USA).

Protein Fractionation in Compartments

Proteins were fractionated in membrane/cytoplasmic and nuclear proteins (Misawa, Y, 2006). Following this CHO cells (1×10$^7$ cells per sample) were sedimented by centrifugation (300×g, 3 minutes at 4° C.) and the pellet was washed twice in ice-cold PBS supplemented with Roche Complete (Roche Diagnostics GmbH, Mannheim, Germany). Washed pellet was lysed with 1 ml 0.5% Triton X-100 lysis buffer and incubated on ice for 15 minutes. Insoluble nuclei were separated by centrifugation (13,000 rpm, 15 minutes at 4° C.). Membrane/cytoplasm containing supernatant was transferred into a new tube and chilled on ice. The nuclear pellet was rinsed with lysis buffer once and resuspended in 300 µl lysis buffer containing 0.5% SDS followed by sonication (5 seconds, Output 2, duty cycle 90%, Branson Sonifier 450, Dietzenbach, Germany). Seven hundred microliter lysis buffer were added and sample was centrifuged at 13,000 rpm, 15 minutes at 4° C. Nuclei containing supernatant were transferred into new tube and protein fractions were stored at −80° C.

SDS Polyacrylamide Gel Electrophoresis (SDS-PAGE)

For denaturing SDS polyacrylamide gel electrophoresis NuPAGE gels (4-12%) were used (NuPAGE® Novex® 10% Bis-Tris Gel 1.0 mm×12 well, Cat. No. NP0302BOX, Invitrogen, Germany) in combination with the NuPAGE® electrophoresis system. According to Quick Reference Card (NuPAGE® Bis-Tris Mini Gels), gel was fixed in chamber and the inner cassette was filled with 1×MOPS running buffer (20× NuPAGE MOPS SDS Running Buffer, Cat. No. NP0001, Invitrogen, Germany). The outer chamber was also filled to two-thirds of its volume. The comb was removed and the lanes were purged with a small pipette. 30 µl of sample was added to 10 µl 4×NuPAGE LDS-sample buffer, (Cat. No. NP0007, Invitrogen, Germany), 2 µl 1 M DTT (final concentration 50 mM) and incubated at 95° C. for 5 minutes. Samples (20 µl/lane) and markers ((10 µl/lane) SeeBlue Marker prestained, Cat. No. LC 5625, Invitrogen; (5 µl/lane) MagicMark XP anti IgG, Cat. No. LC5602, Invitrogen, Germany) were transferred into the lanes and gel was applied at 30 volts for 50 minutes with NuPAGE® electrophoresis system.

SDS-PAGE and Western Blot

SDS-PAGE induced separated proteins were blotted to a methanol-activated nitrocellulose membrane according to NuPAGE protocol for denaturing electrophoresis (NuPAGE® Technical Guide, Manual part no. IM1001, Invitrogen, Germany) in an XCell II Blot-Module (Invitrogen, Germany) with the appropriate reagents. Blotting was conducted in the SDS-PAGE chamber at 30 volt for 50 minutes. Blotted protein membrane was transferred into a new chamber and washed 3 times for 10 minutes in 1×TBS wash buffer (10×TBS: 0.5 M Tris-Base, 1.5 M NaCl, pH 7.5) followed by 5 minutes incubation in Ponceau solution (0.1%) for general protein detection. The Ponceau solution was discarded and residues were washed away with a 1 minute TBS wash steps twice.

Membrane was blocked for 1 hour at 20-30° C. in 1% blocking solution (Blocking solution: 1/10 Casein (Roche Diagnostics GmbH, Mannheim, Germany), 1×TBS). Subsequently membrane was incubated in primary antibody solution (1% blocking solution+antibody) at 4° C. overnight while shaking. The membrane was washed three times in 1×TBST for 10 minutes at 20-30° C. followed by a 1 minute wash step in 1×TBS. The membrane was incubated in secondary antibody solution (1% blocking solution+antibody) for 45 minutes at 20-30° C. or at 4° C. overnight while being agitated. The membrane was washed three times in 1×TBST for 10 minutes at 20-30° C. followed by two times 1 minute wash step in 1×TBS to remove Tween.

TABLE 21

| Antibody Name | Dilution (WB) | Host | Company | Cat. No. |
|---|---|---|---|---|
| H4K16ac-ab | 1:5000 | Rabbit | Millipore | 07-329 |
| Anti GFP | 1:2000 | Mouse | SIGMA | G 6539 |
| Anti Flag | 1:1000-10000 | Mouse | SIGMA | F 3165 |
| Gal4(DBD + O1679) | 1:100-1000 | Rabbit | Santa Cruz Biotech | Sc-577 |
| Alpha-tubulin | 1:10000 | Mouse | SIGMA | T 9026 |
| Goat anti rabbit | 1:2000 | Goat | Millipore | 12-348 |
| Goat anti mouse | 1:2500 | Goat | Millipore | |

Detection of Antibody-binding was done with the LumiLightPLUS western blotting system (Roche, Penzberg, Germany).

Thawing of CHO Cell Lines

Falcon tubes were prepared with 5 ml of an appropriate medium. Cryovials were stored on dry ice until thawing in a water bath (37° C.). Afterwards CHO cells were taken up into prepared falcon tubes and centrifuged for 3 minutes at 500×g to remove residual DMSO. Pellet was resuspended in 5 ml medium and propagated in disposable 125 ml shake flasks (contain 20 ml appropriate medium) under standard humidified conditions (95% rH, 37° C., and 5% to 8% $CO_2$) at a constant agitation rate of 120 rpm/min to 150 rpm/min. Viability (>95%) and cell concentration can be tested with Cedex HiRes Analyzer (Roche Diagnostics GmbH, Mannheim, Germany).

Cultivation of CHO Cell Lines

Non-transfected CHO cells were split every 3-4 days and seeded with a concentration of $2-3 \times 10^5$ cells/ml in cultivation medium. Transfected cells were seeded with various concentrations of methotrexate (MTX) or methionine sulfoximine (MSX) as the selection agent. After recovery of cell viability (3-4 weeks), stably transfected cells were selected in thymidine and protein-free medium containing 20 nM to 1200 nM Methotrexate (MTX) or 140-160 µM methionine sulfoximine (MSX) as the selection agent. The cells were propagated in 125 ml vented shake flasks under standard humidified conditions (95% rH, 37° C., and 5% $CO_2$) at a constant agitation rate of 120 rpm/min to 150 rpm/min. Every 3-4 days the cells were split into fresh mediums with a cell concentration of $2-3 \times 10^5$ cells/ml. Density and viability of the cultures were determined using the CASY TT or Cedex HiRes cell counter (Roche Innovates AG, Bielefeld, Germany).

Transient and Stable Transfection

Transfection was done with the Amaxa® Cell line Nucleofector® Kit V (Lonza, Cologne, Germany) and the transfection platforms Nucleofector™2b Device and 96-well Shuttle™ System (Lonza, Cologne, Germany).

$5 \times 10^6$ CHO cells per transfection were centrifuged (200×g, 5 minutes) and the supernatant was discarded. The pellet was resuspended in 100 µl of supplemented Nucleofector Solution V and 1.2 pmol of sterile plasmid was added by pipetting up and down. Plasmid was linearized for stable transfection, for transient transfection the circular form was maintained. Suspension was mounted into bubble-free cuvette and program U-24 was activated for CHO cell line transfection. After pulse 500 µl of pre-warmed media was mounted into cuvette and whole suspension was transferred in 8 ml pre-warmed media. Cells were transferred into incubator and cells were ready for first examinations two days after.

Cell Count with Cellavista

60 µl of CHO cell suspension was mixed with 60 µl trypan blue (0.1 µm) in 96 round bottom well and incubated at 20-30° C. for 5 minutes. Afterwards treated CHO cell suspension was 1:50 diluted with medium and 200 µl were transferred into 96 flat bottom wells (Greiner, Germany). Slow centrifugation (500×g, 5 minutes) resulted in fast sedimentation of cells.

For a precise cell count pictures from the middle of the well were taken, to avoid display error of pictures approaching the edge of each well. The Cellavista cell imager (SynenTec, Munich, Germany) was used for the purpose of cell count. Each sample was done in replicate and the entire 10 pictures were used to calculate cell count.

Cell Count with Cedex HiRes Analyzer

For cell count of a sample number up to 40, the Cedex HiRes Analyzer (Roche, Germany) was used. Following this, the CHO cells were diluted at a ratio of 1:5 in HiRes medium and 300 µl were transferred to tubes. Cell calculation was done according to manufacturer's recommendations. Samples were analyzed in duplicates to verify the cell number.

Sample Preparation for Antibody Analysis

Cell concentration was calculated and 2 ml per sample were centrifuged (500×g, 5 minutes at 20-30° C.). Supernatant was transferred to new 96 deep well plates and stored at −20° C. until use. Frozen supernatant was thawed overnight at 4° C., 6× inverted and centrifuged (4,000 rpm, 30 minutes at 20-30° C.). 310 µl were filtered with a multi-screen Millipore plate atop a barcoded 96 round well plate by centrifugation (1,200 rpm, 3 minutes at 20-30° C.).

Quantification of Antibody Production with HPLC

A chromatographic method was used to quantify the amount of antibody present in a sample. A Poros A column was used that binds the Fc-region of the antibody. The antibody binds to the column and is subsequently eluted by low pH conditions. Protein concentration was established by determining the optical density (OD) at 280 nm, with a reference wavelength of 320 nm, using the molar extinction coefficient calculated on the basis of the amino acid sequence.

Quantification of Antibody Production with ELISA

The ELISA (Enzyme Linked Immunosorbent Assay) technique is based on the antibody sandwich principle. A capture antibody specific to the analyte of interest for instance the Fc part of IgG is bound to a microtiter plate to create the solid phase. Following the blocking and washing steps, samples, standards (dilution series of reference antibody), and controls are then incubated with the solid phase antibody, which captures the analyte. After washing away unbound analyte, a conjugated detection antibody (e.g. POD conjugated) is added. This detection antibody binds to a different epitope of the molecule being measured, completing the sandwich. The BM Chemiluminescence ELISA Substrate POD (Roche Diagnostics GmbH, Mannheim, Germany) provides a substrate solution of peroxidase-based (POD, HRP) secondary detection system. The rate of signal generation in an immunoassay is directly proportional to the amount of marker enzyme bound to the solid phase. Antibody concentration was calculated by the slope of standard dilution.

Generation of Recombinant CHO Cell Lines Comprising hCMV-MIE Promoter

Recombinant cell lines expressing human antibody constructs of class IgG were generated by transient or stable transfection of CHO-K1 suspension growing cells. Light and heavy chain expression cassettes of human immunoglobulin were both under the control of a human CMV major immediate-early promoter and enhancer.

The vector also comprised a nucleic acid sequence encoding murine dihydrofolate reductase (DHFR). Transfection of cells was performed by Amaxa nucleofection system (Lonza Cologne GmbH, Cologne, Germany).

CHO-K1 M suspension was transfected with circular plasmid DNA for transient expression of antibody, using the Nucleofector device in combination with the Nucleofector Kit V (Lonza Cologne GmbH, Cologne, Germany) according to the manufacturer's protocols. Transient transfected cell suspensions were seeded in 96 well plates and incubated for 5 days.

Stable transfected cell suspensions were seeded in 384 or 6-well plates containing thymidine-free medium with 250 to 1600 nM methotrexate (MTX) as the selection agent. After three to four weeks antibody-expressing cell pools were examined for long term stability over a period of one to three months. Antibodies expressing single cell clones were seeded in 384 and 96 well plates. After three weeks, antibody-expressing cell lines were identified by measuring antibody titers in the culture medium by ELISA. Growing wells were randomly picked and in the interests of long term stability assay cell clones were expanded in higher volumes (3 ml per well in 6 well plates) and antibody concentration was determined by protein A HPLC and ELISA at the end of each passage.

The cells were propagated in disposable 125 ml vented shake flasks or 6 well plates under standard humidified conditions (95% rH, 37° C., and 5% to 8% $CO_2$) at a constant agitation rate of 120 rpm/min to 150 rpm/min.

Every 3-4 days the cells were split into fresh mediums. Density and viability of the cultures were determined using the Cedex HiRes cell counter (Roche Innovates AG, Bielefeld, Germany) or Cellavista CV3.1 (SynenTec Bio Services GmbH, Munich, Germany).

Long-Term Cultivation and Production of CHO Cell Lines Comprising hCMV-MIE Promoter The cells were tested for phenotypic (i.e. production) stability for 2 to 3 months after transfection in the presence of selection agent MTX. The cells were continuously cultivated in vented 125 ml shake flasks containing 20-40 ml medium or 6 well plates containing 2-4 ml medium with selection agent and diluted twice a week with fresh medium. Seeding density was 2 to $3*10^5$ cells/ml. Prior to passage, viable cell density and viability were determined.

Antibody concentration of the supernatant (antibody titer) was determined by protein A HPLC and ELISA at the end of each passage. From these data, the cell specific productivity (qP) for each passage was calculated using the following formula:

$$qP = \frac{P2 - P1}{(D2 - D1)/2 * \Delta t}$$

qP [pg/cell/d]: cell specific productivity,
$P_1$ [μg/ml]: antibody titer at the beginning of the passage,
$P_2$ [μg/ml]: antibody titer at the end of the passage,
$D_1$ [cells/ml]: viable cell density at the beginning of the passage,
$D_2$ [cells/ml]: viable cell density at the end of the passage,
$\Delta t$ [d]: duration of the passage.

The qP values were plotted against the age of culture at the end of the respective passage in generations. A linear trend line was calculated over all qP data points and the relative alteration of the qP (in percent) over the period was calculated in house, according to the following equation:

$$\Delta qP = \frac{m * a}{qP_0 * 100}$$

ΔqP [%]: percentage alteration of qP,
m [pg/cell/d/generation]: slope of linear trend line,
a [no. of generations]: age of culture,
$qP_0$: y-axis intercept of linear trend line.

In regard to lower number of data points obtained for each sample the average of the last three qP values was divided by the average of the first two qP values and displayed in percent to obtain ΔqP.

$$\Delta qP = \frac{\text{average } qP \text{ EOS}}{\text{average } qP \text{ PSB}} * 100$$

Average qP EOS: average of last three qP values
Average qP PSB: average of the first two qP values Treatment of Recombinant CHO Cell Lines, Used for Identification of Epigenetic Marker 32 CHO cell lines of two projects were used to identify epigenetic markers, predicting target gene expression two months in advance. For both projects data including antibody concentration, C-425 methylation status of hCMV-MIE promoter and copy number were collected over a period of 60 generations (~2 months). Project H comprises 20 CHO-K1 cell lines expressing a human antibody of class IgG under control of hCMV-MIE promoter. The vector further comprises a nucleic acid sequence encoding glutamine synthetase, making cells susceptible to methionine sulfoximine (MSX) selection. Project T comprises 12 CHO-K1 cell lines expressing a human antibody of class IgG under control of hCMV-MIE promoter. Those cell lines are prone to methotrexate (MTX) selection because of the transgene of the murine dihydrofolate reductase. Frozen start cultures were thawed and cultivated in appropriate mediums comprising 250 nM MTX or 140 μM MSX. After two weeks (time point PSB) of cultivation cells were harvested and chromatin immunoprecipitation with following antibodies was carried out.

TABLE 22 list for project T

| Target | Name | company | ChIP grade | host | cat. no. |
|---|---|---|---|---|---|
| H3K4me3 | ChIPAb+ Trimethyl-Histone H3 (Lys4) | Millipore | v | rabbit monoclonal | 17-614 |
| H3K27me3 | ChIPAb+ Trimethyl-Histone H3 (Lys27) | Millipore | v | rabbit polyclonal | 17-622 |
| H3K9me3 | Anti-Histone H3 (trimethyl K9) antibody | Abcam | v | rabbit polyclonal | ab8898 |
| H3 | Anti-Histone H3 antibody | Abcam | v | rabbit polyclonal | ab1791 |
| H3ac | Anti-acetyl-Histone H3 | Millipore | v | rabbit polyclonal | 06-599 |

TABLE 23 list for project H

| target | Name | company | ChIP grade | host | cat. no. |
|---|---|---|---|---|---|
| H3K4me3 | Histone H3K4me3 antibody (pAb) | activemotif | √ | rabbit Polyclonal | 39915 |
| H3ac | Anti-acetyl-Histone H3 Antibody | Millipore | √ | rabbit polyclonal | 06-599 |
| H3K9me3 | ChIPAb+ Trimethyl-Histone H3 (Lys9) | Millipore | v | polyclonal | 17-625 |
| H3K27me3 | ChIPAb+ Trimethyl-Histone H3 (Lys27) | Millipore | v | rabbit Polyclonal | 17-622 |
| H3 | Anti-Histone H3 antibody | Abcam | √ | Rabbit polyclonal | ab1791 |

TABLE 24

Quantitative was performed with the following primers:

| SEQ ID NO: | Primer NO: | Target | Sequence |
|---|---|---|---|
| 32 | 396 | hCMV-MIE forward 1 | TACATCAATGGGCGTGGATA |
| 33 | 397 | hCMV-MIE reverse 1 | AAGTCCCGTTGATTTTGGTG |
| 34 | 386 | Gusb forward 1 | CAGGGTGGGATGCTCTTC |
| 35 | 387 | Gusb reverse 1 | GCCGGTTTTCCGAGAAGT |
| 36 | 431 | Eif3i forward 1 | GTTCCCGGCACTGACACT |
| 37 | 432 | Eif3i reverse 2 | ACTTGATCTGCGTGATGGAC |
| 38 | 484 | Fox2a forward 1 | ATCACCCGTACTGCTGCTCT |
| 39 | 485 | Fox2a reverse | GAGGCTTCTGGGGATCTCTT |
| 40 | 468 | Gata5 forward 1 | CACCTACCCCATCCTGTCTG |
| 41 | 469 | Gata5 reverse 1 | GAGGAGGTGAAGGCAAAGTCT |
| 42 | 388 | Rho forward 1 | AGCCTCGGTCTCTATTGACG |
| 43 | 389 | Rho reverse 1 | CGTTGGAGAAGGGCACATAA |
| 52 | 474 | UNC13c forward 1 | GGGTGCTTTACGGAAACTGA |
| 53 | 475 | UNC13c reverse 1 | GCTTCTTATGCCCCAGGTTT |

Transgene Copy Number Determination

Transgene copy number examination was performed as previously described (Osterlehner, et al. 2011). Transgene copy per sample ($LC_S$ or $HC_S$) was extrapolated from a standard curve of a dilution series. Assuming that each cell contain approximately 6 pg DNA the number of transgenes per cell ($LC_{cell}$) was calculated as follows.

$$LC_{cell} = \frac{LC_s}{50000} * 6$$

$$HC_{cell} = \frac{HC_s}{50000} * 6$$

Computational Analysis with JMP

Percentage methylation of C-179 and acetylation per histone 3 close to hCMV-MIE at begin of cultivation phase were plotted against the alteration over 60 generations of specific productivity (ΔqP) in a standard least squares fit model. Therefore software JMP10 (JMP® 10.0.1 Release: 2, 64-bit edition; SAS Institute Inc.) was used and P-values of effect leverage plot were calculated. In addition outlier analyses were performed by employing the Jackknife technique. The LogWorth statistic was performed to identify the best split node to subdivide cell populations by stability and degree of epigenetic modification (Sall 2002).

EXAMPLE 2

Generation of Recombinant CHO Cell Lines

Recombinant cell lines expressing a human antibody of class IgG were generated by stable transfection of CHO-K1 or CHO-DG44 suspension growing cells with a vector encoding the light and heavy chain of antibody comprising a human immunoglobulin kappa light chain and a human immunoglobulin gamma 1 or gamma 4 heavy chain. The vector further comprised a nucleic acid encoding murine dihydrofolate reductase (DHFR) or glutamine synthetase (GS). Light and heavy chain expression cassettes were both under the control of a human CMV major-immediate-early promoter and enhancer (SEQ ID NO: 01). Transfection of cells was either performed by nucleofection (Lonza Cologne GmbH or Amaxa Biosystems) or by electroporation using Gene Pulser XCell (BIO-RAD).

For example, CHO-K1 or CHO-DG44 suspension were transfected with linearized plasmid DNA, using the Nucleofector device in combination with the Nucleofector Kit V (Lonza Cologne GmbH, Cologne, Germany) or by electroporation using the Gene Pulser XCell (Bio-Rad, Hercules, Calif.), according to the manufacturers' protocols. Transfected cells were seeded into 96 or 384-well plates containing thymidine-free medium with various concentrations of methotrexate (MTX) as selection agent or methionine sulfoximine (MSX) as selection agent. After three weeks, antibody-expressing cell lines were identified by measuring antibody titers in the culture medium by ELISA. Top producers were expanded to higher volumes, subcloned by limiting dilution and cryoconserved.

Stably transfected cells were selected in thymidine and protein free medium containing 20 nM to 1200 nM Methotrexate (MTX) or 140-160 μM methionine sulfoximine (MSX) as selection agent. Antibody expressing cells or cell lines were identified by measuring antibody titers in the culture medium and subcloned by limiting dilution and/or FACS single cell deposition.

The cells were propagated in disposable 50 ml or 125 ml vented shake flasks under standard humidified conditions (95% rH, 37° C., and 5% to 8% $CO_2$) at a constant agitation rate of 120 rpm/min to 150 rpm/min. Every 3-4 days the cells were split into fresh medium. Density and viability of the cultures were determined using the CASY TT or Cedex HiRes cell counter (Roche Innovates AG, Bielefeld, Germany). Furthermore, standard cell culture techniques were applied as described e.g. in Current Protocols in Cell Biology, Bonifacino, J. S. et al. (Eds), John Wiley & Sons, Inc., New York (2000).

EXAMPLE 3

Long-Term Cultivation and Production

CHO cell lines obtained according to Example 2 were investigated for long-term productivity.

The cells were tested for phenotypic, i.e. production, stability for 35 to 70 generations in the absence of a selection agent. The cells were continuously cultivated in vented 125 ml shake flasks containing 50 ml medium without selection agent and diluted twice a week with fresh medium. Seeding density was 2 to $3 \times 10^5$ cells/ml. Prior to passage viable cell density and viability were determined. The age of the culture in generations at the end of each passage was calculated according to the following equation:

$$a_2 = a_1 + \ln(D_2/D_1)/\ln 2 \quad \text{(Formula 1)}$$

with $a_2$ [no. of generations]: age of the culture at the end of the passage, $a_1$ [no. of generations]: age of the culture at the beginning of the passage i.e. age of the culture at the end of the previous passage, $D_1$ [cells/ml]: viable cell density at the beginning of the passage, $D_2$ [cells/ml]: viable cell density at the end of the passage.

Antibody concentration in the supernatant (antibody titer) was determined by protein A HPLC at the end of each passage. From these data, the specific production rate (SPR) for each passage was calculated using the following formula:

$$SPR = P_2 - P_1/((D_2+D_1)/2 * \Delta t) \quad \text{(Formula 2)}$$

with

SPR [pg/cell/d]: specific production rate, $P_1$ [µg/ml]: antibody titer at the beginning of the passage, $P_2$ [µg/ml]: antibody titer at the end of the passage, $D_1$ [cells/ml]: viable cell density at the beginning of the passage, $D_2$ [cells/ml]: viable cell density at the end of the passage, $\Delta t$ [d]: duration of the passage.

The SPR values were plotted against the age of culture at the end of the respective passage in generations. A linear trend line was calculated over all SPR data points and the relative alteration of the SPR (in percent) over the period tested was calculated according to the following equation:

$$\Delta SPR = m*a/SPR_0*100 \quad \text{(Formula 3)}$$

with $\Delta SPR$ [%]: percentual alteration of SPR, m [pg/cell/d/generation]: slope of linear trend line, a [no. of generations]: age of culture, $SPR_0$: y-axis intercept of linear trend line.

Almost all the cell lines showed a decrease in productivity, whereby the loss of productivity tends to be stronger under condition without selection agent

TABLE 56

Change in SPR during cultivation of five cell lines in the presence and/or absence of selection agent.

| parental cell line CHO-K1 | Selection Agent MTX | |
| --- | --- | --- |
| Sample No. | ΔSPR (−) MTX 30 generations | ΔSPR (−) MTX 60 generations |
| K18.1 | −59% | n.d. |
| G25-10 | −29% | −57% |
| G25-17 | −73% | n.d. |
| G42-5 | 0% | −1% |

| parental cell line CHO-DG44 | Selection Agent MTX | |
| --- | --- | --- |
| Sample No. | ΔSPR (−) MTX 30 generations | ΔSPR (−) MTX 60 generations |
| 43-16 A10 | −49% | n.d. |

| parental cell line CHO-K1 | Selection Agent MSX | |
| --- | --- | --- |
| Sample No. | ΔSPR (+) MSX 60 generations | ΔSPR (−) MSX 60 generations |
| H-1 | −47% | −80% |
| H-2 | −71% | −70% |
| H-3 | −73% | −90% |
| H-4 | −69% | −70% |
| H-5 | −40% | −49% |
| H-6 | −80% | −72% |
| H-7 | −66% | −82% |
| H-8 | −67% | −76% |
| H-9 | −87% | −77% |
| H-10 | −16% | −73% |
| H-11 | −43% | −96% |
| H-12 | −42% | −33% |
| H-13 | 8% | −19% |
| H-14 | 7% | 5% |
| H-15 | −17% | −40% |
| H-16 | 16% | −33% |
| H-17 | −13% | −31% |
| H-18 | −68% | e.i.m. |
| H-19 | −11% | 3% |
| H-20 | −40% | −81% |

| Host Cell line CHO-K1 | Selection Agent MTX | |
| --- | --- | --- |
| Sample No. | ΔSPR (+) MTX 60 generations | ΔSPR (−) MTX 60 generations |
| T-1 | −35% | −34% |
| T-2 | −31% | −72% |
| T-3 | −82% | −97% |
| T-4 | −23% | −47% |
| T-5 | −16% | −22% |
| T-6 | −14% | −20% |
| T-7 | −16% | −32% |
| T-8 | −65% | −79% |
| T-9 | −28% | −49% |
| T-10 | 4% | 1% |
| T-11 | −10% | −22% |
| T-12 | −32% | −23% | n.d. = not determined.
e.i.m. = error in measurement

EXAMPLE 4

Identification of Methylated CpG Sites within Human CMV Major-Immediate-Early Promoter/Enhancer DNA by Bisulfite Treatment and DNA Sequencing The human CMV major-immediate-early promoter/enhancer fragment (SEQ ID NO: 01) used for the expression of antibody light and heavy chain genes contains 33 CpG sites.

Genomic DNA was isolated from the CHO cell lines K18.1, G25-10, G25-17, G42-5 and 43-16 A10 using the Allprep DNA/RNA Mini Kit from Qiagen (Hilden, Germany). Five microgram DNA was cleaved with the enzyme Drat and quantified by measuring the extinction at 260 nm. One hundred nanogram DNA was subjected to bisulfite treatment and purified using the EpiTect Bisulfite Kit (Qiagen, Hilden, Germany). Bisulfite treated DNA was recovered in 20 µl RNAse-free water (Qiagen, Hilden, Germany).

In order to amplify strand A (forward) of the human CMV major-immediate-early promoter/enhancer fragment (SEQ ID NO: 02), 1 µl bisulfite treated DNA was combined with 24 µl PCR master mix and subjected to PCR using the GeneAmp® PCR System 9700 (Applied Biosystems Inc., USA).

24 µl PCR master mix comprised:
1 µl forward primer 227 of SEQ ID NO: 06 (10 pmol/µl),
1 µl reverse primer 229 of SEQ ID NO: 08 (10 pmol/µl),
22 µl Platinum® PCR SuperMix HighFidelity (Invitrogen Corp., USA).

Forward primer 227 is complementary to the 5'-end of the human CMV major-immediate-early promoter/enhancer fragment. Reverse primer 229 binds downstream within the 5'-UTR of the immunoglobulin genes.

The PCR conditions were as follows:

TABLE 26

|  |  | temp. | duration |
|---|---|---|---|
| Step 1 | Denaturation | 95° C. | 10 min. |
| Step 2: | PCR Denaturation | 94° C. | 30 sec. |
| # cycles: 45 | Annealing | 50° C. | 2 min. |
|  | Extension | 68° C. | 2 min. |
| Step 3 | Final Extension | 72° C. | 10 min. |
| Step 4 | Soak | 4° C. | indefinite |

The PCR product was checked for size and purity by agarose gel electrophoresis and cloned in the vector pCR4 (Invitrogen Corp., USA) using the TOPO TA cloning kit (Invitrogen Corp., USA). Plasmid clones were isolated and analyzed by restriction digest and agarose gel electrophoresis. For each cell line, 19 to 22 plasmids containing the insert were sequenced. In order to estimate the deamination efficiency of the bisulfite treatment at non CpG sites, the number of residual cytosine at non-CpG sites was determined. The percentual deamination efficiency was calculates as follows:

$$E_{mod}=100-(C_{res}/C_{total}*100) \quad \text{(Formula 4)}$$

with
$E_{mod}[\%]$: deamination efficiency,
Cres: number of residual cytosine at non-CpG sites in all inserts analyzed, PCR primers sites excluded,
$C_{total}$: number of cytosine in the non-bisulfite treated CMV promoter/enhancer fragment, PCR primer sites excluded, multiplied by the number of inserts analyzed, i.e. 107*20.

It was found that the deamination efficiency at non-CpG cytosine was greater than 99% in all samples (Table 12).

TABLE 27

Deamination efficiency at non-CpG cytosine.

|  | Cell line K18.1 | Cell line G25-10 | Cell line G25-17 | Cell line G42-5 | Cell line 43-16 A10 |
|---|---|---|---|---|---|
| $E_{mod}$ | 99.1% | 99.3% | 99.5% | 99.3% | 99.3% |

Protection of 5-methyl cytosine from deamination was confirmed by bisulfite treatment and subsequent cloning and sequencing of plasmid DNA isolated from dcm$^+$E. coli. Dcm$^+$E. coli methylate the internal cytosine residues within the sequences CCAGG or CCTGG (dcm-sites). It was found that the deamination efficiency was 99% at non-dcm-sites and less than 5% at internal cytosine within dcm-sites.

To quantify the extend of DNA methylation at CpG sites within the bisulfite treated CMV promoter/enhancer fragment, the number of cytosine found at each CpG-site was determined and plotted for each analyzed cell.

Figure 1:
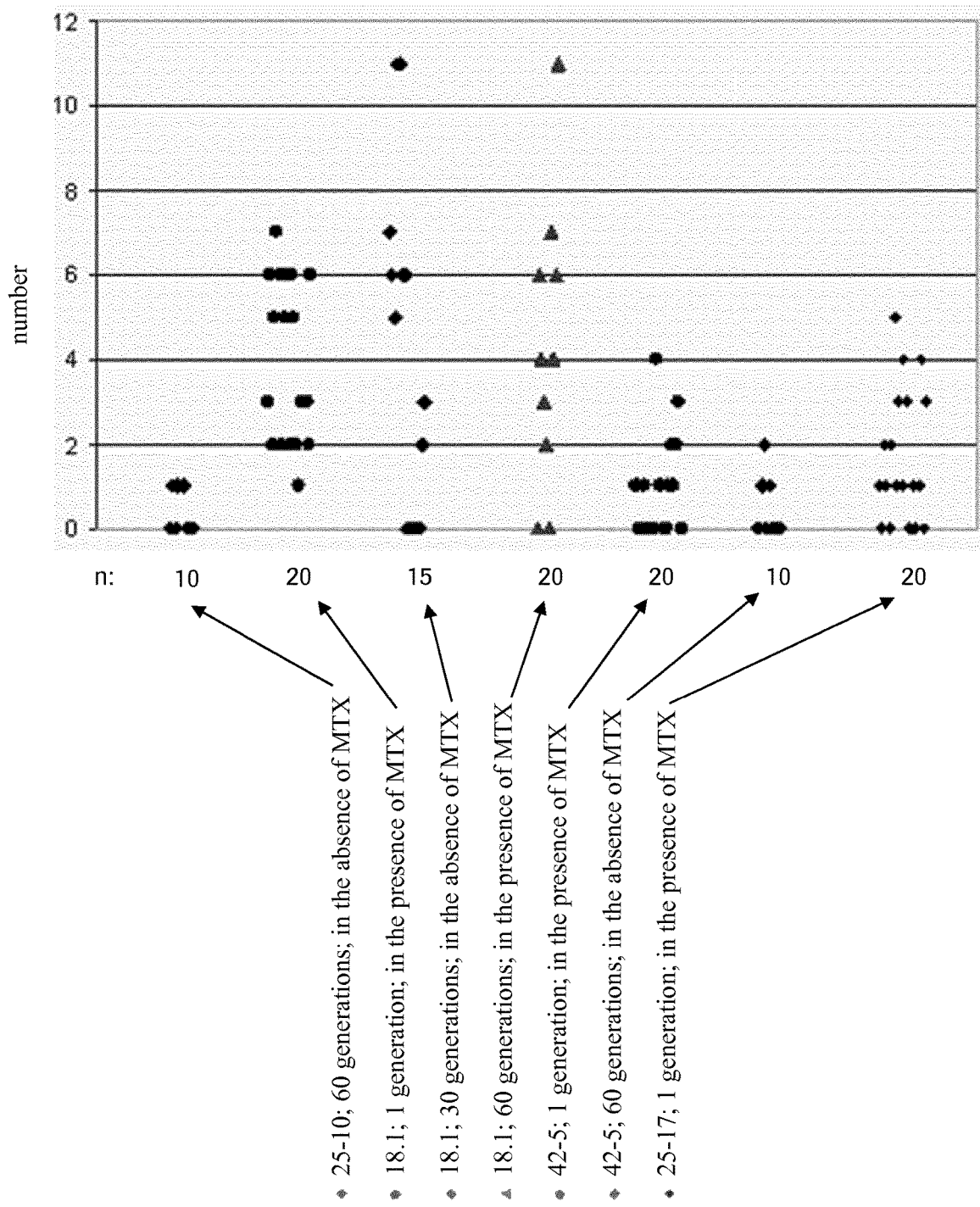
FIG. 1 Number of methylated CpG site of the hCMV-MIE promoter/enhancer obtained from different cell lines.
Figure 2:
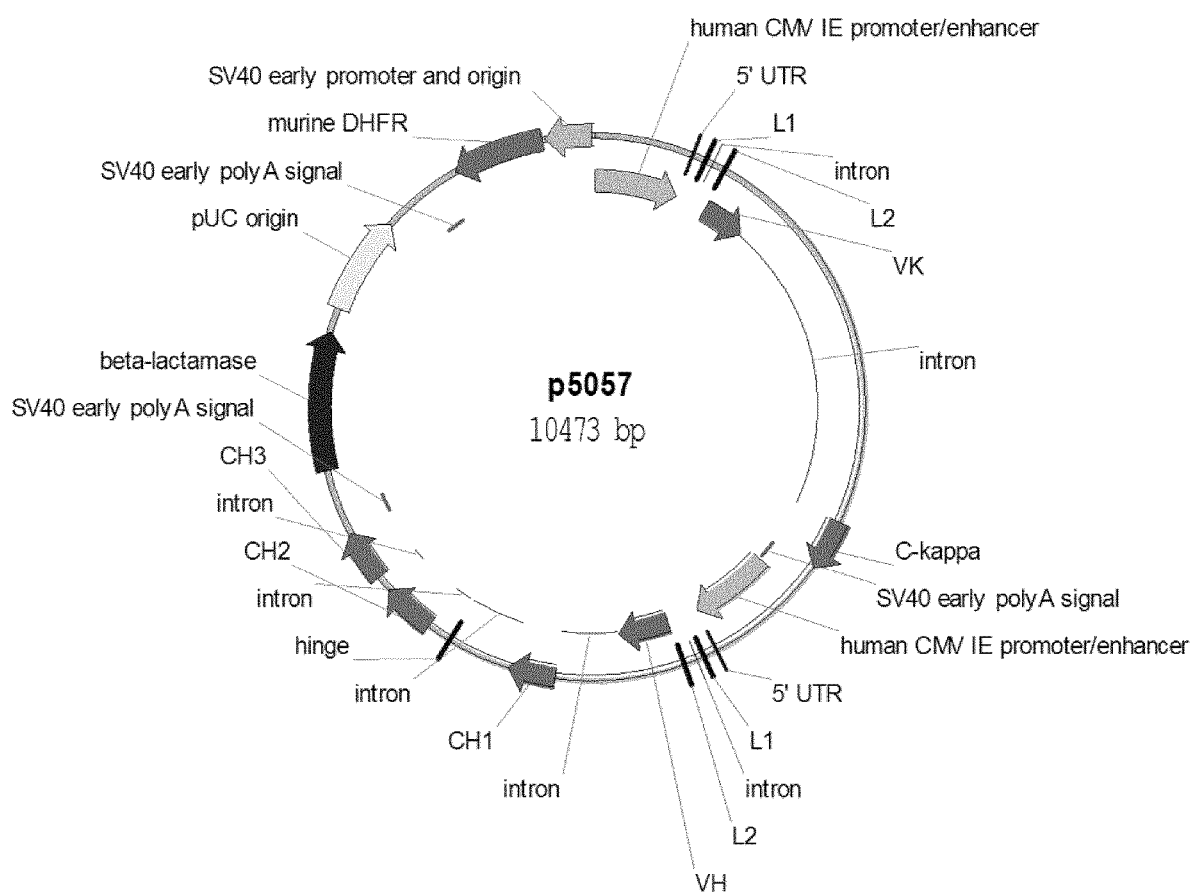
FIG. 2 Plasmid map of p5057.
Figure 3:
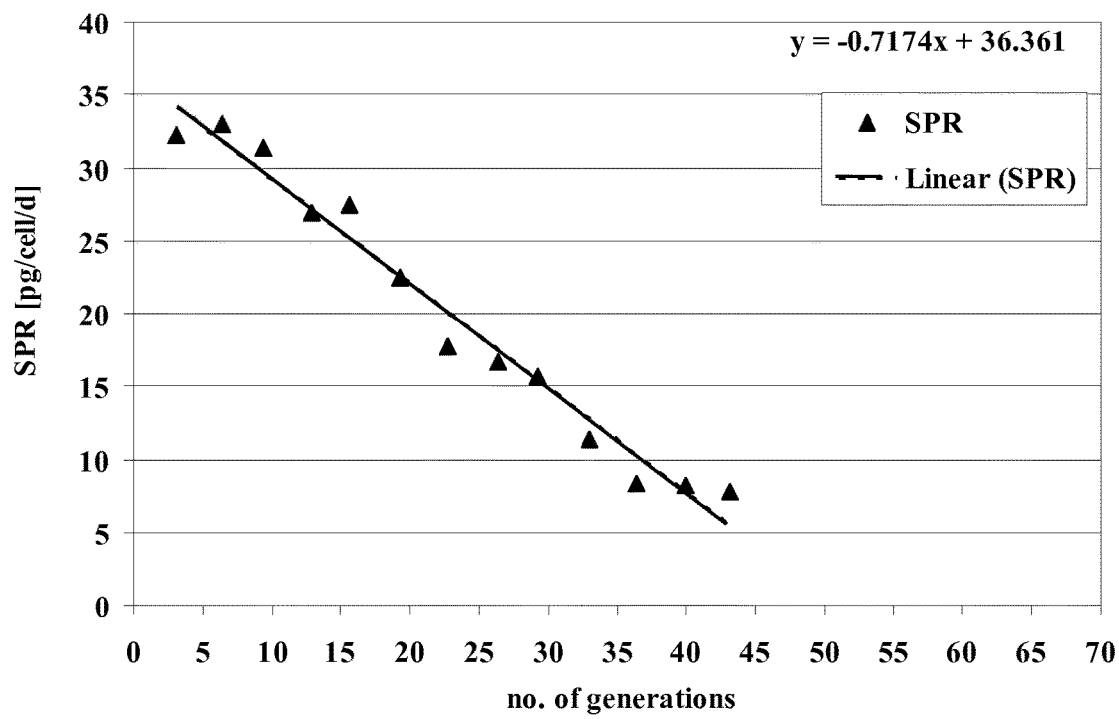
FIG. 3 A: Specific production rate in the absence of a selection agent of cell line K18.1 over multiple generations in a long-term production.
    B: Specific production rate in the absence of a selection agent of cell line G25-10 over multiple generations in a long-term production.
    C: Specific production rate in the absence of a selection agent of cell line G25-17 over multiple generations in a long-term production.
    D: Specific production rate in the absence of a selection agent of cell line G42-5 over multiple generations in a long-term production.
    E: Specific production rate in the absence of a selection agent of cell line 43-16 A10 over multiple generations in a long-term production.
Figure 3:
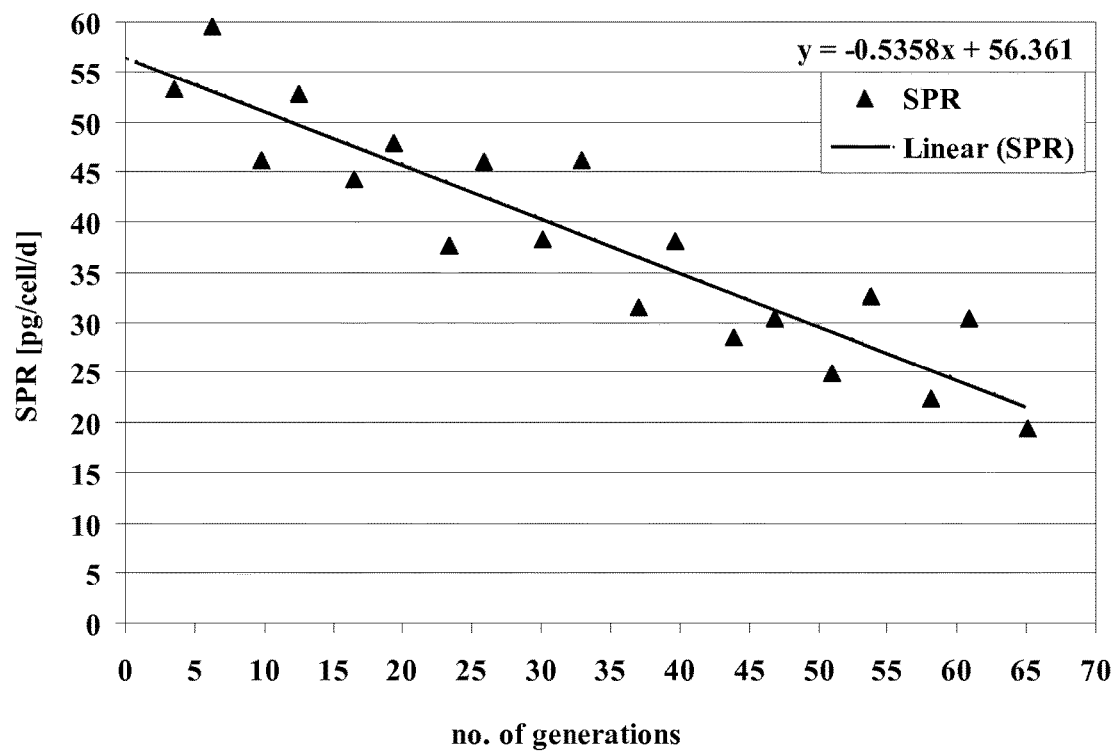
Figure 3:
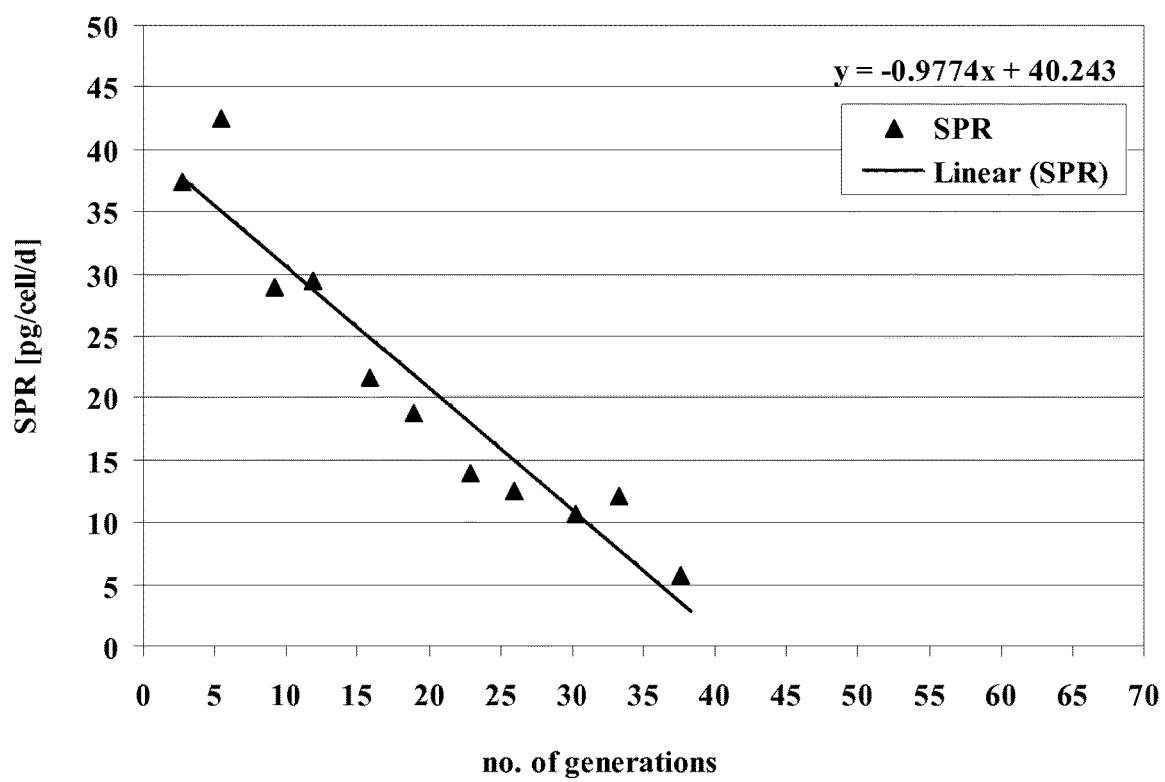
Figure 3:
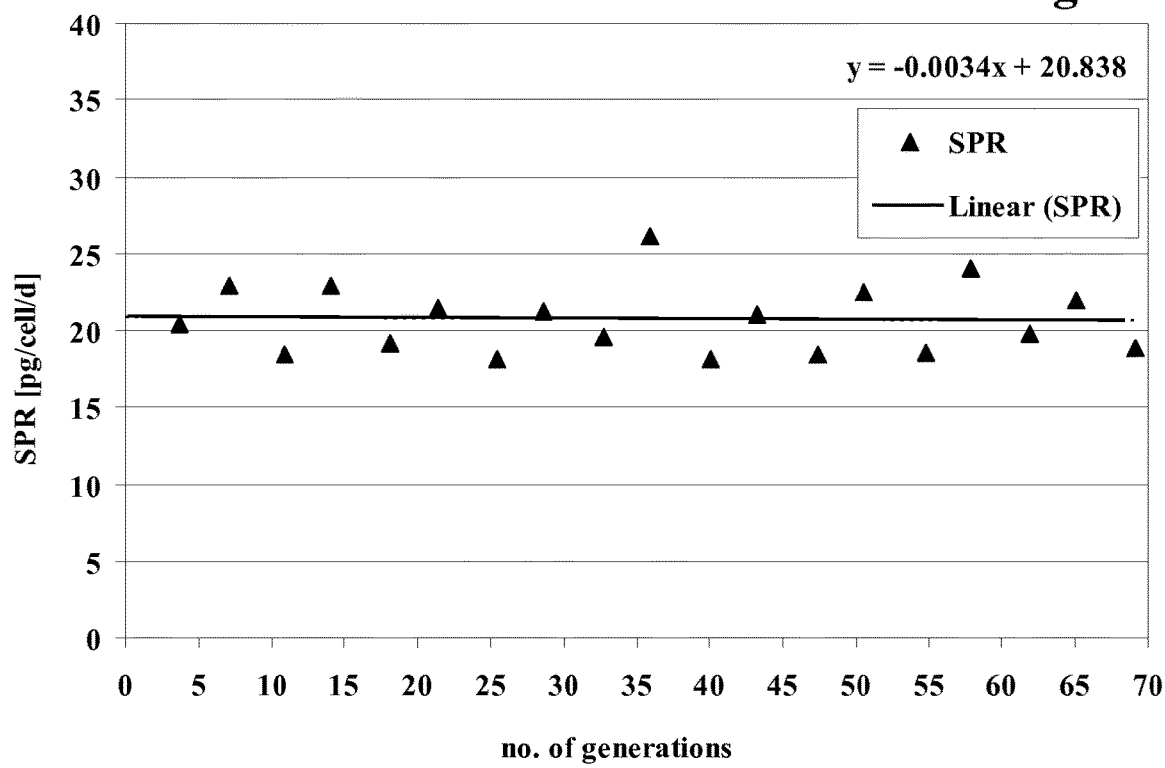
Figure 3:
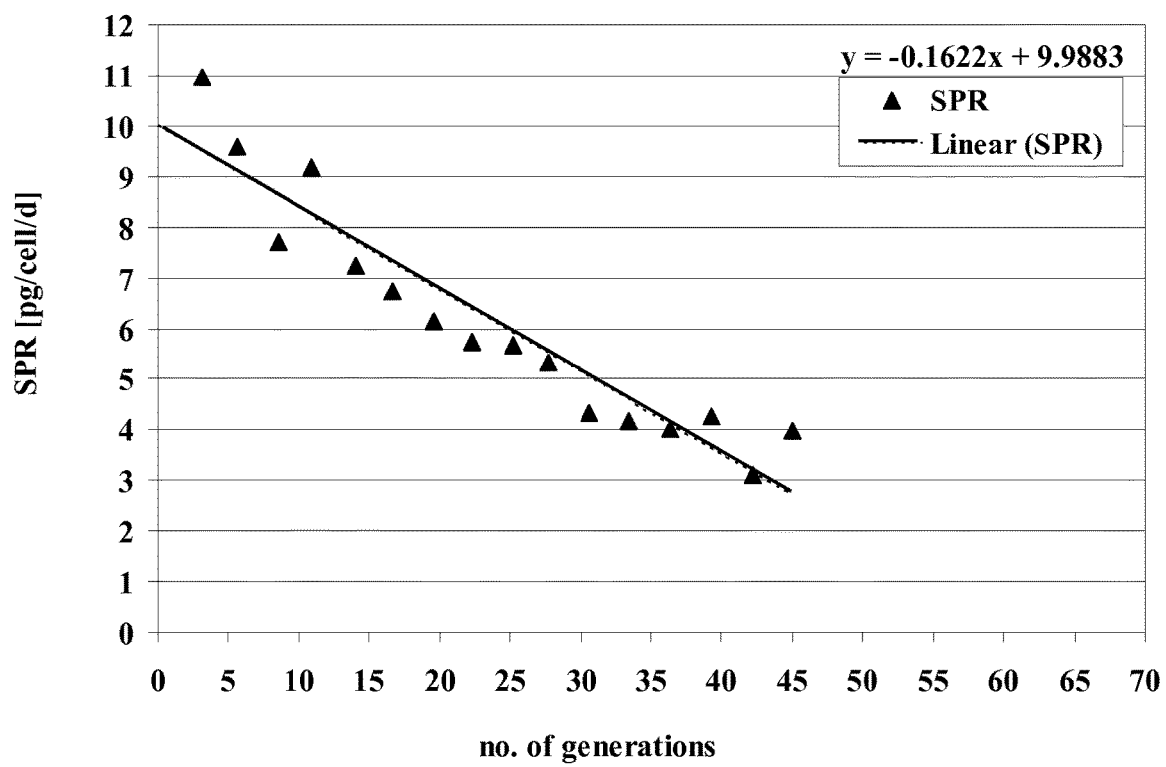

Cell line K18.1 is highly methylated (FIG. 3A). The frequency of methylation accumulates in 3 clusters, one at the 5'-end, one the 3'-end and one at around position 400. The highest degree of methylation was found at position 425. Fourteen out of the twenty-two inserts sequenced had a cytosine here.

Methylation of the CMV promoter from cell line 43-16 A10 was noticeable (FIG. 3E). The distribution of methylation was similar to the distribution observed with cell line K18.1. Position 425 was methylated most often. Five of the twenty inserts sequenced contained a cytosine in this position.

In the three other cell lines investigated cytosine were detected only sporadically at CpG sites (FIGS. 3B, 3C and 3D).

EXAMPLE 5

Quantitative Methylation Specific PCR of Bisulfite Treated Human CMV Major-Immediate-Early Promoter/Enhancer DNA In this example a methylation specific real-time qPCR as method to detect methylation at a CpG position, to be more precise at position 425 of the hCMV promoter nucleic acid, is reported.

Two sets of primers were designed:
a methylation specific primer pair (MSP primer pair) selectively amplifying deaminated CMV promoter DNA with a cytosine in position 425 representing DNA that is methylated at position 425, and
a universal primer pair amplifying deaminated CMV promoter DNA irrespective of the methylation status.

The universal primer pair was used for normalization. To be used in the same PCR run both primer pairs should have similar melting points.

The designing of primers sensing methylation at position 425 was complicated by the presence of two additional CpG sites in close proximity (position 416 and position 437). Methylation sensitive primers should detect 5mC425 independent of the methylation status of position 416 and position 437.

Four deaminated human CMV major-immediate-early promoter/enhancer fragments isolated in Example 4 representing the possible sequence variations in positions 425 and 437: #11, #62, #01 and #04 (Table 28, SEQ ID NO: 19, SEQ ID NO: 20, SEQ ID NO: 21, SEQ ID NO: 22) have been used as qPCR templates for methylation specific PCR and universal primer pairs.

TABLE 28

Expected results for MSP and universal primer pairs in qPCR.

| Templates | #11 | #62 | #01 | #04 |
|---|---|---|---|---|
| Pos. 425 | T | C | C | T |
| Pos. 437 | T | C | T | C |
| Amplification | | | | |
| MSP primer pair | − | + | + | − |
| Universal primer pair | + | + | + | + |

With the universal primer all four templates can be comparably amplified whereas the methylation specific primer pair can selectively amplify template #62 and template #01. ΔCp should be as small as possible between the methylation specific primer pair and the universal primer pair on templates #62 and template #01. Cp values obtained with the methylation specific primer pair on template #11 and template #04 should be as high as possible, i.e. ΔCp compared to amplification with the universal primer pair should be maximal.

For qPCR the LightCycler® 480 II system was employed (Roche Diagnostics GmbH, Mannheim, Germany) and samples were prepared using the LightCycler® 480 SYBR Green I Master (Roche Diagnostics GmbH, Mannheim, Germany). Five microliters template solution containing 0.05 ng DNA was combined with 15 μl PCR master mix in a well of a 96-well multi well plate.

15 μl PCR master mix comprised:
- 4.2 μl water,
- 0.4 μl forward primer 239, 263 or 264 (also possible primer 227, 228, 240, 238) (10 pmol/μl),
- 0.4 μl reverse primer 237, 254, 262, 265, 266, 267 or 268 (also possible primer 229) (10 pmol/μl),
- 10 μl SYBR Green I Master.

The multi well plate was sealed with a LightCycler® 480 sealing foil (Roche Diagnostics GmbH, Mannheim, Germany) and centrifuged at 1,500×g for 2 minutes. Afterwards the plate was mounted into the LightCycler® 480 system and subjected to qPCR. Each sample was tested in duplicate, triplicate or quadruplicate. To allow determination of absolute copy numbers, standard curves were generated for the LC and the HC transgene, using the linearized expression plasmid as standard. Standard dilutions contained $2.5 \times 10^7$, $2.5 \times 10^6$, $2.5 \times 10^5$, $2.5 \times 10^4$ or $2.5 \times 10^3$ plasmid copies. Genomic DNA was tested in triplicate; standards were run in quadruplicate.

TABLE 29

The used PCR conditions were:

| step | | No. of cycles | T [° C.] | t [mins:s] | ramp rate [° C. s−1] | acquisition |
|---|---|---|---|---|---|---|
| denaturation | | 1 | 95 | 10:00 | 4.40 | — |
| real-Time PCR | denaturation | 45 | 95 | 00:10 | 4.40 | — |
| | annealing | | 57 to 59 | 00:15 | 2.20 | — |
| | elongation | | 72 | 00:07 | 4.40 | — |
| | detection | | 66 | 00:01 | 2.20 | single |
| melting curve | denaturation | 1 | 95 | 00:05 | 4.40 | — |
| | annealing | | 60 | 01:00 | 2.20 | — |
| | melting | | 90 | 00:00 | 0.11 | continuous |
| cooling | | 1 | 40 | 00:30 | 2.2 | |

The collection and analysis of the data was done with the LightCycler® 480 software version 1.5. The apparent degree of methylation was calculated using the following formula, where ideal amplification efficiency was assumed (E=2).

$$mC_{app} = 2^{Cp(t)-Cp(m)} * 100 \qquad \text{(Formula 5)}$$

with $mC_{app}$ [%]: apparent degree of methylation,

Cp(t): Cp value obtained with universal primers,

Cp(m): Cp value obtained with methylation-specific primers.

Figure 6:
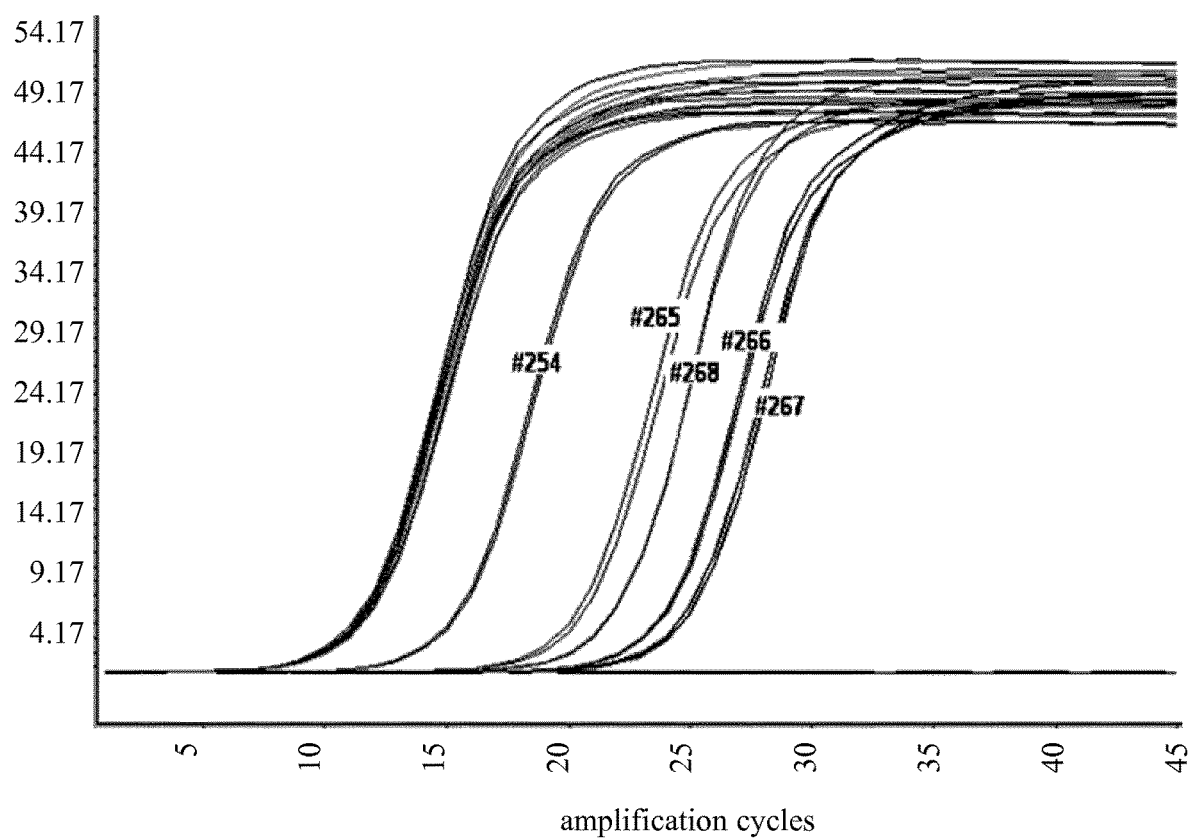
FIG. 6 PCR amplification curves for different methylation specific primer and primer pairs.

During primer evaluation, it was found that designing methylation specific primer, which are highly selective for deaminated CMV promoter DNA with a cytosine at position 425 ("methylated"), has to be performed with care. Primer 266 and 267 showed the maximal difference between Cp(#11) and Cp(#62), i.e. the highest selectivity for "methylated" DNA. Primer 265, 268 and 254 showed minor selectivity. The universal primer pair 263/237 was tested as control for minimal ΔCp (FIG. 6 and Table 30).

TABLE 30

Results of primer evaluation.

| Primer | Template | Mean Cp | STD Cp | ΔCp [Cp(#11)-Cp(#62)] | Stdev. ΔCp [Cp(#11)-Cp(#62)] |
|---|---|---|---|---|---|
| 263 + 237 | #11 | 11.71 | 0.06 | 0.23 | 0.06 |
| | #62 | 11.48 | 0.01 | | |
| 263 + 254 | #11 | 15.22 | 0.08 | 3.89 | 0.19 |
| | #62 | 11.32 | 0.17 | | |
| 263 + 265 | #11 | 20.29 | 0.23 | 8.74 | 0.23 |
| | #62 | 11.55 | 0.02 | | |
| 263 + 266 | #11 | 23.76 | 0.04 | 12.31 | 0.16 |
| | #62 | 11.45 | 0.16 | | |
| 263 + 267 | #11 | 24.74 | 0.14 | 13.05 | 0.16 |
| | #62 | 11.69 | 0.07 | | |
| 263 + 268 | #11 | 21.75 | 0.06 | 10.25 | 0.10 |
| | #62 | 11.51 | 0.09 | | |

Figure 5:
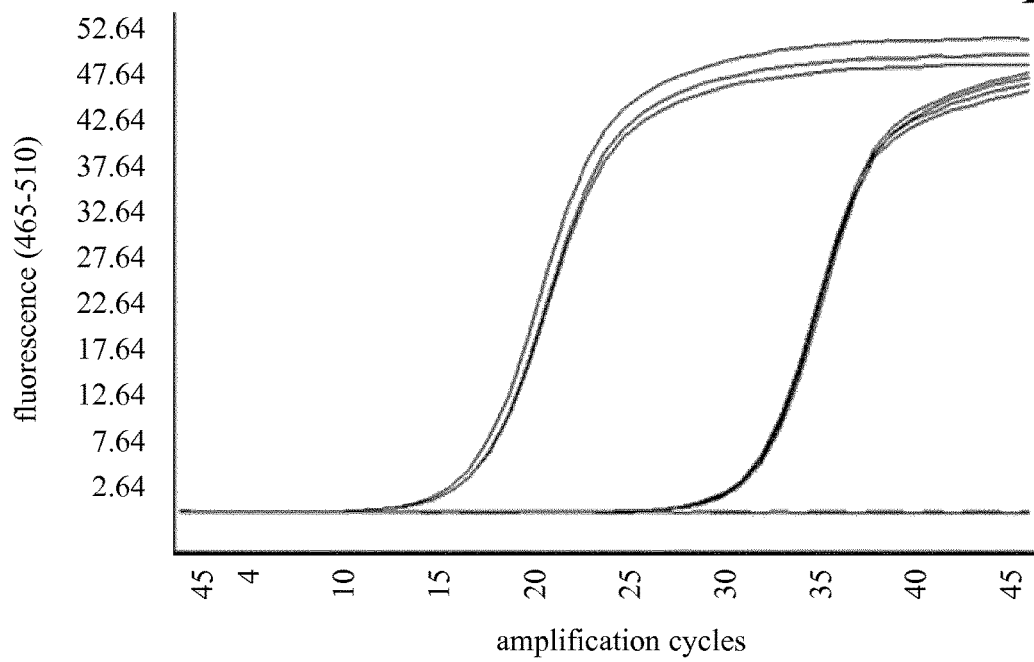
FIG. 5 Discrimination of hCMV-MIE promoter/enhancer which is methylated at site 425 from hCMV-MIE which is non-methylated at site 425 by methylation specific real-time qPCR; PCR amplification curves for templates #11 (A), #62 (B), #01 (C) and #04 (D).
Figure 5:
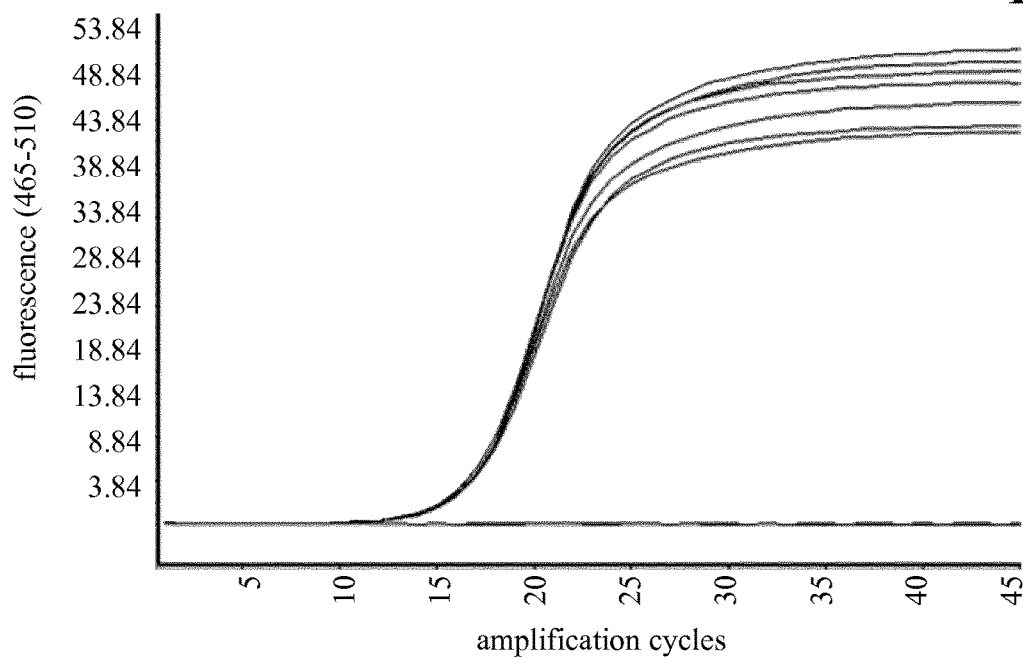
Figure 5:
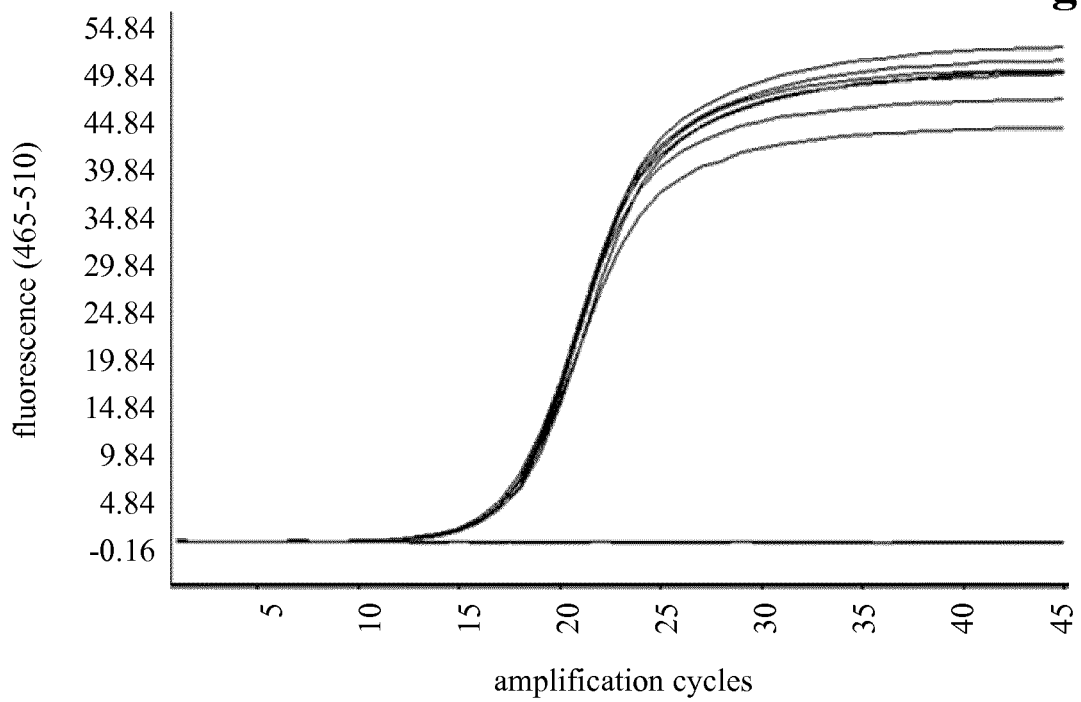
Figure 5:
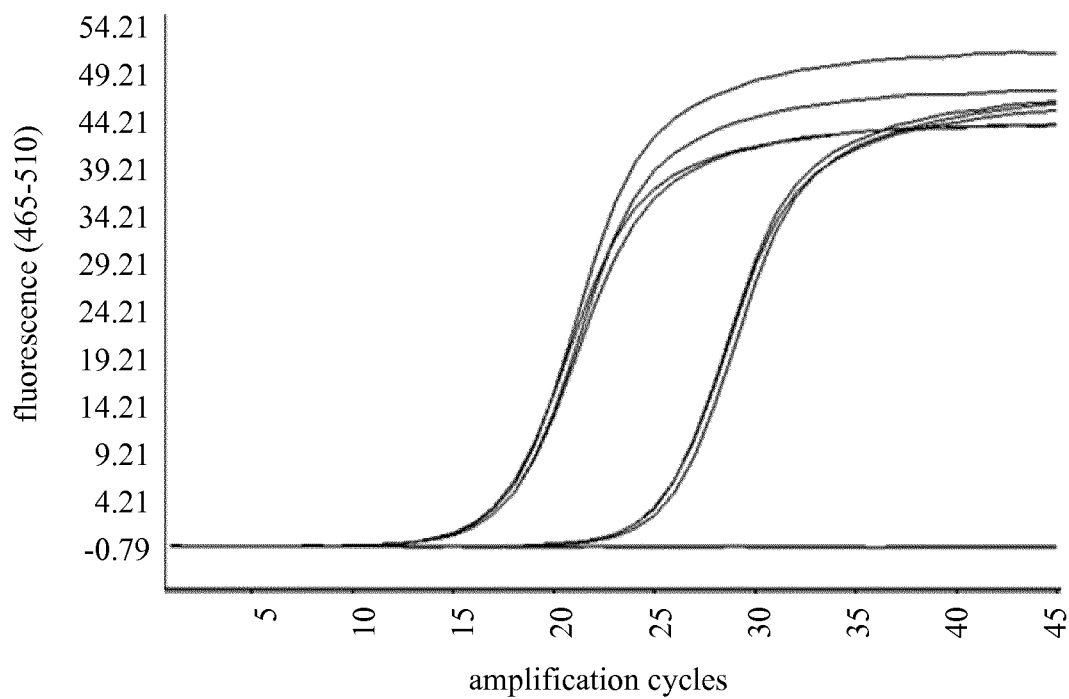

In FIG. 5 the results obtained with the methylation specific primer pair 239/267 (SEQ ID NO: 11, SEQ ID NO: 18) in combination with the universal primer pair 239/237 (SEQ ID NO: 11, SEQ ID NO: 09) is shown. Universal primer pair 239/237 amplified all four templates about equally well, whereas the methylation specific primer pair 239/267 amplified templates #62 and #01. Templates #11 and #4 are only poorly amplified by the primer pair 239/267.

Methylation frequency calculated from the Cp values was almost 100% for template #62 and template #01 and almost 0% for template #11 and template #04 (Table 15). This shows that methylation specific primer pair 239/267 in combination with the universal primer pair 239/237 can be used to discriminate CMV promoter DNA which is methylated at position 425 from CMV promoter DNA which is non-methylated at position 425 by real-time qPCR.

Additional universal and methylation specific primer pairs were found and are characterized in Table 31 and 32.

TABLE 31

Methylation specific reverse primer 267 and non-methylation specific reverse primer 237 combined with three different forward primers.

| | methylation site | | universal primer pairs | | | | | |
|---|---|---|---|---|---|---|---|---|
| | | | 239 (for) + 237 (rev) | | 263 (for) + 237 (rev) | | 264 (for) + 237 (rev) | |
| template | 425 | 437 | Cp(u) | Stdev | Cp(u) | Stdev | Cp(u) | Stdev |
| # 11 | T | T | 16.41 | 0.23 | 15.65 | 0.01 | 15.73 | 0.1 |
| # 62 | C | C | 16.73 | 0.04 | 16 | 0.08 | 16.38 | 0.25 |
| # 01 | C | T | 17.51 | 0.24 | 16.64 | 0.08 | 16.87 | 0.21 |
| # 04 | T | C | 17.58 | 0.24 | 16.18 | 0.16 | 16.54 | 0.22 |

| | methylation site | | C425 specific primer pairs | | | | | |
|---|---|---|---|---|---|---|---|---|
| | | | 239 (for) + 267 (rev) | | 263 (for) + 267 (rev) | | 264 (for) + 267 (rev) | |
| template | 425 | 437 | Cp(m) | Stdev | Cp(m) | Stdev | Cp(m) | Stdev |
| # 11 | T | T | 30.71 | 0.23 | 26.84 | 0.28 | 28.01 | 0.14 |
| # 62 | C | C | 16.74 | 0.13 | 16 | 0.38 | 16.82 | 0.29 |
| # 01 | C | T | 17.52 | 0.18 | 16.91 | 0.36 | 17.06 | 0.17 |
| # 04 | T | C | 25.34 | 0.24 | 23 | 0.14 | 23.68 | 0.27 |

| | methylation site | | ΔCp = Cp(m) − Cp(u) | | | | | |
|---|---|---|---|---|---|---|---|---|
| template | 425 | 437 | ΔCp | Stdev | ΔCp | Stdev | ΔCp | Stdev |
| # 11 | T | T | 14.3 | 0.33 | 11.19 | 0.28 | 12.28 | 0.17 |
| # 62 | C | C | 0.01 | 0.14 | 0 | 0.39 | 0.44 | 0.38 |
| # 01 | C | T | 0.01 | 0.30 | 0.27 | 0.37 | 0.19 | 0.27 |
| # 04 | T | C | 7.76 | 0.34 | 6.82 | 0.21 | 7.14 | 0.35 |

| | methylation site | | mCapp [%] | | | | | |
|---|---|---|---|---|---|---|---|---|
| template | 425 | 437 | mCapp | Stdev | mCapp | Stdev | % rel. | Stdev |
| # 11 | T | T | 0.0 | 0.0 | 0.0 | 0.0 | 0.0 | 0.0 |
| # 62 | C | C | 99.3 | 9.4 | 100.0 | 26.9 | 73.7 | 19.6 |
| # 01 | C | T | 99.3 | 20.7 | 82.9 | 21.2 | 87.7 | 16.4 |
| # 04 | T | C | 0.5 | 0.1 | 0.9 | 0.1 | 0.7 | 0.2 |

TABLE 32

Methylation specific reverse primer 266 and non-methylation specific reverse primer 237 combined with two different forward primers.

| | | | universal primer pairs | | | |
|---|---|---|---|---|---|---|
| | methylation site | | 263 (for) + 237 (rev) | | 264 (for) + 237 (rev) | |
| template | 425 | 437 | Cp(u) | Stdev | Cp(u) | Stdev |
| # 11 | T | T | 15.32 | 0.18 | 15.88 | 0.08 |
| # 62 | C | C | 15.73 | 1.07 | 16.22 | 0.57 |
| # 01 | C | T | 15.42 | 0.19 | 16.35 | 0.22 |
| # 04 | T | C | 15.4 | 0.24 | 16.8 | 1.12 |
| | | | C425 specific primer pairs | | | |
| | methylation site | | 263 (for) + 267 (rev) | | 264 (for) + 267 (rev) | |
| template | 425 | 437 | Cp(m) | Stdev | Cp(m) | Stdev |
| # 11 | T | T | 28.33 | 0.62 | 28.27 | 0.44 |
| # 62 | C | C | 15.64 | 0.25 | 16.32 | 0.35 |
| # 01 | C | T | 15.83 | 0.34 | 16.59 | 0.01 |
| # 04 | T | C | 22.39 | 0.15 | 22.83 | 0.88 |
| | methylation site | | ΔCp = Cp(m) − Cp(t) | | | |
| template | 425 | 437 | ΔCp | Stdev | ΔCp | Stdev |
| # 11 | T | T | 13.01 | 0.65 | 12.39 | 0.45 |
| # 62 | C | C | −0.09 | 1.10 | 0.1 | 0.67 |
| # 01 | C | T | 0.41 | 0.39 | 0.24 | 0.22 |
| # 04 | T | C | 6.99 | 0.28 | 6.03 | 1.42 |
| | methylation site | | mCapp [%] | | | |
| template | 425 | 437 | mCapp | Stdev | % rel. | Stdev |
| # 11 | T | T | 0.0 | 0.0 | 0.0 | 0.0 |
| # 62 | C | C | 106.4 | 81.1 | 93.3 | 43.3 |
| # 01 | C | T | 75.3 | 20.3 | 84.7 | 12.9 |
| # 04 | T | C | 0.8 | 0.2 | 1.5 | 1.5 |

For quantification of the degree of methylation over a broad range template #62 was mixed in different ratios with template #11. qPCR was performed as described above using primer pairs 239/237 and 239/267 and the recovery of template #62 in the template #11 background was calculated.

For calculation of the fraction of template #62 DNA, the amplification efficiencies of the primer pairs under the used conditions were determined. Serial dilutions of templates #62 and #11 from n=0.005 ng to 0.5 ng DNA were subjected to qPCR and the determined Cp values were plotted against log (n). A linear regression line was calculated using XLfit (Microsoft). The amplification efficiency was calculated using the following formula:

$$E = 10^{-1/m} \quad \text{(Formula 6)}$$

with

E: amplification efficiency, m: slope of linear trend line.

The amplification efficiencies of both primer pairs were calculated to be approximately 1.7. The following formula was employed for calculating the fraction of template #62 DNA:

$$mC = 1.7^{Cp(t)-Cp(m)} * 100 \quad \text{(Formula 7)}$$

with mC [%]: fraction of DNA methylated at position 425,

Cp(t): Cp value obtained with universal primer pair,

Cp(m): Cp value obtained with methylation specific primer pair.

Figure 7:
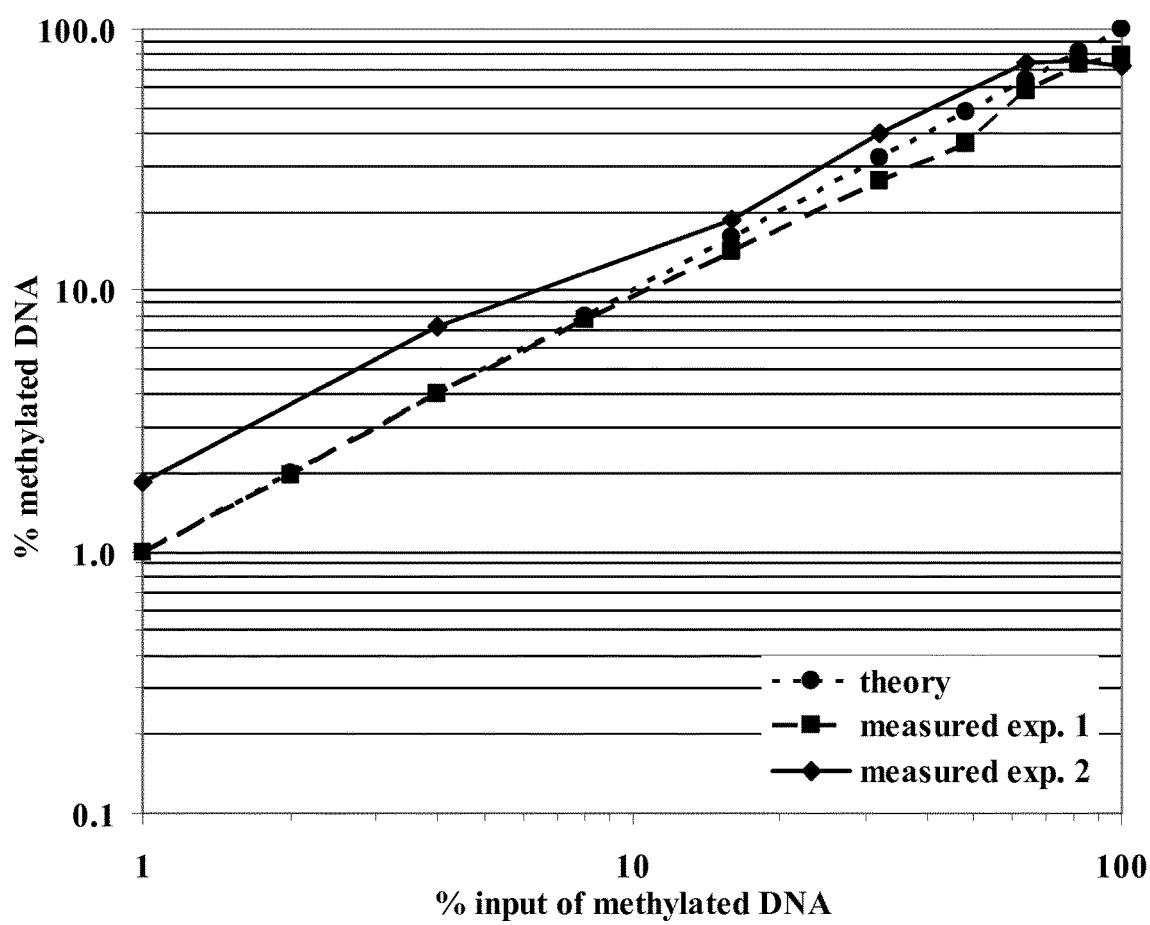
FIG. 7 Recovery of site 425 methylated hCMV-MIE promoter/enhancer in the background of non-methylated hCMV-MIE promoter/enhancer by methylation specific real-time qPCR.

The determined fractions of template #62 DNA from two independent experiments were plotted against the expected values (FIG. 7). Quantification of methylation between 1% and 100% can be performed.

EXAMPLE 6

Identification of Methylation Status of C-425 within Human CMV Major-Immediate-Early Promoter/Enhancer DNA by Bisulfite Treatment and Real Time Quantitative PCR
Bisulfite Treatment of Genomic DNA of CHO Cell Lines Assay was performed as described in Osterlehner et al. (supra). Genomic DNA was isolated from the CHO cell lines using the Allprep DNA/RNA Mini Kit from Qiagen (Hilden, Germany). Five microgram DNA was cleaved with the enzyme DraI and quantified by measuring the extinction at 260 nm. One hundred nanogram DNA was subjected to bisulfite treatment and purified using the EpiTect Bisulfite Kit (Qiagen, Hilden, Germany). Bisulfite treated DNA was recovered in 20 μl RNAse-free water (Qiagen, Hilden, Germany).

In order to amplify strand A (forward) of the human CMV major-immediate-early promoter/enhancer fragment (SEQ ID NO: 02), 1 μl bisulfate treated DNA was combined with 24 μl PCR master mix and subjected to PCR using the GeneAmp® PCR System 9700 (Applied Biosystems Inc., USA).

24 μl PCR master mix comprised

1 μl forward primer 227 of SEQ ID NO: 06 (10 pmol/μl),
1 μl reverse primer 229 of SEQ ID NO: 08 (10 pmol/μl),
22 μl Platinum® PCR SuperMix HighFidelity
(Life Technologies, Carlsbad, Calif.).

Forward primer 227 is complementary to the 5'-end of the human CMV major-immediate-early promoter/enhancer fragment. Reverse primer 229 binds downstream within the 5'-UTR of the immunoglobulin genes.

TABLE 33

The PCR conditions were as follows:

| | | temp. | duration |
|---|---|---|---|
| Step 1 | Denaturation | 95° C. | 10 min. |
| Step 2: | Denaturation | 94° C. | 30 sec. |
| PCR | Annealing | 50° C. | 2 min. |
| # cycles: 45 | Extension | 68° C. | 2 min. |
| Step 3 | Final Extension | 72° C. | 10 min. |
| Step 4 | Soak | 4° C. | indefinite |

The PCR product was checked for size and purity by agarose gel electrophoresis.
Methylation Specific Real Time Quantitative PCR LightCycler 480 II system (Roche Diagnostics GmbH, Mannheim, Germany) in combination with LightCycler 480 SYBR Green I Master (Roche Diagnostics GmbH, Mannheim, Germany) was used to perform qPCR. Fifty picogram plasmid DNA, 3 μl bislufite-treated genomic DNA, or 5 μl of a 1:50,000 dilution of the PCR product of primers 227 and 229 (SEQ ID NO: 06/08) with bislufite-treated genomic DNA were used as templates. For qPCR, templates were mixed with 4 or 12 pmol forward and reverse primer, 10 μl LightCycler 480 SYBR Green I Master, and nuclease-free water, to make up a total volume of 20 μl. To quantify the total human CMV major-immediate-early promoter/enhancer fragment DNA the primer pair 239/237 (SEQ ID NO: 11/09) was used, the methylated DNA at position C-425 (SEQ ID NO: 01) was detected with primer pair 239/267 (SEQ ID NO: 11/18). The PCR mix was added into a multi well plate.

The multi well plate was sealed with a LightCycler® 480 sealing foil (Roche Diagnostics GmbH, Mannheim, Germany) and centrifuged at 1,500×g for 2 minutes. Afterwards the plate was mounted into the LightCycler® 480 system and subjected to qPCR. Each sample was tested in duplicate, triplicate or quadruplicate.

TABLE 34

PCR conditions were as follows:

| step | | No. of cycles | T [° C.] | t [mins:s] | ramp rate [° C. s−1] | acquisition |
|---|---|---|---|---|---|---|
| denaturation | | 1 | 95 | 10:00 | 4.40 | — |
| real-Time PCR | denaturation | 45 | 95 | 00:10 | 4.40 | — |
| | annealing | | 57 to 59 | 00:15 | 2.20 | — |
| | elongation | | 72 | 00:07 | 4.40 | — |
| | detection | | 66 | 00:01 | 2.20 | single |
| melting curve | denaturation | 1 | 95 | 00:05 | 4.40 | — |
| | annealing | | 60 | 01:00 | 2.20 | — |
| | melting | | 90 | 00:00 | 0.11 | continuous |
| cooling | | 1 | 40 | 00:30 | 2.2 | |

Data collection and analysis was performed with Light-Cycler 480 software version 1.5 (Roche Diagnostics GmbH, Mannheim, Germany). The methylation of mC was expressed in percentage by following equation:

$$mC = E^{Cq(t)-Cq(m)} * 100 \qquad \text{(Formula 8)}$$

Cq(t) being the quantification cycle obtained with the universal primer pair 239/237, Cq(m) represents the quantification cycle obtained with the methylation-specific primer pair 239/267, and E being the amplification efficiency (MIQE Guidelines).

E was approximately 1.7 for 0.2 pmol/μl primer concentration and 2.0 for 0.6 pmol/μl primer concentration.

EXAMPLE 7

Human CMV Major-Immediate-Early Promoter/Enhancer Methylation Correlation with Long-Term Productivity
Methylation Specific qPCR with Pre-Amplified Human CMV Major-Immediate-Early Promoter/Enhancer Strand A As reported in Example 4 genomic DNA was isolated from CHO cell lines K18.1, G25-10, G25-17, G42-5 and 43-16 A10, cleaved with the enzyme DraI and deaminated by bisulfite treatment. The strand A of the human CMV major-immediate-early promoter/enhancer was amplified using primer 227 and 229.

The PCR product was diluted 1:50,000. Five microliters of each dilution were used for real-time qPCR. Primer 239 and 237 were employed for quantification of total CMV promoter DNA; primer 239 and 267 were employed for quantification of CMV promoter/enhancer DNA methylated at position 425. Samples were tested in triplicates. Templates #11, #62 and #01 were used as controls.

The qPCR was set up as reported in Example 5 by combining 5 μl template with 15 μl PCR master mix. The PCR conditions were as reported in Example 5. The primer annealing temperature was 58° C.

Methylation Specific qPCR with Bisulfite Treated Genomic DNA

Genomic DNA was extracted from CHO cell lines K18.1, G25-10, G25-17, G42-5 and 43-16 A10, cleaved with the enzyme DraI and deaminated by bisulfite treatment. Two microliters deaminated DNA diluted in 3 μl water was used as template in real-time qPCR applying primer pair 239/237 for amplification of total CMV promoter/enhancer strand A and primer pair 239/267 for amplification of CMV promoter/enhancer strand A methylated at position 425. Samples were tested in triplicates. Templates #11 and #62 were used as controls.

The PCR was set up and qPCR was performed as reported in Example 5. The primer annealing temperature was 58° C.

For a) and b) the fraction of promoter DNA methylated at position 425 was calculated as follows:

$$mC = 1.7^{Cp(t)-Cp(m)} * 100 \qquad \text{(Formula 7)}$$

with
  mC [%]: fraction of DNA methylated at position 425,
  Cp(t): Cp value obtained with universal primer pair 239/237,
  Cp(m): Cp value obtained with methylation-specific primer pair 239/267.

Figure 8:
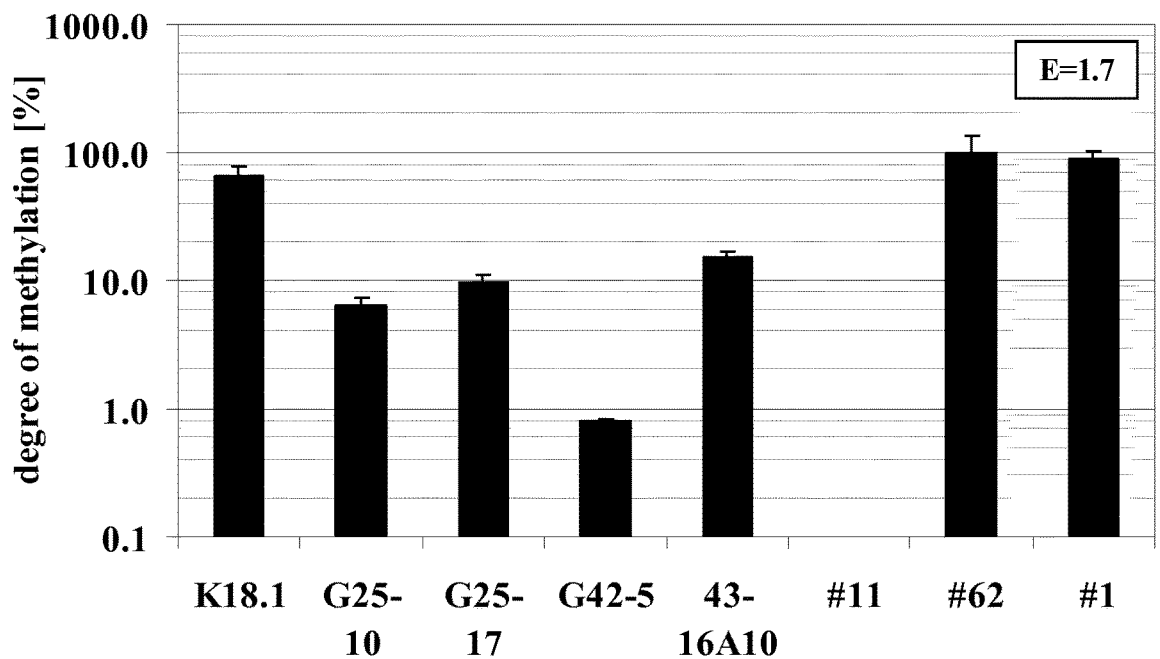
FIG. 8 hCMV-MIE promoter/enhancer nucleic acid methylation at methylation site 425 obtained with primer #239 and #267 with pre-amplification (A) and directly from bisulfite treated genomic DNA (B).
Figure 8:
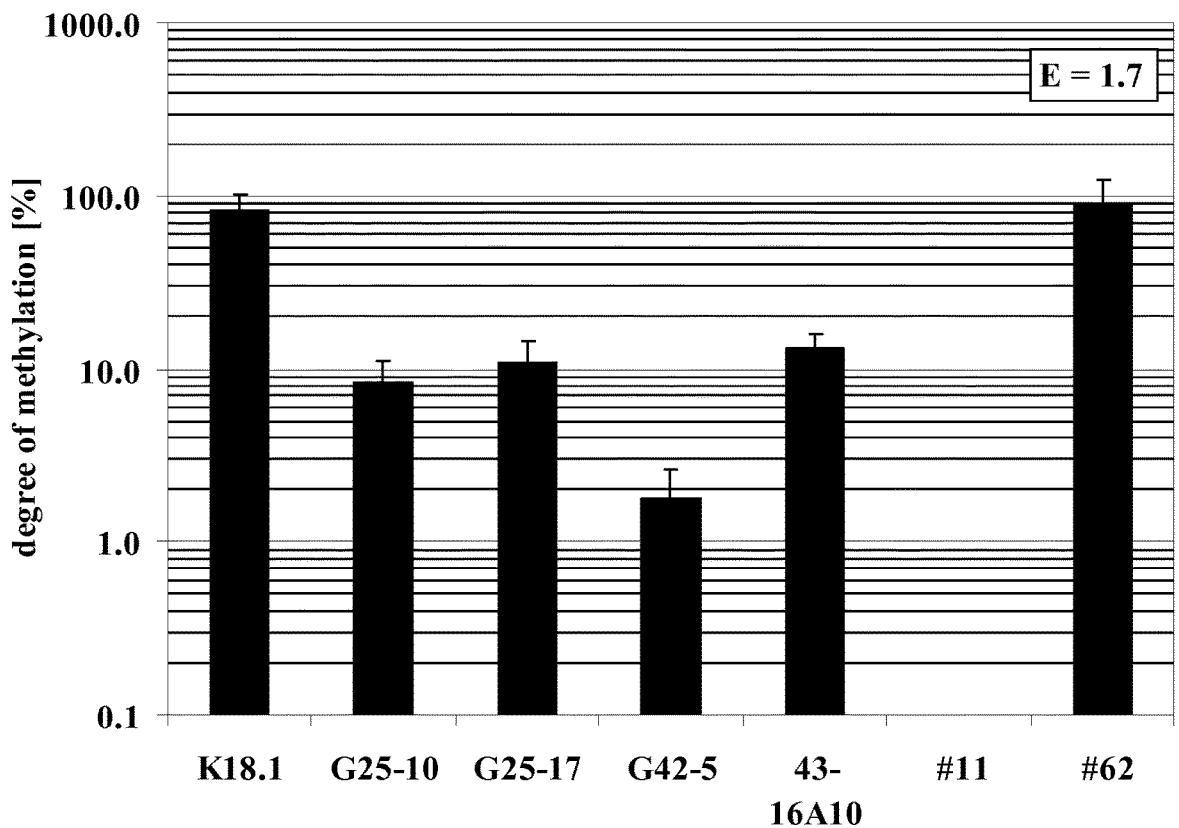

Both assay set-ups provided comparable results. The standard deviation within triplicates was higher without pre-amplification of the CMV promoter strand A (FIGS. 8A and 8B). Methylation of position 425 of the CMV promoter nucleic acid in cell lines K18.1, G25-10, G25-17 and 43-16 A10 was higher than the background of incomplete deamination, which had been found to be approximately 1%. Methylation in cell line G42-5 was below or maximum at background level. For cell line K18.1 the highest methylation was determined (more than 60%).

Assay setting a) was performed with other universal and methylation specific primer pairs. For the calculation of the fraction of DNA methylated at position 425, the amplification efficiency for all primer pairs was assumed to be 2:

$$mC = 2^{Cp(t)-Cp(m)} * 100 \qquad \text{(Formula 5')}$$

with
  mC [%]: fraction of DNA methylated at position 425,
  Cp(t): Cp value obtained with universal primer pair,
  Cp(m): Cp value obtained with methylation specific primer pair.

Table 35 shows a summary of primer pair combinations that have been tested on either cloned DNA templates or on genomic DNA with or without pre-amplification of CMV promoter DNA.

TABLE 35

Primer pair combinations.

| Combination | universal | position 425 specific |
|---|---|---|
| 1 | 239 + 237 | 239 + 266 |
| 2 | 263 + 237 | 263 + 266 |
| 3 | 264 + 237 | 264 + 266 |
| 4 | 239 + 237 | 239 + 267 |
| 5 | 263 + 237 | 263 + 267 |
| 6 | 264 + 237 | 266 + 267 |

EXAMPLE 8

Methylation of Human CMV Major-Immediate-Early Promoter/Enhancer and Prediction of Production Instability of Recombinant CHO Cell Line CHO-K1 cells were transfected with a plasmid coding for a human IgG4 antibody and stable clones were selected using the DHFR/MTX system. High producing parental clones were subcloned by limiting dilution. MTX was kept in the growth medium during the complete cell line generation process. 16 subclones from 10 parental clones were selected.

Selected cells were re-cultivated with 250 nM MTX. As soon as they showed stable growth, they were tested for long term production stability over 60 to 80 generations in the presence and in the absence of MTX. The relative alteration of the SPR over 60 generations was calculated. Methylation of C435 was determined at the beginning of the study with cells grown with MTX and at the end of the study from cells that had been cultivated without MTX.

C425 methylation at start of the study was plotted against the relative alteration of the SPR in the presence (FIG. 11A) and in the absence of MTX (FIG. 11B). The majority of clones with less than 5% methylation at C425 can be found in the fraction of stable clones (less than 40% decrease of SPR with or without MTX), whereas the majority of clones with more than 5% methylation at C425 clustered in the fraction of instable clones. This was independent of weather methylation was correlated with stability in the presence or in the absence of MTX (see also Table 36. Most of the stable clones, that lose less than 20% productivity with MTX and less than 30% productivity without MTX, exhibit less than 5% C425 methylation.

TABLE 36

Correlation of methylation with stability in the presence or in the absence of MTX (A) and plasmid copy number (B).

| A-16 clones | number of clones with methylation at C425 at start less than 5% | number of clones with methylation at C425 at start more than 5% |
|---|---|---|
| $SPR_{rel}\_End \geq 60\%$ (cultivation in the presence of MTX) | 8 | 3 |
| $SPR_{rel}\_End < 60\%$ (cultivation in the presence of MTX) | 1 | 4 |
| $SPR_{rel}\_End \geq 60\%$ (cultivation in the absence of MTX) | 6 | 2 |
| $SPR_{rel}\_End < 60\%$ (cultivation in the absence of MTX) | 3 | 5 |

| B-16 clones | plasmid copy number less than 10 | plasmid copy number equal to or more than 10 |
|---|---|---|
| $SPR_{rel}\_End \geq 60\%$ (cultivation in the presence of MTX) | 7 | 4 |
| $SPR_{rel}\_End < 60\%$ (cultivation in the presence of MTX) | 0 | 5 |
| $SPR_{rel}\_End \geq 60\%$ (cultivation in the absence of MTX) | 6 | 2 |
| $SPR_{rel}\_End < 60\%$ (cultivation in the absence of MTX) | 1 | 7 |

This finding shows that the determination of C425 methylation can be used as a predictive marker to determine the stability of polypeptide expression in generated cell clones and thereby allowing the selection of stable clones with stable productivity during cell line development. It has been found that C425 methylation of 5% or less is a suitable criterion for the selection of stable cell clones.

It has further been found that two intermediately stable cell clones as well as two very instable clones that were non-methylated at the beginning of the study rise above 5% in methylation during stability testing without MTX (see also FIG. 12). This shows that the fraction of cell clones that are falsely predicted as stable (false negative cell clones) can be reduced by cultivating them for some time in the absence of MTX before testing.

Figure 4:
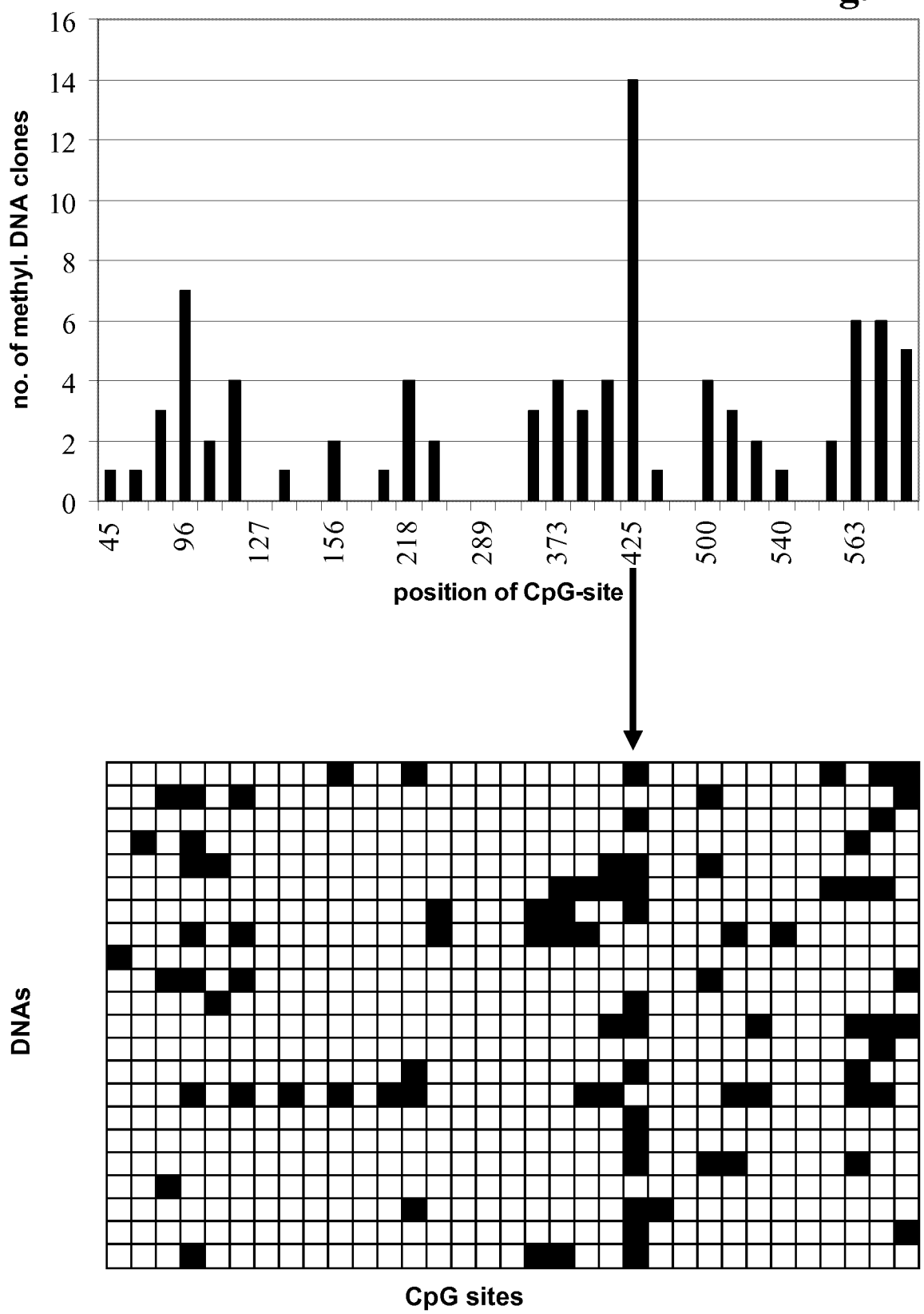
FIG. 4 Upper figure: frequency of methylation within hCMV-MIE DNA promoter/enhancer from recombinant CHO cell lines at different methylation sites determined by the analysis of 19-22 individual promoter nucleic acids; lower figure: schematic representation of methylated CpG sites within hCMV-MIE promoter/enhancer DNA from recombinant CHO cell lines—methylated sites are shown in black—position 425 is highlighted by an arrow.
    A: cell line K18.1-methylation of all CpG sites: 12%, methylation of site C425: 64%, methylation of site C591: 27%, methylation of site C96: 32%;
    B: cell line G25-10—methylation of all CpG sites: 0.5%, methylation of site C425: 0%, methylation of site C591: 5%, methylation of site C96: 0%;
    C: cell line G25-17—methylation of all CpG sites: 0.3%, methylation of site C425: 0%, methylation of site C591: 0%, methylation of site C96: 0%;
    D: cell line G42-5—methylation of all CpG sites: 0.6%, methylation of site C425: 0%, methylation of site C591: 0%, methylation of site C96: 0%;
    E: cell line 43-16 A10—methylation of all CpG sites: 4.4%, methylation of site C425: 25%, methylation of site C591: 15%, methylation of site C96: 10%.
Figure 4:
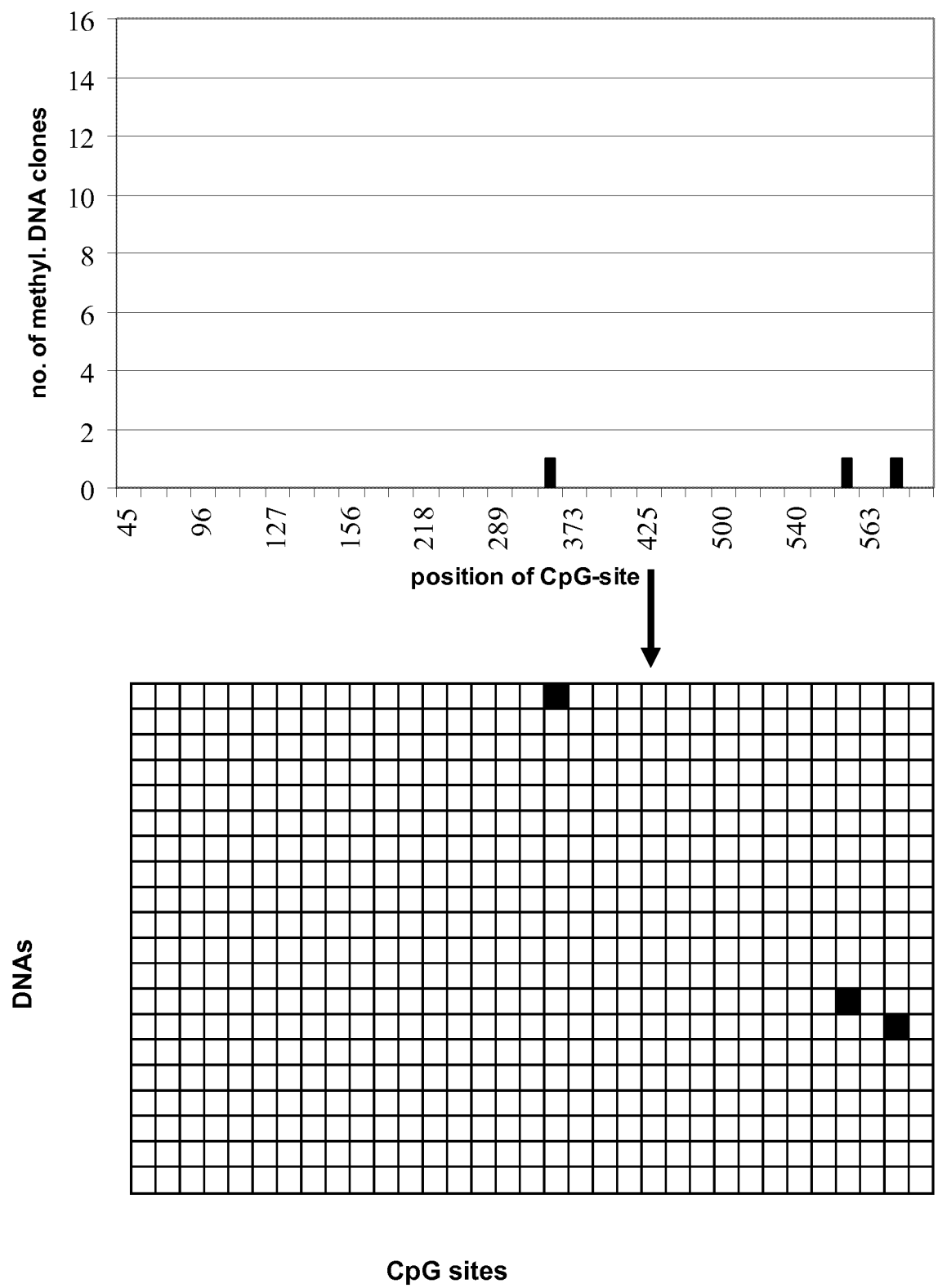
Figure 4:
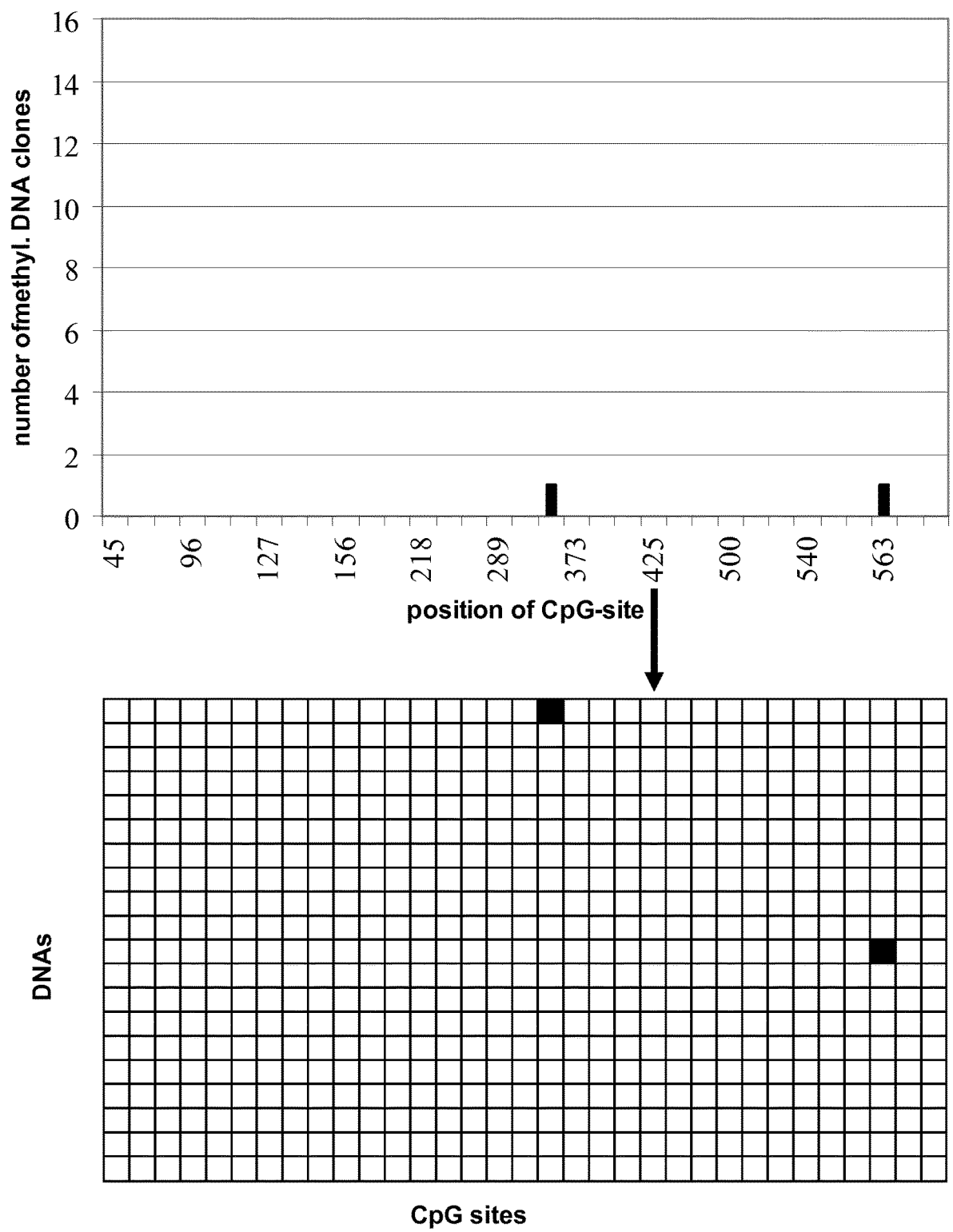
Figure 4:
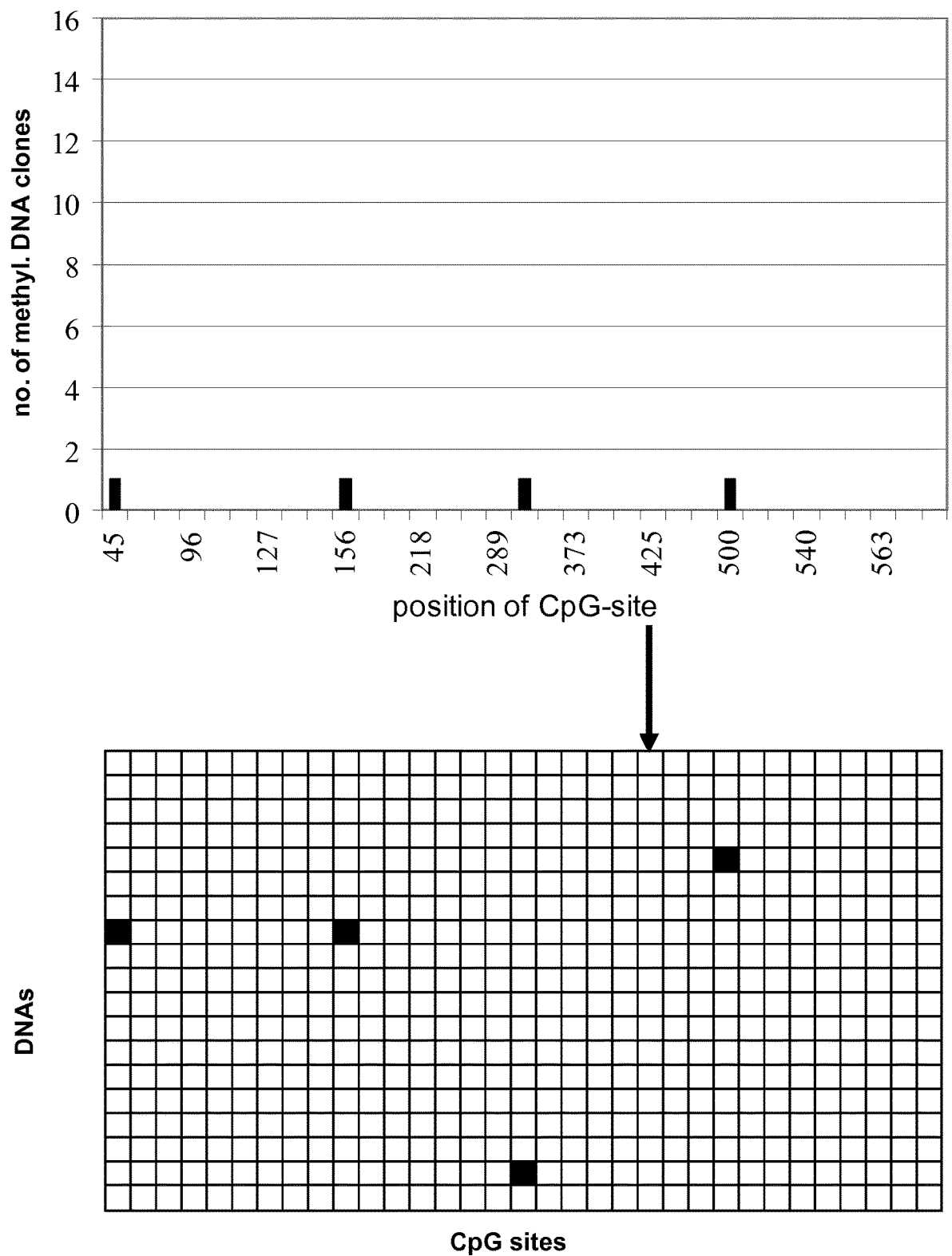
Figure 4:
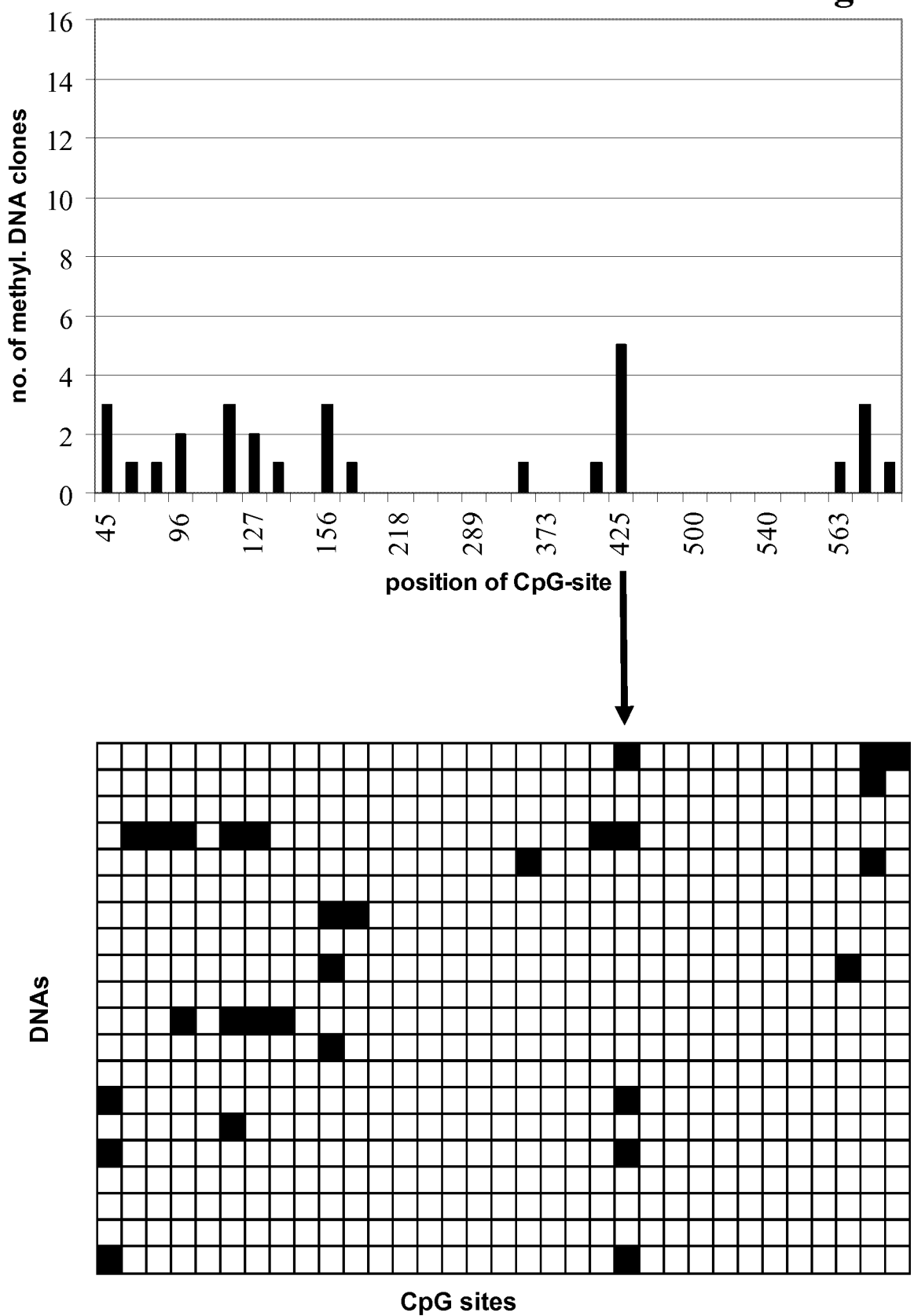

In order to confirm C425 methylation by a second method, we performed bisulfite sequencing with highly methylated clone 44-28 (FIG. 13). The degree of methylation at C425 was found to be 80%. This was consistent with the result of methylation specific PCR, considering the variation of both assays. As with clones K18.1 and 43-16 Al 0 (FIG. 4), C425 was most often methylated among all CpG sites within the human CMV major-immediate-early promoter/enhancer DNA. Other methylation events clustered at the 5' end and the 3' end. The average degree of methylation at all sites was 18%.

EXAMPLE 9

Early Methylation Coincides with High Transgene Copy Numbers

The integrated copies of immunoglobulin light and heavy chain genes at the beginning and at the end of stability testing were determined using a multiplex qPCR assay based on the TaqMan principle. Two primer sets consisting of a forward primer, a reverse primer and a hydrolysis probe were used: the one being specific for the human kappa chain gene, the other being specific for human gamma heavy chain genes. To allow determination of absolute copy numbers, the linearized expression plasmid, which had been used for transfection, was used as a standard. Equal amplification efficiency of samples and standard were assured.

For qPCR, the LightCycler® 480 II system was employed (Roche Diagnostics GmbH, Mannheim, Germany) and samples were prepared using the LightCycler® 480 Probes Master (Roche Diagnostics GmbH, Mannheim, Germany).

5 µl template solution containing 50 ng genomic DNA was combined with 15 µl PCR master mix in the well of a 96-well microtiter plate. In case of the standard, the template solution contained $2.5 \times 10^7$, $2.5 \times 10^6$, $2.5 \times 10^5$, $2.5 \times 10^4$ and $2.5 \times 10^3$ copies of the corresponding linearized plasmid DNA.

15 µl PCR master mix comprised:
10 µl LightCycler® 480 Probes Master
1 µl forward primer #133 (10 pmol/µl)
1 µl reverse primer #132 (10 pmol/µl)
0.5 µl probe #166 (10 pmol/µl)
1 µl forward primer #178 (10 pmol/µl)
1 µl reverse primer #180 (10 pmol/µl)
0.5 µl probe #185 (10 pmol/µl)

The plate was sealed with a LightCycler® 480 sealing foil (Roche Diagnostics GmbH, Mannheim, Germany) and centrifuged at 1,500 g for 2 minutes. Afterwards the plate was mounted into the LightCycler® 480 system and subjected to qPCR. Each sample was tested in triplicate, standards were run in quadruplicate.

The collection and analysis of the data was performed using the LightCycler® 480 software version 1.5. Basically, mean Cp values of the plasmid standard dilutions were plotted against the respective gene copy numbers to generate a standard curve from which the number of transgenes in the sample was extrapolated.

The number transgenes per cell was calculated assuming that the average DNA content per cell is jpg:

$$N_c = N_s/50000*6$$

$N_c$: number of transgene copies per cell
$N_s$: number of transgene copies in the sample

TABLE 38

| Primer no. | Primer sequences (5' -> 3') | SEQ ID NO: |
|---|---|---|
| 133 | TCACAGAGCAGGACAGCAAG | 26 |
| 132 | GACTTCGCAGGCGTAGACTT | 27 |
| 166 | (FAM)-AGCACCTACAGCCTCAGCAGCACC-(BHQ1) | 28 |
| 178 | CGAACCGGTGACGGTGT | 29 |
| 180 | GAGGGCACGGTCACCAC | 30 |
| 185 | (Cy5)-CACACCTTCCCGGCTGTCCTACAG-(BHQ3) | 31 |

FIG. 14 depicts the light chain gene copy numbers of methylated and non-methylated cells before and after stability testing. Not surprisingly, identical copy numbers were found the heavy chain gene because the cells had been transfected with a double gene vector carrying both genes (data not shown). Early methylation i.e. methylation before stability testing was exclusively found with cells carrying more than 10 transgene copies whereas some clones with less than 10 transgene copies acquired methylation during stability testing. As a consequence, selecting clones with low transgene copy numbers before stability testing equally enriches clones with stable productivity (Table 39).

TABLE 39

Correlation of transgene copies with stability in the presence or in the absence of MTX.

| 16 clones | Plasmid copies < 10 | Plasmid copies ≥ 10 |
|---|---|---|
| $qP_{rel}$_End + MTX ≥ 60% | 7 | 4 |
| $qP_{rel}$_End + MTX < 60% | 0 | 5 |
| $qP_{rel}$_End − MTX ≥ 60% | 6 | 2 |
| $qP_{rel}$_End − MTX < 60% | 1 | 7 |

TABLE 37

PCR conditions were as follows:

| step | | No. of cycles | T [° C.] | t [min:s] | ramp rate [° C. s−1] | acquisition |
|---|---|---|---|---|---|---|
| denaturation | | 1 | 95 | 10:00 | 4.40 | — |
| real-Time PCR | denaturation | 45 | 95 | 00:10 | 4.40 | — |
| | annealing | | 60 | 00:05 | 2.20 | — |
| | elongation | | 72 | 00:01 | 4.40 | single |
| cooling | | 1 | 37 | 01:00 | 2.2 | |

We further observed that production instability was not generally associated with a loss of transgene copies. Clones 1A5-05, 1A5-21, 1A5-24 and 2B1-02 lost transgene copies, 2B-13 was stable and 14-13 as well as 14-23 increased in gene copies (see also FIG. 11B).

EXAMPLE 10

Identification of Present Histone Modifications Close to Human CMV Major-Immediate-Early Promoter/Enhancer DNA by Chromatin Immunoprecipitation and Real-Time PCR Chromatin Immunoprecipitation of CHO Cell Lines The human CMV major-immediate-early promoter/enhancer fragment (SEQ ID NO: 01) used for the expression of antibody light and heavy chain is close to DNA compacting histones (chromatin) in stable producer cell lines. An accumulation of modified histones close to the human CMV major-immediate-early promoter/enhancer fragment will be measured with the chromatin immunoprecipitation assay (ChIP).

Thirty-two CHO cell lines (samples H-1 to H-20 and T-1 to T-12, see Table 11) were fixed in 3.7% formaldehyde for 10 min. at room temperature. Fixation was stopped in 10% glycine for 5 min. Cells were lysed for 10 min. on ice in Cell Lysis Buffer, centrifuged with 5,000 rpm, 4 min. at 4° C. Pellets were resuspended in Nuclei Lysis Buffer and chromatin was sonicated to an average fragment size of 200-500 bp with Branson Sonifier B15. Concentrations of chromatin fragments were determined with Pierce® BCA Protein Assay Kit (Thermo Scientific, Rockford, USA). 2.5 µg-100 µg chromatin fragments were added to 1.5 volumes IP Dilution Buffer containing 3 µl-12 µl antibody and incubated overnight at 4° C. while rotating with 25 rpm.

Protein A Agarose beads (Roche Diagnostics GmbH, Mannheim, Germany) were blocked in IP Dilution Buffer with 100 µg/ml salmon sperm DNA (Invitrogen, Carlsbad, U.S.A) and 5 mg/ml BSA (Bovine Serum Albumin, Roche Diagnostics GmbH, Mannheim, Germany) overnight at 4° C. Antibody-chromatin precipitates were purified by incubation in blocked Agarose beads for 1 hour, followed by incubation for 5 min at 4° C. in 2× Low, 1× High salt, 1× LiCl and 1× TE wash buffer each. Antibodies were eluted from the Agarose beads with 200 µl IP Elution buffer, for 30 min. at 65° C. 0.5 µl RNAse DNAse free (Roche Diagnostics GmbH, Mannheim, Germany) were added to digest RNA at 37° C. for 30 minutes. For protein digestion NaCl (final concentration 0.2 M) and Proteinase K (final concentration 100-200 µg/ml) (Roche Diagnostics GmbH, Mannheim, Germany) were added and solution was incubated for 1.5 hours at 65° C. DNA was recovered with Roche PCR Purification Kit in 150 µl PCR grade $H_2O$ (Roche Diagnostics GmbH, Mannheim, Germany).

TABLE 40

Buffer for Chromatin Immunoprecipitation (ChIP).

| CHIP Cell lysis buffer | LiCl wash buffer |
|---|---|
| 20 mM Tris-HCl | 0.25M LiCl (Villagra et at. |
| pH 8.0 | CHIP) |
| 85 mM KCl | 1% NP40 |
| 0.5% NP40 (octylphenol- | 1% deoxycholate |
| polyethoxyethanol) | (deoxycholic acid) |
| double distilled water | 1 mM EDTA |
| Nuclei Lysis buffer | 20 mM Tris, pH 8.0 |
| 50 mM Tris-HCl pH 8.0 | double distilled water |
| 10 mM EDTA pH 8.0 | TE buffer |
| 1% SDS | 10 mM Tris-HCl pH8.0 |
| double distilled water | 1 mM EDTA |
| 1 tablet Roche Complete | (IP) Elution |
| per 10 ml | buffer |
| Low salt wash buffer | 50 mM NaHCO3 |
| 0.1% SDS | 1% SDS |
| 1% Triton X 100 | double distilled water |
| 2 mM EDTA | IP Dilution buffer |
| 20 mM Tris-CL pH 8.0 | 1.1% Triton X 100 |
| 150 mM NaCl | 1.2 mM EDTA |
| double distilled water | 16.7 mM Tris-HCl pH 8.1 |
| High salt wash buffer | (8.0) |
| 0.1% SDS | |
| 1% Triton X 100 | |
| 2 mM EDTA | |
| 20 mM Tris-CL pH 8.0 | |
| 500 mM NaCl | |
| 167 mM NaCl | |
| H2O | |

TABLE 41

Antibodies specific for histone or histone modifications.

| Target | name | company | ChIP grade | host | cat.no. lot |
|---|---|---|---|---|---|
| H3K4me3 | ChIPAb + Trimethyl-histone H3 (Lys4) | Millipore | v | rabbit monoclonal | 17-614 ng1848343 |
| H3K27me3 | ChIPAb + Trimethyl-histone H3 (Lys27) | Millipore | v | rabbit polyclonal | 17-622 dam1850974 |
| H3K9me3 | Anti-histone H3 (tri methyl K9) antibody | Abcam | v | rabbit polyclonal | ab8898 gr58934-1 |
| H3 | Anti-histone H3 antibody | Abcam | v | rabbit polyclonal | ab1791 GR103799 |
| H3ac | Anti-acetyl-histone H3 | Millipore | v | rabbit polyclonal | 06-599 2068182 |
| H3K4me3 | histone H3K4me3 antibody (pAb) | activemotif | √ | rabbit Polyclonal | 39915 14013006 |
| H3ac | Anti-acetyl-histone H3 Antibody | Millipore | √ | rabbit polyclonal | 06-599 2153150 |
| H3K9me3 | ChIPAb + Trimethyl-histone H3 (Lys9) | Millipore | v | polyclonal | 17-625 2190636 |
| H3K27me3 | ChIPAb + Trimethyl-histone H3 (Lys27) | Millipore | v | rabbit Polyclonal | 17-622 2034145 |
| H3 | Anti-histone H3 antibody | Abcam | √ | Rabbit polyclonal | ab1791 GR135321 |

Quantitative Real Time PCR of ChIP DNA

Real time quantitative PCR was used to detect an accumulation of specific histone modifications on the human CMV major-immediate-early promoter/enhancer fragment (SEQ ID NO: 01) in CHO cell lines by measuring the relative amount of the human CMV major-immediate-early promoter/enhancer fragment per chromatin immunoprecipitation.

Genomic DNA from untreated Input Sample (IS) and antibody purified chromatin fragments were amplified with real time quantitative PCR using LightCycler 480 SYBR Green I Master (Roche Diagnostics GmbH, Mannheim, Germany) using the LightCycler 480 II system (Roche Diagnostics GmbH, Mannheim, Germany). To quantify the amount of human CMV major-immediate-early promoter/enhancer fragment (SEQ ID NO: 01) specific primer for possible reference genes and for the human CMV major-immediate-early promoter/enhancer fragment were used.

TABLE 42

Primer sequences for real time quantitative PCR.

| SEQ ID NO: | Primer NO: | Target | Sequence |
| --- | --- | --- | --- |
| 32 | 396 | hCMV-MIE forward 1 | TACATCAATGGGCGTGGATA |
| 33 | 397 | hCMV-MIE reverse 1 | AAGTCCCGTTGATTTTGGTG |
| 34 | 386 | Gusb forward 1 | CAGGGTGGGATGCTCTTC |
| 35 | 387 | Gusb reverse 1 | GCCGGTTTTCCGAGAAGT |
| 36 | 431 | Eif3i forward 1 | GTTCCCGGCACTGACACT |
| 37 | 432 | Eif3i reverse 2 | ACTTGATCTGCGTGATGGAC |
| 38 | 484 | Fox2a forward 1 | ATCACCCGTACTGCTGCTCT |
| 39 | 485 | Fox2a reverse | GAGGCTTCTGGGGATCTCTT |
| 40 | 468 | Gata5 forward 1 | CACCTACCCCATCCTGTCTG |
| 41 | 469 | Gata5 reverse 1 | GAGGAGGTGAAGGCAAAGTCT |
| 42 | 388 | Rho forward 1 | AGCCTCGGTCTCTATTGACG |
| 43 | 389 | Rho reverse 1 | CGTTGGAGAAGGGCACATAA |

2.5 µl eluted DNA fragments, 1 µl (10 pmol/µl) of forward primer 396 (SEQ ID NO: 32) and 1 µl (10 pmol/µl) of reverse primer 397 (SEQ ID NO: 33) for the human CMV major-immediate-early promoter/enhancer fragment (SEQ ID NO: 01), 5 µl LightCycler 480 SYBR Green I Master and nuclease free water were mixed up to a total volume of 10 µl. Reference genes were quantified on the same plate. The mix was applied to 384 well plate (Roche Diagnostics GmbH, Mannheim, Germany).

The plate was sealed with a LightCycler® 480 sealing foil (Roche Diagnostics GmbH, Mannheim, Germany) and centrifuged at 1,200 g for 3 minutes. Afterwards the plate was mounted into the LightCycler® 480 system and subjected to real time qPCR. Each sample was tested in triplicate.

TABLE 43

PCR conditions were as follows:

| step | | No. of cycles | T [° C.] | t [min:s] | ramp rate [° C. s-1] | acquisition |
| --- | --- | --- | --- | --- | --- | --- |
| denaturation | | 1 | 95 | 15:00 | 4.40 | — |
| real-time PCR | denaturation | 45 | 95 | 00:15 | 4.40 | — |
| | annealing | | 60 | 00:10 | 2.20 | single |
| | elongation | | 72 | 00:15 | 4.40 | — |
| melting curve | denaturation | 1 | 95 | 00:05 | 4.40 | — |
| | annealing | | 60 | 01:00 | 2.20 | — |
| | melting | | 90 | 00:00 | 0.11 | continuous |
| cooling | | 1 | 40 | 00:30 | 2.2 | |

The collection and analysis of the data was done with the LightCycler® 480 software version 1.5.

EXAMPLE 11

Relative Quantification of Human CMV Major-Immediate-Early Promoter/Enhancer Fragment on Histone Modifications in Real-Time PCR
Stability of Reference Genes In this example the stability of potential reference genes for specific histone modifications was calculated with the program "Normfinder". The model and statistical framework underlying "NormFinder" are described in Andersen, C. L., et al. Cancer Res. 64 (2004) 5245-5250.

The "NormFinder add on" for excel provides the stability value for each gene, which is a direct measure for the estimated expression variation. The gene with the smallest stability value is the most stable gene. The input data is supposed to be on a linear scale, thus the Percent Input Method was used to linearize scale expression quantities using the following formula:

$$\% \text{ of InputSample} = 100 * 2^{\Delta Cq(InputSample - ChIPSample)} \quad \text{(Formula 9)}$$

Five genes (see Table 44) were tested with "Normfinder". Twenty samples (H-1 to H20) in three biological replicates were investigated for the stability of the histone 3 acetylation, histone 3 lysine 4 three-fold methylation and histone 3 close to the human CMV major-immediate-early promoter/enhancer fragment and the reference genes.

TABLE 44

Stability values of possible reference genes and the human CMV major-immediate-early promoter/enhancer fragment.

| H3ac % of input sample | | H3% of input sample | | H3K4me3% of Input Sample | |
|---|---|---|---|---|---|
| Gene name | Stability value | Gene name | Stability value | Gene name | Stability value |
| hCMV-MIE | 10.729 | hCMV-MIE | 0.571 | hCMV-MIE | 5.399 |
| Eif3i | 0.160 | Eif3i | 0.138 | Eif3i | 1.792 |
| Fox2a | 0.491 | Fox2a | 0.181 | Fox2a | 1.711 |
| Gata5 | 0.481 | Gata5 | 0.141 | Gusb | 1.680 |
| Gusb | 0.093 | Gusb | 0.136 | | |

Reference gene Gusb is more stable in chosen ChIP conditions than the other controls. Gusb was used as reference gene for the normalization of histone 3 acetylation, histone 3 lysine 4 three-fold methylation and histone 3 levels.
Estimation of Amplification Efficiency of Primer Pairs with LinRegPCR Software In this example the amplification efficiency of the primer pair 396/397 for the human CMV major-immediate-early promoter/enhancer fragment and of the primer pair 386/387 for reference gene Gusb were estimated with the Lin-RegPCR software (www.hartfaalcentrum.nl) for samples H-1 to H20. The program determines baseline fluorescence and does a baseline subtraction. Then a Window-of-Linearity is set and PCR efficiencies per sample are calculated (see Ramakers, et al., NeuroSci Lett. 2003; Ruijter et al., Nucleic Acids Research 2009).

$$Eff = 10^{slope}$$

$$Eff = 10^{slope} \quad \text{(Formula 11)}$$

The individual PCR efficiency (Eff) is deduced from the slope of the linear regression line and is defined a fold increase per cycle. It can range between 1 and 2. An efficiency of 2 represents a perfect doubling of the amplicon in each cycle.

TABLE 45

Amplification efficiency of reference Gusb primer pair and target hCMV-MIE primer pair.
Amplification efficiency:

| Primer pair | Mean efficiency | Stdev. |
|---|---|---|
| hCMV MIE 396/7 | 1.911 | 0.0068 |
| Gusb 386/7 | 1.930 | 0.0068 |

Primer pairs 396/397 and 386/387 yielded stable and comparable amplification efficiencies with 20 samples and 3 biological replicates irrespective of whether ChIP input samples were measured or DNA precipitated with antibodies against histone 3, acetylated histone 3 or histone 3 lysine 4 three-fold methylation. Primer pairs 396/397 and 386/387 were used for the relative quantification of histone 3 acetylation, histone 3 lysine 4 three-fold methylation and histone 3 levels close to human CMV major-immediate-early promoter/enhancer fragment relative to histone 3 and histone 3 modification levels close to reference gene Gusb.
Delta Delta Cq Method for Relative Quantification of Histone Modification Relative to the Level of Histone The relative quantification of histone 3 acetylation, histone 3 lysine 4 three-fold methylation and histone 3 levels close to human CMV major-immediate-early promoter/enhancer fragment were estimated with the Livak method, also known as delta delta Cq ($\Delta\Delta Cq$) method.

The method can be used for relative quantification of a target regarding to a reference. In this example the relative quantification of histone 3 acetylation, histone 3 lysine 4 three-fold methylation and histone 3 levels close to human CMV major-immediate-early promoter/enhancer fragment were normalized to the histone 3 modification and the histone 3 levels close to reference gene Gusb in two steps.
First delta Cq was calculated as follows:

$$\Delta Cq = \text{inputsample} - \text{sample} \quad \text{(formula 12)}$$

Delta Cq ($\Delta Cq$) is the difference between quantification cycles (Cq) of untreated (input sample) and treated (ChIP sample) condition of the same sample, amplified with the same primer pair. The delta Cq is used to depict a value relative to the untreated condition within the same sample. To compare different samples, the delta delta Cq method was used.

$$\Delta\Delta Cq \rightarrow \text{ratio} = \frac{2^{\Delta Cq_{target}(control - sample)}}{2^{\Delta Cq_{ref}(control - sample)}} \quad \text{(Formula 13)}$$

-continued $$\Delta\Delta Cq \rightarrow \text{ratio} = \frac{2^{\Delta Cq_{target}(control-sample)}}{2^{\Delta Cq_{ref}(control-sample)}}$$

In this example delta delta Cq is the difference between delta Cq of the target hCMV MIE and delta Cq of the reference Gusb for all samples H-1 to H-20. Relative amounts of DNA determined using delta delta Cq values can be compared between samples.

Finally levels of histone 3 acetylation and histone 3 lysine 4 three-fold methylation were normalized to the level of histone 3 for the 20 CHO cell lines H-1 to H-20 in three biological replicates. The results with the standard deviation are displayed in FIGS. 15 and 16.

EXAMPLE 12

Histone 3 Acetylation and Histone 3 Lysine 4 Three-Fold Methylation Close to Human CMV Major-Immediate-Early Promoter/Enhancer Fragment as Well as Methylation of C425 of Human CMV Major-Immediate-Early Promoter/Enhancer Fragment Correlate with Long-Term Stability The relative acetylation and the lysine 4 threefold methylation levels relative to the level of histone 3 (H3ac/H3 & H3K4me3/H3) close to human CMV major-immediate-early promoter/enhancer fragment as well as the percentage of methylation of C425 of human CMV major-immediate-early promoter/enhancer fragment (mC-425[%]) were investigated in a fit model with the personality "Standard least squares" and the emphasis "effect leverage model" to detect effects influencing the long term stability of the producer cell lines H-1 to H-20. For calculation the JMP software version 10 (SAS, Boeblingen, Germany) was used.

The histone modification values and the percentage of C-425 methylation of samples H-1 to H-20 were fed as an effect into the model individually. The percentual alteration of specific production rate (delta SPR) after 60 generations was fed as response. Resulting leverage plots are displayed in FIGS. 17 to 19. The number of parameters associated with the effect (Nparm) and the degrees of freedom are 1.

RSquare (RSq) estimates the proportion of variation in the response that can be attributed to the model rather than to random error. An $R^2$ closer to 1 indicates a better fit. An $R^2$ closer to 0 indicates that the fit predicts the response no better than the overall response mean. Root Mean Square Error (RMSE) estimates the standard deviation of the random error. It is the square root of the Mean Square of Error in the Analysis of Variance report. Prob>F lists the p-value for the Effect test, which informs about the significance of an effect.

TABLE 46

P-values of fed effects H3K4me3/H3 and H3ac/H3 calculated in effect test. Calculated in three biological replicates for samples H. Prob > F lists the p-value for the Effect test

| | Selection condition | |
|---|---|---|
| Effect | With MSX | Without MSX |
| H3K4me3/H3 | 0.0102 * | 0.889 |
| H3ac/H3 | <0.0001 * | 0.1449 |
| mC-425 [%] | 0.0898 | 0.0041 * |

* values of 0.05 or less were considered evidence of significant effect in the model.

Table 46 shows the significance of mC-425[%] under (−) MTX conditions. The effect of H3ac/H3 and H3K4-me3/H3 are significant under (+) MSX condition.

Actual delta SPR values were plotted against predicted values in leverage plots, regarding to the effect and the selection condition over 60 generations (FIG. 17-19). This Actual by Predicted plot shows how well the model fits the data. The lowest p-values were detected for the H3ac/H3 effect with selection agent (FIG. 18) followed by mC 425[%] effect without selection agent (FIG. 19).

Outlier Analysis Comparing Conditions with and without Selection Agent MSX for Delta SPR Values of Samples H-1 to H-20

The leverage plots of the condition without selection agent ((−) MSX) have remarkably aberrant values for delta SPR in sample H-18. Therefor an outlier analysis showing Jackknife Distances was done (FIG. 20).

This verifies that the increase of delta SPR in sample H-18 under the condition (−) MSX is abnormal compared to all other samples. Therefore leverage analyses were repeated without sample H-18. The calculated p-values of the effect test for 19 samples H-1 to H-17 and H-19 to H-20 are displayed in Table 47.

TABLE 47

P-values of fed effects H3K4me3/H3 and H3ac/H3 calculated in effect test. P-values calculated of 19 samples (H-1 to H-17, H-19, H-20) in three biological replicates. Prob > F lists the p-value for the Effect test

| | Selection condition | |
|---|---|---|
| Effect | With MSX | Without MSX |
| H3K4me3/H3 | 0.0136 * | 0.3464 |
| H3ac/H3 | <0.0001 * | 0.0001 * |
| mC-435 [%] | 0.1171 | 0.0908 |

* Values of 0.05 or less were considered evidence of significant effect in the model.

Table 47 shows high significance of H3ac/H3 in both selection conditions. The effect of H3K4-me3/H3 is significant in condition (+) MSX.

Actual delta SPR values were plotted against predicted values in leverage plots, regarding the effect and the selection condition over 60 generations (FIG. 20-22). The Actual by Predicted plots show how well the model fits the data. The best fit was observed for the H3ac/H3 effect (FIG. 21).

EXAMPLE 13

Prediction of production instability in recombinant CHO cell lines by using histone modifications close to human CMV major-immediate-early promoter/enhancer and methylation of C425 of human CMV major-immediate-early promoter/enhancer fragment as marker.

Increased Mean Delta SPR of Project H Samples by Rejecting Bad Producer Cell Lines with Filter Settings As reported in Example 12, values of outlier sample H-18 were excluded from further investigations of establishing prediction marker.

Levels of histone 3 acetylation relative to the level of histone 3 close to human CMV major-immediate-early promoter/enhancer fragment and percentage of C-425 methylation of human CMV major-immediate-early promoter/enhancer fragment were investigated as prediction markers for production stability with and without selection agent.

As described in Osterlehner et al. filter for mC-425[%] values was set to 5%. Values above 5% were rejected to increase the mean delta SPR of remaining samples.

For H3ac/H3 values of samples H-1 to H-17, H-19 and H-20 a decision tree was calculated with jmp software. Best split node and therefor best filter was calculated with the LogWorth statistic. The LogWorth is calculated as:

$$-\log 10(p\text{-value}) \quad \text{(Formula 14)}$$

where the adjusted p-value is calculated in a complex manner that takes into account the number of different ways splits can occur. This calculation is very fair compared to the unadjusted p-value, which favors X's with many levels, and the Bonferroni p-value, which favors X's with small numbers of levels (white paper: "Monte Carlo Calibration of Distributions of Partition Statistics").

The best split under (+) MSX condition for samples H-1 to H-17, H-19 and H-20 was 0.58 histone 3 acetylation relative to the level of histone 3 (H3ac/H3). To reduce number of false negative samples the filter was set to the lower value of A>0.5 H3ac/H3.

Both filters were used separate and in combination. The means of delta SPR at conditions with or without selection agent MSX were calculated for each positive gate and compared to the unfiltered mean (Table 48).

TABLE 48

Calculated means of delta SPR with and without selection agent and under filter conditions A > 0.5 H3ac/H3 and B < 5% mC-425 [%] PSP. Values were calculated for samples H-1 to H-17, H-19 and H-20 referring to filter settings.

|  | n | Mean ΔSPR (+) MSX | Mean ΔSPR (−) MSX |
| --- | --- | --- | --- |
| unfiltered | 56 | −0.39 | −0.55 |
| A > 0.5 H3ac/H3 | 23 (41%) | −0.15 | −0.38 |
| B < 5% mC-425[%] PSB | 27 (48%) | −0.24 | −0.45 |
| Combined filter (B ∩ A) | 20 (36%) | −0.13 | −0.36 |

Each filter can increase the mean delta SPR compared to the unfiltered condition. The intersection of filter A and B increases the mean delta SPR of filter A>0.5 H3ac/H3. For visualization of altered delta SPR values, histograms of each condition and filter are displayed in FIG. 23.

Established Filter Settings of Project H were Adopted to Project T to Confirm Positive Effects Twelve cell lines (T-1 to T-12) were also analyzed with filter settings as determined above (see Table 49). For visualization of altered delta SPR values, histograms of each condition and filter are displayed in FIG. 25.

TABLE 49

Calculated means of delta SPR with and without selection agent. Values were calculated for 12 samples T-1 to T-12 referring to filter settings.

|  | n | Mean ΔSPR (+) MTX | Mean ΔSPR (−) MTX |
| --- | --- | --- | --- |
| unfiltered | 36 | −0.29 | −0.41 |
| A > 0.5 H3ac/H3 | 7 (19%) | −0.19 | −0.32 |
| B < 5% mC-425[%] PSB | 24 (67%) | −0.28 | −0.43 |
| Combined filter (B ∩ A) | 7 (19%) | −0.19 | −0.32 |

Observed increase of mean delta SPR compared filtered to unfiltered samples under (−) MTX condition.

Using the filter setting of A>0.5 H3ac/H3 results in an increase of mean delta SPR compared to unfiltered data.

This shows that the histone 3 acetylation relative to the level of histone 3 close to human CMV major-immediate-early promoter/enhancer fragment is a valuable prediction marker.

The invention claimed is:

1. A method for the production of a polypeptide comprising the following steps:
   a) selecting a cell clone/cell line from cells that comprise a nucleic acid comprising a structural gene encoding a polypeptide operably linked to a promoter nucleic acid that has the nucleic acid sequence of SEQ ID NO: 01, comprising the following steps:
      (i) determining a ratio of the level of histone 3 acetylation relative to the level of histone 3 close to the promoter nucleic acid, wherein close to the promoter nucleic acid is within several hundred base pairs upstream of the promoter,
      (ii) determining a methylation frequency of the CpG-site at position 425 of SEQ ID NO: 01, and
      (iii) selecting a cell clone/cell line that has the ratio as determined in step (i) of more than 0.5 and that has the methylation frequency as determined in step (ii) of less than 5%,
   b) cultivating the selected cell clone/cell line, wherein the selected cell clone/cell line has a smaller reduction in specific production rate over a period of 60 generations than that of a cell clone/cell line selected only for having methylation frequency of the CpG-site at position 425 of SEQ ID NO: 01 of less than 5%, and
   c) recovering the polypeptide from the cultivation medium and/or the cell clone/cell line and thereby producing the polypeptide.

2. The method according to claim 1 wherein the polypeptide is an antibody light chain and wherein step a) further comprises:
   determining the copy number of stably integrated light chain expression cassettes, and wherein step iii) further comprises:
   selecting the cell clone/cell line to also have a copy number of stably integrated light chain expression cassettes of 10 or less.

3. The method according to claim 1, wherein the determining of the level of histone 3 acetylation relative to the level of histone 3 comprises the following steps:
   1) isolating chromatin from a candidate cell clone/cell line,
   2) treating a first aliquot of the chromatin with a histone 3 acetylation specific antibody to form a first antibody-chromatin precipitate, and treating a second aliquot of the chromatin with a histone 3 specific antibody to form a second_ antibody-chromatin precipitate,
   3) amplifying genomic DNA from a third non-treated aliquot of the chromatin and from the first treated aliquot and from the second treated aliquot with real time quantitative PCR, and
   4) determining with the results obtained in step 2) and in step 3) the level of histone 3 acetylation relative to the level of histone 3.

4. The method according to claim 1, wherein the determining of the methylation frequency comprises the following steps:
   1) isolating DNA from a candidate cell clone/cell line,
   2) performing for the isolated DNA a methylation specific polymerase chain reaction, and
   3) determining with the results obtained in step 2) the methylation frequency.

5. The method according to claim 4, wherein in step 2) a methylation specific primer and a universal primer are used.

6. The method according to claim 5, wherein the universal primers have the sequence of SEQ ID NO:09 and 11 and the methylation specific primers have the sequence of SEQ ID NO:11 and 18.

7. The method according to claim 1, wherein the level of histone 3 acetylation relative to the level of histone 3 is normalized to a reference gene.

8. The method according to claim 7, wherein the reference gene is Gusb.

9. The method according to claim 1, wherein the cell clone/cell line is a CHO cell clone/cell line.

10. The method according to claim 1, wherein the polypeptide is an antibody or an antibody fragment or an antibody conjugate.

11. The method according to claim 10, wherein the antibody is a bispecific antibody.

12. The method according to claim 1, wherein the method comprises prior to step a) the following steps:
   x) providing a mammalian, non-human cell, and
   y) transfecting the provided cell with a nucleic acid, which comprises a structural gene encoding a polypeptide operably linked to a promoter nucleic acid that has the nucleic acid sequence of SEQ ID NO:01.

13. The method according to claim 1, wherein
   in step (i), the ratio is an average of the level of histone 3 acetylation relative to the level of histone 3 close to the promoter nucleic acid, is determined for at least 10 cells obtained from culturing a candidate cell clone/cell line, and
   in step (ii), the methylation frequency is an average methylation frequency of the CpG-site at position 425 of SEQ ID NO: 01, is determined for at least 10 cells obtained from culturing the candidate cell clone/cell line.

14. The method according to claim 1, wherein close to the promoter nucleic acid is within 200 base pairs upstream of the promoter.

15. The method according to claim 14, wherein close to the promoter nucleic acid is within 200 base pairs upstream of a transcription start site of the promoter.

* * * * *

SEQUENCE LISTING

<160> NUMBER OF SEQ ID NOS: 53

<210> SEQ ID NO 1
<211> LENGTH: 603
<212> TYPE: DNA
<213> ORGANISM: Human cytomegalovirus

<400> SEQUENCE: 1

```
atgttgacat tgattattga ctagttatta atagtaatca attacggggt cattagttca      60
tagcccatat atggagttcc gcgttacata acttacggta aatggcccgc ctggctgacc     120
gcccaacgac ccccgcccat tgacgtcaat aatgacgtat gttcccatag taacgccaat     180
agggactttc cattgacgtc aatgggtgga gtatttacgg taaactgccc acttggcagt     240
acatcaagtg tatcatatgc caagtacgcc ccctattgac gtcaatgacg gtaaatggcc     300
cgcctggcat tatgcccagt acatgacctt atgggacttt cctacttggc agtacatcta     360
cgtattagtc atcgctatta gcatggtgat gcggttttgg cagtacatca atgggcgtgg     420
atagcggttt gactcacggg gatttccaag tctccacccc attgacgtca atgggagttt     480
gttttggcac caaaatcaac gggactttcc aaaatgtcgt aacaactccg ccccattgac     540
gcaaatgggc ggtaggcgtg tacggtggga ggtctatata agcagagctc gtttagtga     600 acg                                                                   603
```

-continued

```
<210> SEQ ID NO 2
<211> LENGTH: 603
<212> TYPE: DNA
<213> ORGANISM: Human cytomegalovirus

<400> SEQUENCE: 2
atgttgatat tgattattga ttagttatta atagtaatta attacggggt tattagttta      60
tagtttatat atggagtttc gcgttatata atttacggta aatggttcgt ttggttgatc     120
gtttaacgat tttcgtttat tgacgttaat aatgacgtat gttttatag taacgttaat      180 agggattttt tattgacgtt aatgggtgga gtatttacgg taaattgttt atttggtagt     240
atattaagtg tattatatgt taagtacgtt tttattgac gttaatgacg gtaaatggtt      300
cgtttggtat tatgtttagt atatgatttt atgggatttt tttatttggt agtatattta    360
cgtattagtt atcgttatta gtatggtgat gcggttttgg tagtatatta atgggcgtgg    420
atagcggttt gatttacggg gattttaag ttttatttt attgacgtta atgggagttt      480
gttttggtat taaaattaac gggatttttt aaaatgtcgt ataatttcg ttttattgac     540 gtaaatgggc ggtaggcgtg tacggtggga ggtttatata agtagagttt cgtttagtga    600
acg                                                                    603

<210> SEQ ID NO 3
<211> LENGTH: 603
<212> TYPE: DNA
<213> ORGANISM: Human cytomegalovirus

<400> SEQUENCE: 3
atgttgatat tgattattga ttagttatta atagtaatta attatggggt tattagttta      60
tagtttatat atggagtttt gtgttatata atttatggta aatggtttgt ttggttgatt     120
gtttaatgat ttttgtttat tgatgttaat aatgatgtat gttttatag taatgttaat      180 agggattttt tattgatgtt aatgggtgga gtatttatgg taaattgttt atttggtagt     240
atattaagtg tattatatgt taagtatgtt tttattgat gttaatgatg gtaaatggtt      300
tgtttggtat tatgtttagt atatgatttt atgggatttt tttatttggt agtatattta    360
tgtattagtt attgttatta gtatggtgat gtggttttgg tagtatatta atgggtgtgg    420
atagtggttt gatttatggg gattttaag ttttatttt attgatgtta atgggagttt      480
gttttggtat taaaattaat gggatttttt aaaatgttgt ataatttg ttttattgat      540 gtaaatgggt ggtaggtgtg tatggtggga ggtttatata agtagagttt tgtttagtga    600
atg                                                                    603

<210> SEQ ID NO 4
<211> LENGTH: 603
<212> TYPE: DNA
<213> ORGANISM: Human cytomegalovirus

<400> SEQUENCE: 4
cgtttattaa acggagtttt gtttatatag atttttatc gtatacgttt atcgtttatt      60
tgcgttaatg gggcggagtt gttacgatat tttggaaagt ttcgttgatt ttggtgttaa    120
aataaatttt tattgacgtt aatggggtgg agatttggaa attttcgtga gttaaatcgt    180
tatttacgtt tattgatgta ttgttaaaat cgtattatta tgttaatagc gatgattaat    240
acgtagatgt attgttaagt aggaaagttt tataaggtta tgtattgggt ataatgttag    300
gcgggttatt tatcgttatt gacgttaata ggggcgtat ttggtatatg atatatttga    360
```

```
tgtattgtta agtgggtagt ttatcgtaaa tattttattt attgacgtta atggaaagtt      420
tttattggcg ttattatggg aatatacgtt attattgacg ttaatgggcg ggggtcgttg      480
ggcggttagt taggcgggtt atttatcgta agttatgtaa cgcggaattt tatatatggg      540
ttatgaatta atgatttcgt aattgattat tattaataat tagttaataa ttaatgttaa      600
tat                                                                    603

<210> SEQ ID NO 5
<211> LENGTH: 603
<212> TYPE: DNA
<213> ORGANISM: Human cytomegalovirus

<400> SEQUENCE: 5
tgtttattaa atggagtttt gtttatatag attttttatt gtatatgttt attgtttatt       60
tgtgttaatg gggtggagtt gttatgatat tttggaaagt tttgttgatt ttggtgttaa      120
aataaatttt tattgatgtt aatggggtgg agatttggaa attttgtga gttaaattgt       180 tatttatgtt tattgatgta ttgttaaaat tgtattatta tgttaatagt gatgattaat      240
atgtagatgt attgttaagt aggaaagttt taaggttaa tgtattgggt ataatgttag       300
gtgggttatt tattgttatt gatgttaata ggggtgtat ttggtatatg atatatttga       360
tgtattgtta agtgggtagt ttattgtaaa tattttattt attgatgtta atggaaagtt      420
tttattggtg ttattatggg aatatatgtt attattgatg ttaatgggtg ggggttgttg      480
ggtggttagt taggtgggtt atttattgta agttatgtaa tgtggaattt tatatatggg      540
ttatgaatta atgattttgt aattgattat tattaataat tagttaataa ttaatgttaa      600
tat                                                                    603

<210> SEQ ID NO 6
<211> LENGTH: 24
<212> TYPE: DNA
<213> ORGANISM: Artificial Sequence
<220> FEATURE:
<223> OTHER INFORMATION: Primer 227

<400> SEQUENCE: 6
atgttgatat tgattattga ttag                                              24

<210> SEQ ID NO 7
<211> LENGTH: 24
<212> TYPE: DNA
<213> ORGANISM: Artificial Sequence
<220> FEATURE:
<223> OTHER INFORMATION: Primer 228

<400> SEQUENCE: 7
tatgggattt ttttatttgg tagt                                              24

<210> SEQ ID NO 8
<211> LENGTH: 24
<212> TYPE: DNA
<213> ORGANISM: Artificial Sequence
<220> FEATURE:
<223> OTHER INFORMATION: Primer 229

<400> SEQUENCE: 8
actcctctcc caaaactaaa tcta                                              24

<210> SEQ ID NO 9
<211> LENGTH: 21
```

<212> TYPE: DNA
<213> ORGANISM: Artificial Sequence
<220> FEATURE:
<223> OTHER INFORMATION: Primer 237

<400> SEQUENCE: 9
ccaaaacaaa ctcccattaa c                                    21

<210> SEQ ID NO 10
<211> LENGTH: 24
<212> TYPE: DNA
<213> ORGANISM: Artificial Sequence
<220> FEATURE:
<223> OTHER INFORMATION: Primer 238

<400> SEQUENCE: 10
ggggttatta gtttatagtt tata                                 24

<210> SEQ ID NO 11
<211> LENGTH: 28
<212> TYPE: DNA
<213> ORGANISM: Artificial Sequence
<220> FEATURE:
<223> OTHER INFORMATION: Primer 239

<400> SEQUENCE: 11
tggtattatg tttagtatat gattttat                             28

<210> SEQ ID NO 12
<211> LENGTH: 25
<212> TYPE: DNA
<213> ORGANISM: Artificial Sequence
<220> FEATURE:
<223> OTHER INFORMATION: Primer 240

<400> SEQUENCE: 12 ggatttttt atttggtagt atatt                                 25

<210> SEQ ID NO 13
<211> LENGTH: 21
<212> TYPE: DNA
<213> ORGANISM: Artificial Sequence
<220> FEATURE:
<223> OTHER INFORMATION: Primer 254

<400> SEQUENCE: 13
aaatccccgt aaatcaaacc g                                    21

<210> SEQ ID NO 14
<211> LENGTH: 26
<212> TYPE: DNA
<213> ORGANISM: Artificial Sequence
<220> FEATURE:
<223> OTHER INFORMATION: Primer 263

<400> SEQUENCE: 14
gggatttttt tatttggtag tatatt                               26

<210> SEQ ID NO 15
<211> LENGTH: 25
<212> TYPE: DNA
<213> ORGANISM: Artificial Sequence
<220> FEATURE:
<223> OTHER INFORMATION: Primer 264

<400> SEQUENCE: 15
tatgggattt ttttatttgg tagta                                           25

<210> SEQ ID NO 16
<211> LENGTH: 19
<212> TYPE: DNA
<213> ORGANISM: Artificial Sequence
<220> FEATURE:
<223> OTHER INFORMATION: Primer 265

<400> SEQUENCE: 16
atccccgtaa atcaaaccg                                                  19

<210> SEQ ID NO 17
<211> LENGTH: 18
<212> TYPE: DNA
<213> ORGANISM: Artificial Sequence
<220> FEATURE:
<223> OTHER INFORMATION: Primer 266

<400> SEQUENCE: 17
tccccgtaaa tcaaaccg                                                   18

<210> SEQ ID NO 18
<211> LENGTH: 17
<212> TYPE: DNA
<213> ORGANISM: Artificial Sequence
<220> FEATURE:
<223> OTHER INFORMATION: Primer 267

<400> SEQUENCE: 18
ccccgtaaat caaaccg                                                    17

<210> SEQ ID NO 19
<211> LENGTH: 17
<212> TYPE: DNA
<213> ORGANISM: Artificial Sequence
<220> FEATURE:
<223> OTHER INFORMATION: Primer 268

<400> SEQUENCE: 19
cccgtaaatc aaaccgc                                                    17

<210> SEQ ID NO 20
<211> LENGTH: 21
<212> TYPE: DNA
<213> ORGANISM: Artificial Sequence
<220> FEATURE:
<223> OTHER INFORMATION: Primer 262

<400> SEQUENCE: 20
aaatccccrt aaatcaaacc g                                               21

<210> SEQ ID NO 21
<211> LENGTH: 628
<212> TYPE: DNA
<213> ORGANISM: Artificial Sequence
<220> FEATURE:
<223> OTHER INFORMATION: Template #11

<400> SEQUENCE: 21
atgttgatat tgattattga ttagttatta atagtaatta attatggggt tattagttta     60
tagttcatat atggagtttt gtgttatata atttatggta aatggtttgt ttggttgatt    120
gtttaatgat ttttgtttat tgatgttaat aatgatgtat gtttttatag taatgttaat    180
agggattttt tattgatgtt aatgggtgga gtatttatgg taaattgttt atttggtagt    240

| atattaagtg tattatatgt taagtatgtt ttttattgat gttaatgatg gtaaatggtt | 300 |
| tgtttggtat tatgtttagt atatgatttt atgggatttt tttatttggt agtatattta | 360 |
| tgtattagtt attgttatta gtatggtgat gtggttttgg tagtatatta atgggtgtgg | 420 |
| atagtggttt gatttatggg gattttttaag ttttttatttt attgatgtta atgggagttt | 480 |
| gttttggtat taaaattaat gggatttttt aaaatgttgt ataaattttg ttttattgat | 540 |
| gtaaatgggt ggtaggtgtg tatggtggga ggtttatata agtagagttt tgtttagtga | 600 |
| atgttagatt tagttttggg agaggagt | 628 |

<210> SEQ ID NO 22
<211> LENGTH: 629
<212> TYPE: DNA
<213> ORGANISM: Artificial Sequence
<220> FEATURE:
<223> OTHER INFORMATION: Template #62

<400> SEQUENCE: 22

| atgttgatat tgattattga ttagttatta atagtaatta attatggggt tattagttta | 60 |
| tagttyatat atggagtttty gygttatata atttatgrta aatggtttgt ttggttgatt | 120 |
| gtttaatgat ttttgtttat tgatgttaat aatgatgtat gtttttatag taatgttaat | 180 |
| agggattttt tattgatgtt aatgggtgga gtatttatgg taaaytgttt atttggtagt | 240 |
| atattaagtg tattatatgt taagtatgtt ttttattgat gttaatgatg gtaaatggtt | 300 |
| tgtttggtat tatgtttagt atatgatttt atgggatttt tttatttggt agtatattta | 360 |
| ygtattagtt atygttatta gtatggtgat gtggttttgg tagtatatta atgggcgtgg | 420 |
| atagcggttt gatttacggg gattttttaag ttttttatttt attgatgtta atgggagttt | 480 |
| gttttggtat taaaattaat gggatttttt aaaatgttgt ataaattttg ttttattgat | 540 |
| gtaaatgggt ggtaggtgtg tacggtggga ggtttatata agtagagttt cgtttagtga | 600 |
| atcgttagat ttagttttgg gagaggagt | 629 |

<210> SEQ ID NO 23
<211> LENGTH: 629
<212> TYPE: DNA
<213> ORGANISM: Artificial Sequence
<220> FEATURE:
<223> OTHER INFORMATION: Template #01

<400> SEQUENCE: 23

| atgttgatat tgattattga ttagttatta atagtaatta attatgggggt tattagttta | 60 |
| tagtttatat atggagtttt gtgttatata atttatggta aatggtttgt ttggttgatt | 120 |
| gtttaatgat ttttgtttat tgatgttaat aatgatgtat gtttttatag taatgttaat | 180 |
| agggattttt tattgatgtt aatgggtgga gtatttatgg taaattgttt atttggcagt | 240 |
| atattaagtg tattatatgt taagtatgtt ttttattgat gttaatgatg gtaaatggtt | 300 |
| cgtttggtat tatgtttagt atatgatttt atgggatttt tttatttggt agtatattta | 360 |
| tgtattagtt attgttatta gtatggtgat gtggttttgg tagtatatta atgggtgtgg | 420 |
| atagcggttt gatttatggg gattttttaag ttttttatttt attgatgtta atgggagttt | 480 |
| gttttggtat taaaattaat gggatttttt aaaatgttgt ataaattttg ttttattgat | 540 |
| gtaaatgggt ggtaggtgtg tacggtggga ggtttatata agtagagttt tgtttagtga | 600 |
| attgttagat ttagttttgg gagaggagt | 629 |

<210> SEQ ID NO 24
<211> LENGTH: 629
<212> TYPE: DNA
<213> ORGANISM: Artificial Sequence
<220> FEATURE:
<223> OTHER INFORMATION: Template #04

<400> SEQUENCE: 24

| | | | | | |
|---|---|---|---|---|---|
| atgttgatat | tgattattga | ttagttatta | atagtaatta | attatggggt | tattagttta | 60 |
| tagtttatat | atggagtttt | gtgttatata | atttatggta | aatggtttgt | ttggttgatt | 120 |
| gtttaatgat | ttttgtttat | tgatgttaat | aatgatgtat | gtttttatag | taatgttaat | 180 |
| agggattttt | tattgatgtt | aatgggtgga | gtatttatgg | taaattgttt | atttggtagt | 240 |
| atattaagtg | tattatatgt | taagtatgtt | ttttattgat | gttaatgatg | gtaaatggtt | 300 |
| tgtttggtat | tatgtttagt | atatgatttt | atgggatttt | tttatttggt | agtatattta | 360 |
| tgtattagtt | attgttatta | gtatggtgat | gtggttttgg | tagtatatta | atgggtgtgg | 420 |
| atagtggttt | gatttacggg | gattttttaag | ttttta | attgatgtta | atgggagttt | 480 |
| gttttggtat | taaaattaat | gggattttttt | aaaatgttgt | aataattttg | ttttattgat | 540 |
| gtaaatgggt | ggtaggtgtg | tacgtgggga | ggtttatata | agtagagttt | tgtttagtga | 600 |
| attgttagat | ttagttttgg | gagaggagt | | | | 629 |

<210> SEQ ID NO 25
<211> LENGTH: 629
<212> TYPE: DNA
<213> ORGANISM: Artificial Sequence
<220> FEATURE:
<223> OTHER INFORMATION: Template #16

<400> SEQUENCE: 25

| | | | | | |
|---|---|---|---|---|---|
| atgttgatat | tgattattga | ttagttatta | atagtaatta | attatggggt | tattagttta | 60 |
| tagtttatat | atggagtttt | gtgttatata | atttacggta | aatggtttgt | ttggttgatc | 120 |
| gtttaacgat | tttcgtttat | tgatgttaat | aatgacgtat | gtttttatag | taatgttaat | 180 |
| agggattttt | tattgatgtt | aatgggtgga | gtatttacgg | taaattgttt | atttggtagt | 240 |
| atattaagtg | tattatatgt | taagtatgtt | ttttattgat | gttaatgatg | gtaaatggtt | 300 |
| tgtttggtat | tatgtttagt | atatgatttt | atgggactttt | cttatttggt | agtatattta | 360 |
| cgtattagtt | atcgttatta | gtatggtgat | gtggttttgg | tagtatatta | atgggcgtgg | 420 |
| atagcggttt | gatttacggg | gattttttaag | ttttta | attgatgtta | atgggagttt | 480 |
| gttttggtat | taaaattaat | gggattttttt | aaaatgttgt | aataattttg | ttttattgat | 540 |
| gtaaatgggt | ggtaggtgtg | tatggtggga | ggtttatata | agtagagttt | tgtttagtga | 600 |
| attgttagat | ttagttttgg | gagaggagt | | | | 629 |

<210> SEQ ID NO 26
<211> LENGTH: 20
<212> TYPE: DNA
<213> ORGANISM: Artificial Sequence
<220> FEATURE:
<223> OTHER INFORMATION: primer 133

<400> SEQUENCE: 26
tcacagagca ggacagcaag                                            20

<210> SEQ ID NO 27
<211> LENGTH: 20

```
<212> TYPE: DNA
<213> ORGANISM: Artificial Sequence
<220> FEATURE:
<223> OTHER INFORMATION: primer 132

<400> SEQUENCE: 27
gacttcgcag gcgtagactt                                              20

<210> SEQ ID NO 28
<211> LENGTH: 24
<212> TYPE: DNA
<213> ORGANISM: Artificial Sequence
<220> FEATURE:
<223> OTHER INFORMATION: primer 166

<400> SEQUENCE: 28
agcacctaca gcctcagcag cacc                                         24

<210> SEQ ID NO 29
<211> LENGTH: 17
<212> TYPE: DNA
<213> ORGANISM: Artificial Sequence
<220> FEATURE:
<223> OTHER INFORMATION: primer 178

<400> SEQUENCE: 29
cgaaccggtg acggtgt                                                 17

<210> SEQ ID NO 30
<211> LENGTH: 17
<212> TYPE: DNA
<213> ORGANISM: Artificial Sequence
<220> FEATURE:
<223> OTHER INFORMATION: primer 180

<400> SEQUENCE: 30
gagggcacgg tcaccac                                                 17

<210> SEQ ID NO 31
<211> LENGTH: 24
<212> TYPE: DNA
<213> ORGANISM: Artificial Sequence
<220> FEATURE:
<223> OTHER INFORMATION: primer 185

<400> SEQUENCE: 31
cacaccttcc cggctgtcct acag                                         24

<210> SEQ ID NO 32
<211> LENGTH: 20
<212> TYPE: DNA
<213> ORGANISM: Artificial Sequence
<220> FEATURE:
<223> OTHER INFORMATION: 396 - hCMV-MIE forward 1

<400> SEQUENCE: 32
tacatcaatg ggcgtggata                                              20

<210> SEQ ID NO 33
<211> LENGTH: 20
<212> TYPE: DNA
<213> ORGANISM: Artificial Sequence
<220> FEATURE:
<223> OTHER INFORMATION: 397 - hCMV-MIE reverse 1

<400> SEQUENCE: 33
```
aagtcccgtt gattttggtg                                                    20

<210> SEQ ID NO 34
<211> LENGTH: 18
<212> TYPE: DNA
<213> ORGANISM: Artificial Sequence
<220> FEATURE:
<223> OTHER INFORMATION: Gusb forward 1

<400> SEQUENCE: 34
cagggtggga tgctcttc                                                      18

<210> SEQ ID NO 35
<211> LENGTH: 18
<212> TYPE: DNA
<213> ORGANISM: Artificial Sequence
<220> FEATURE:
<223> OTHER INFORMATION: Gusb reverse 1

<400> SEQUENCE: 35
gccggttttc cgagaagt                                                      18

<210> SEQ ID NO 36
<211> LENGTH: 18
<212> TYPE: DNA
<213> ORGANISM: Artificial Sequence
<220> FEATURE:
<223> OTHER INFORMATION: Eif3i forward 1

<400> SEQUENCE: 36
gttcccggca ctgacact                                                      18

<210> SEQ ID NO 37
<211> LENGTH: 20
<212> TYPE: DNA
<213> ORGANISM: Artificial Sequence
<220> FEATURE:
<223> OTHER INFORMATION: Eif3i reverse 2

<400> SEQUENCE: 37
acttgatctg cgtgatggac                                                    20

<210> SEQ ID NO 38
<211> LENGTH: 20
<212> TYPE: DNA
<213> ORGANISM: Artificial Sequence
<220> FEATURE:
<223> OTHER INFORMATION: Fox2a forward 1

<400> SEQUENCE: 38
atcacccgta ctgctgctct                                                    20

<210> SEQ ID NO 39
<211> LENGTH: 20
<212> TYPE: DNA
<213> ORGANISM: Artificial Sequence
<220> FEATURE:
<223> OTHER INFORMATION: Fox2a reverse

<400> SEQUENCE: 39
gaggcttctg gggatctctt                                                    20

<210> SEQ ID NO 40
<211> LENGTH: 20
<212> TYPE: DNA
<213> ORGANISM: Artificial Sequence

```
<220> FEATURE:
<223> OTHER INFORMATION: Gata5 forward 1

<400> SEQUENCE: 40
cacctacccc atcctgtctg                                              20

<210> SEQ ID NO 41
<211> LENGTH: 21
<212> TYPE: DNA
<213> ORGANISM: Artificial Sequence
<220> FEATURE:
<223> OTHER INFORMATION: Gata5 reverse 1

<400> SEQUENCE: 41
gaggaggtga aggcaaagtc t                                            21

<210> SEQ ID NO 42
<211> LENGTH: 20
<212> TYPE: DNA
<213> ORGANISM: Artificial Sequence
<220> FEATURE:
<223> OTHER INFORMATION: Rho forward 1

<400> SEQUENCE: 42
agcctcggtc tctattgacg                                              20

<210> SEQ ID NO 43
<211> LENGTH: 20
<212> TYPE: DNA
<213> ORGANISM: Artificial Sequence
<220> FEATURE:
<223> OTHER INFORMATION: Rho reverse 1

<400> SEQUENCE: 43
cgttggagaa gggcacataa                                              20

<210> SEQ ID NO 44
<211> LENGTH: 36
<212> TYPE: DNA
<213> ORGANISM: Artificial Sequence
<220> FEATURE:
<223> OTHER INFORMATION: UG_730_Bisul_CMV1 F1

<400> SEQUENCE: 44
gatattgatt attgattagt tattaatagt aattaa                            36

<210> SEQ ID NO 45
<211> LENGTH: 33
<212> TYPE: DNA
<213> ORGANISM: Artificial Sequence
<220> FEATURE:
<223> OTHER INFORMATION: UG_731_Bisul_CMV1 R1

<400> SEQUENCE: 45
caaataaaaa aatcccataa aatcatatac taa                               33

<210> SEQ ID NO 46
<211> LENGTH: 33
<212> TYPE: DNA
<213> ORGANISM: Artificial Sequence
<220> FEATURE:
<223> OTHER INFORMATION: UG_732_Bisul_CMV2 F2

<400> SEQUENCE: 46
ttagtatatg attttatggg attttttat ttg                                33
```

```
<210> SEQ ID NO 47
<211> LENGTH: 25
<212> TYPE: DNA
<213> ORGANISM: Artificial Sequence
<220> FEATURE:
<223> OTHER INFORMATION: UG_733_Bisul_CMV2 R2

<400> SEQUENCE: 47
ttctaatact aaactcctct cccaa                                         25

<210> SEQ ID NO 48
<211> LENGTH: 23
<212> TYPE: DNA
<213> ORGANISM: Artificial Sequence
<220> FEATURE:
<223> OTHER INFORMATION: UG_574_16110 BtsI_rev

<400> SEQUENCE: 48
ctgtcatgcc atcgtaagat gct                                           23

<210> SEQ ID NO 49
<211> LENGTH: 24
<212> TYPE: DNA
<213> ORGANISM: Artificial Sequence
<220> FEATURE:
<223> OTHER INFORMATION: UG_575_16110 BtsI_for

<400> SEQUENCE: 49
gcggccaact tacttctgac aacg                                          24

<210> SEQ ID NO 50
<211> LENGTH: 24
<212> TYPE: DNA
<213> ORGANISM: Artificial Sequence
<220> FEATURE:
<223> OTHER INFORMATION: UG_576_16110 AceIII_rev

<400> SEQUENCE: 50
aaggcgagtt acatgatccc ccat                                          24

<210> SEQ ID NO 51
<211> LENGTH: 23
<212> TYPE: DNA
<213> ORGANISM: Artificial Sequence
<220> FEATURE:
<223> OTHER INFORMATION: UG_577_16110 AceIII_for

<400> SEQUENCE: 51
caccacgatg cctgtagcaa tgg                                           23

<210> SEQ ID NO 52
<211> LENGTH: 20
<212> TYPE: DNA
<213> ORGANISM: Artificial Sequence
<220> FEATURE:
<223> OTHER INFORMATION: UNC13c forward 1

<400> SEQUENCE: 52
gggtgcttta cggaaactga                                               20

<210> SEQ ID NO 53
<211> LENGTH: 20
<212> TYPE: DNA
<213> ORGANISM: Artificial Sequence
```

```
<220> FEATURE:
<223> OTHER INFORMATION: UNC13c reverse 1

<400> SEQUENCE: 53
gcttcttatg ccccaggttt                                                    20
```